US012573050B2

(12) United States Patent
Richter et al.

(10) Patent No.: US 12,573,050 B2
(45) Date of Patent: Mar. 10, 2026

(54) SYSTEMS AND METHODS FOR PLATFORM AGNOSTIC WHOLE BODY IMAGE SEGMENTATION

(71) Applicant: EXINI Diagnostics AB, Lund (SE)

(72) Inventors: Jens Filip Andreas Richter, Staffanstorp (SE); Kerstin Elsa Maria Johnsson, Lund (SE); Erik Konrad Gjertsson, Lund (SE); Aseem Undvall Anand, Queens, NY (US)

(73) Assignee: EXINI Diagnostics AB, Lund (SE)

( * ) Notice: Subject to any disclaimer, the term of this patent is extended or adjusted under 35 U.S.C. 154(b) by 0 days.

(21) Appl. No.: 18/429,322

(22) Filed: Jan. 31, 2024

(65) Prior Publication Data

US 2024/0169546 A1 May 23, 2024

Related U.S. Application Data

(62) Division of application No. 18/127,991, filed on Mar. 29, 2023, now Pat. No. 11,941,817, which is a (Continued)

(51) Int. Cl.

*G06T 7/00* (2017.01)
*A61B 6/00* (2006.01)

(Continued)

(52) U.S. Cl.

CPC ................ *G06T 7/11* (2017.01); *A61B 6/032* (2013.01); *A61B 6/037* (2013.01); *A61B 6/463* (2013.01);

(Continued)

(58) Field of Classification Search

CPC ........................................................ G06T 7/11
See application file for complete search history.

(56) References Cited

U.S. PATENT DOCUMENTS 5,762,608 A 6/1998 Warne et al.
6,944,330 B2 9/2005 Novak et al.

(Continued)

FOREIGN PATENT DOCUMENTS

CN 1200520 A 12/1998
CN 1518719 A 8/2004

(Continued)

OTHER PUBLICATIONS

Ali, A. et al., The Automated Bone Scan Index as a Predictor of Response to Prostate Radiotherapy in Men with Newly Diagnosed Metastatic Prostate Cancer: An Exploratory Analysis of STAMPEDE's "M1 |RT Comparison", European Urology Oncology 3:412-419, (2020).

(Continued)

*Primary Examiner* — Joseph M Santos Rodriguez
(74) *Attorney, Agent, or Firm* — Choate, Hall & Stewart LLP; William R. Haulbrook; Ronen Adato

(57) ABSTRACT

Presented herein are systems and methods that provide for automated analysis of three-dimensional (3D) medical images of a subject in order to automatically identify specific 3D volumes within the 3D images that correspond to specific anatomical regions (e.g., organs and/or tissue). Notably, the image analysis approaches described herein are not limited to a single particular organ or portion of the body. Instead, they are robust and widely applicable, providing for consistent, efficient, and accurate detection of anatomical regions, including soft tissue organs, in the entire body. In certain embodiments, the accurate identification of one or more such volumes is used to automatically determine quantitative metrics that represent uptake of radiopharmaceuticals in particular organs and/or tissue regions. These uptake metrics can be used to assess disease state in a (Continued)

subject, determine a prognosis for a subject, and/or determine efficacy of a treatment modality.

19 Claims, 26 Drawing Sheets
(20 of 26 Drawing Sheet(s) Filed in Color)

Related U.S. Application Data division of application No. 16/734,599, filed on Jan. 6, 2020, now Pat. No. 11,657,508.

(60) Provisional application No. 62/934,305, filed on Nov. 12, 2019, provisional application No. 62/907,158, filed on Sep. 27, 2019, provisional application No. 62/870,210, filed on Jul. 3, 2019, provisional application No. 62/863,608, filed on Jun. 19, 2019, provisional application No. 62/837,941, filed on Apr. 24, 2019, provisional application No. 62/789,155, filed on Jan. 7, 2019.

(51) Int. Cl.

| | |
|---|---|
| ***A61B 6/03*** | (2006.01) |
| ***A61B 6/46*** | (2024.01) |
| ***A61B 6/50*** | (2024.01) |
| ***A61K 51/04*** | (2006.01) |
| ***G06F 18/214*** | (2023.01) |
| ***G06T 7/11*** | (2017.01) |
| ***G06V 20/64*** | (2022.01) |
| ***G06V 20/69*** | (2022.01) |
| ***G06V 30/24*** | (2022.01) |
| ***G16H 30/20*** | (2018.01) |
| ***G16H 30/40*** | (2018.01) |
| ***G16H 50/20*** | (2018.01) |
| ***G16H 50/30*** | (2018.01) |
| ***G16H 50/50*** | (2018.01) |

(52) U.S. Cl.
CPC .............. *A61B 6/466* (2013.01); *A61B 6/481* (2013.01); *A61B 6/505* (2013.01); *A61B 6/507* (2013.01); *A61B 6/5205* (2013.01); *A61B 6/5241* (2013.01); *A61B 6/5247* (2013.01); *A61K 51/0455* (2013.01); *G06F 18/214* (2023.01); *G06V 20/64* (2022.01); *G06V 20/695* (2022.01); *G06V 20/698* (2022.01); *G06V 30/2504* (2022.01); *G16H 30/20* (2018.01); *G16H 30/40* (2018.01); *G16H 50/20* (2018.01); *G16H 50/30* (2018.01); *G16H 50/50* (2018.01); *G06V 2201/031* (2022.01); *G06V 2201/033* (2022.01)

(56) References Cited

U.S. PATENT DOCUMENTS

| | | | |
|---|---|---|---|
| 7,450,747 | B2 | 11/2008 | Jabri et al. |
| 7,751,605 | B2 | 7/2010 | Gündel et al. |
| 7,876,938 | B2 | 1/2011 | Huang et al. |
| 7,935,055 | B2 | 5/2011 | Burckhardt |
| 7,970,194 | B2 | 6/2011 | Kimura |
| 8,199,985 | B2 | 6/2012 | Jakobsson et al. |
| 8,211,401 | B2 | 7/2012 | Babich et al. |
| 8,467,856 | B2 | 6/2013 | Renisch et al. |
| 8,538,166 | B2 | 9/2013 | Gordon et al. |
| 8,606,349 | B2 | 12/2013 | Rousso et al. |
| 8,705,887 | B2 | 4/2014 | Ma et al. |
| 8,778,305 | B2 | 7/2014 | Pomper et al. |
| 8,855,387 | B2 | 10/2014 | Hamadeh et al. |
| 8,962,799 | B2 | 2/2015 | Babich et al. |
| 8,995,736 | B2 | 3/2015 | Kaufman et al. |
| 9,002,081 | B2 | 4/2015 | Brown |
| 9,028,800 | B2 | 5/2015 | D'Souza et al. |
| 9,466,133 | B2 | 10/2016 | Sowards-Emmerd et al. |
| 9,710,915 | B2 | 7/2017 | Firouzian et al. |
| 9,721,340 | B2 | 8/2017 | Gillies et al. |
| 10,058,393 | B2 | 8/2018 | Bonutti et al. |
| 10,089,752 | B1 | 10/2018 | Bronkalla et al. |
| 10,112,974 | B2 | 10/2018 | Neumaier et al. |
| 10,140,544 | B1 | 11/2018 | Zhao et al. |
| 10,223,610 | B1 | 3/2019 | Akselrod-Ballin et al. |
| 10,311,971 | B2 | 6/2019 | Opfer et al. |
| 10,330,763 | B2 | 6/2019 | James et al. |
| 10,339,653 | B2 | 7/2019 | Gillies et al. |
| 10,340,044 | B2 | 7/2019 | Yao et al. |
| 10,340,046 | B2 | 7/2019 | Baker |
| RE47,609 | E | 9/2019 | Hamadeh et al. |
| 10,492,723 | B2 | 12/2019 | Madabhushi et al. |
| 10,600,184 | B2 | 3/2020 | Golden et al. |
| 10,665,346 | B2 | 5/2020 | Baker |
| 10,748,652 | B2 | 8/2020 | Yao et al. |
| 10,762,993 | B2 | 9/2020 | Baker |
| 10,815,200 | B2 | 10/2020 | Cardinale et al. |
| 10,818,386 | B2 | 10/2020 | Yao et al. |
| 10,943,681 | B2 | 3/2021 | Yao et al. |
| 10,973,486 | B2 | 4/2021 | Sjöstrand et al. |
| 11,011,257 | B2 | 5/2021 | Lints et al. |
| 11,094,066 | B2 | 8/2021 | Nie et al. |
| 11,321,844 | B2 | 5/2022 | Johnsson et al. |
| 11,386,988 | B2 | 7/2022 | Johnsson et al. |
| 11,424,035 | B2 | 8/2022 | Baker |
| 11,508,059 | B2 | 11/2022 | Wang et al. |
| 11,534,125 | B2 | 12/2022 | Sjöstrand et al. |
| 11,564,621 | B2 | 1/2023 | Anand et al. |
| 11,657,508 | B2 | 5/2023 | Richter et al. |
| 11,721,428 | B2 | 8/2023 | Brynolfsson et al. |
| 11,894,141 | B2 | 2/2024 | Baker |
| 11,900,597 | B2 | 2/2024 | Anand et al. |
| 11,937,962 | B2 | 3/2024 | Sjöstrand et al. |
| 11,941,817 | B2 | 3/2024 | Richter et al. |
| 12,224,067 | B1 | 2/2025 | Baker |
| 12,243,236 | B1 | 3/2025 | Richter et al. |
| 12,243,637 | B2 | 3/2025 | Brynolfsson et al. |
| 12,414,748 | B2 | 9/2025 | Sjöstrand et al. |
| 12,417,533 | B2 | 9/2025 | Anand et al. |
| 2003/0215120 | A1 | 11/2003 | Uppaluri et al. |
| 2005/0065421 | A1 | 3/2005 | Burckhardt |
| 2005/0281381 | A1 | 12/2005 | Guendel |
| 2006/0062425 | A1 | 3/2006 | Shen et al. |
| 2006/0064396 | A1 | 3/2006 | Wei et al. |
| 2006/0078183 | A1 | 4/2006 | deCharms |
| 2007/0081712 | A1 | 4/2007 | Huang et al. |
| 2007/0081713 | A1 | 4/2007 | Jerebko |
| 2007/0100225 | A1 | 5/2007 | Maschke |
| 2007/0115204 | A1 | 5/2007 | Budz et al. |
| 2007/0265230 | A1 | 11/2007 | Rousso et al. |
| 2008/0027315 | A1 | 1/2008 | McGinnis |
| 2008/0214933 | A1 | 9/2008 | Von Busch et al. |
| 2009/0213034 | A1 | 8/2009 | Wu et al. |
| 2009/0309874 | A1 | 12/2009 | Salganicoff et al. |
| 2009/0311182 | A1 | 12/2009 | Wang et al. |
| 2010/0032575 | A1 | 2/2010 | Iagaru et al. |
| 2010/0080434 | A1 | 4/2010 | Seifert et al. |
| 2010/0215581 | A1 | 8/2010 | Hoffmann |
| 2010/0266170 | A1 | 10/2010 | Khamene et al. |
| 2010/0322488 | A1 | 12/2010 | Virtue et al. |
| 2011/0007954 | A1 | 1/2011 | Suehling et al. |
| 2011/0063288 | A1 | 3/2011 | Valadez |
| 2011/0255763 | A1 | 10/2011 | Bogoni et al. |
| 2012/0123253 | A1 | 5/2012 | Renisch et al. |
| 2013/0038707 | A1 | 2/2013 | Cunningham et al. |
| 2013/0094704 | A1 | 4/2013 | Hamadeh et al. |
| 2013/0129168 | A1 | 5/2013 | Ross |
| 2013/0211231 | A1 | 8/2013 | Sundarapandian et al. |
| 2013/0281841 | A1 | 10/2013 | Everett et al. |
| 2014/0105471 | A1 | 4/2014 | Brown |
| 2014/0193336 | A1 | 7/2014 | Rousso et al. |
| 2015/0003703 | A1 | 1/2015 | Franz et al. |
| 2015/0063667 | A1 | 3/2015 | Sprencz et al. |

(56) References Cited

U.S. PATENT DOCUMENTS

| | | | |
|---|---|---|---|
| 2015/0110716 | A1 | 4/2015 | Armor |
| 2015/0119704 | A1 | 4/2015 | Roth et al. |
| 2015/0221083 | A1 | 8/2015 | Berker |
| 2015/0287188 | A1 | 10/2015 | Gazit et al. |
| 2015/0331995 | A1 | 11/2015 | Zhao et al. |
| 2015/0356730 | A1 | 12/2015 | Grove et al. |
| 2016/0012604 | A1 | 1/2016 | Firouzian et al. |
| 2016/0180042 | A1 | 6/2016 | Menon et al. |
| 2016/0203263 | A1 | 7/2016 | Maier et al. |
| 2016/0275674 | A1 | 9/2016 | Rivet-Sabourin et al. |
| 2016/0335395 | A1 | 11/2016 | Wu et al. |
| 2016/0350947 | A1 | 12/2016 | Kelly |
| 2017/0083682 | A1 | 3/2017 | McNutt et al. |
| 2017/0112577 | A1 | 4/2017 | Bonutti et al. |
| 2018/0140260 | A1 | 5/2018 | Taguchi et al. |
| 2018/0144828 | A1 | 5/2018 | Baker |
| 2018/0259608 | A1 | 9/2018 | Golden et al. |
| 2018/0360402 | A1 | 12/2018 | Carmi |
| 2019/0038239 | A1 | 2/2019 | Flohr et al. |
| 2019/0105009 | A1 | 4/2019 | Siemionow et al. |
| 2019/0105200 | A1 | 4/2019 | Hipsley |
| 2019/0209116 | A1 | 7/2019 | Sjostrand et al. |
| 2019/0333623 | A1 | 10/2019 | Hibbard |
| 2019/0388049 | A1 | 12/2019 | Gupta et al. |
| 2020/0027559 | A1 | 1/2020 | Baker |
| 2020/0051238 | A1 | 2/2020 | El Harouni et al. |
| 2020/0074634 | A1 | 3/2020 | Kecskemethy et al. |
| 2020/0085382 | A1 | 3/2020 | Taerum et al. |
| 2020/0097701 | A1 | 3/2020 | Chukka et al. |
| 2020/0126666 | A1 | 4/2020 | Baker |
| 2020/0170604 | A1 | 6/2020 | Yildirim et al. |
| 2020/0193594 | A1 | 6/2020 | Georgescu et al. |
| 2020/0193603 | A1 | 6/2020 | Golden et al. |
| 2020/0245960 | A1 | 8/2020 | Richter et al. |
| 2020/0311919 | A1 | 10/2020 | Grimmer et al. |
| 2020/0315455 | A1 | 10/2020 | Lee et al. |
| 2020/0337658 | A1 | 10/2020 | Sjostrand et al. |
| 2020/0342600 | A1 | 10/2020 | Sjostrand et al. |
| 2020/0352518 | A1 | 11/2020 | Lyman et al. |
| 2020/0357117 | A1 | 11/2020 | Lyman et al. |
| 2020/0357118 | A1 | 11/2020 | Yao et al. |
| 2020/0357521 | A1 | 11/2020 | Baker |
| 2020/0410672 | A1 | 12/2020 | Katscher et al. |
| 2021/0032206 | A1 | 2/2021 | Neumaier et al. |
| 2021/0082547 | A1 | 3/2021 | Yao et al. |
| 2021/0093249 | A1 | 4/2021 | Anand et al. |
| 2021/0183485 | A1 | 6/2021 | Yao et al. |
| 2021/0233633 | A1 | 7/2021 | Lints et al. |
| 2021/0334974 | A1 | 10/2021 | Johnsson et al. |
| 2021/0335480 | A1 | 10/2021 | Johnsson et al. |
| 2022/0005586 | A1 | 1/2022 | Brynolfsson et al. |
| 2022/0058804 | A1 | 2/2022 | Carmi |
| 2022/0142480 | A1 | 5/2022 | Peck et al. |
| 2022/0375612 | A1 | 11/2022 | Baker |
| 2022/0398724 | A1 | 12/2022 | Anand et al. |
| 2023/0115732 | A1 | 4/2023 | Brynolfsson et al. |
| 2023/0148980 | A1 | 5/2023 | Sjöstrand et al. |
| 2023/0316530 | A1 | 10/2023 | Richter et al. |
| 2023/0351586 | A1 | 11/2023 | Brynolfsson et al. |
| 2023/0410985 | A1 | 12/2023 | Brynolfsson et al. |
| 2023/0420112 | A1 | 12/2023 | Brynolfsson et al. |
| 2024/0029252 | A1 | 1/2024 | Ichinose et al. |
| 2024/0127437 | A1 | 4/2024 | Anand et al. |
| 2024/0186010 | A1 | 6/2024 | Baker |
| 2024/0285246 | A1 | 8/2024 | Sjöstrand et al. |
| 2024/0285248 | A1 | 8/2024 | Sjöstrand et al. |
| 2024/0354940 | A1 | 10/2024 | Sjöstrand et al. |
| 2025/0061580 | A1 | 2/2025 | Richter et al. |
| 2025/0062029 | A1 | 2/2025 | Baker |
| 2025/0069232 | A1 | 2/2025 | Richter et al. |
| 2025/0104225 | A1 | 3/2025 | Sjöstrand et al. |
| 2025/0191752 | A1 | 6/2025 | Sjöstrand et al. |

FOREIGN PATENT DOCUMENTS

| | | | |
|---|---|---|---|
| CN | 101528267 | A | 9/2009 |
| CN | 101639937 | A | 2/2010 |
| CN | 102096804 | A | 6/2011 |
| CN | 102361594 | A | 2/2012 |
| CN | 102438529 | A | 5/2012 |
| CN | 102947840 | A | 2/2013 |
| CN | 103607954 | A | 2/2014 |
| CN | 103930030 | A | 7/2014 |
| CN | 104463840 | A | 3/2015 |
| CN | 106127819 | A | 11/2016 |
| CN | 106558045 | A | 4/2017 |
| CN | 107563378 | A | 1/2018 |
| CN | 107644421 | A | 1/2018 |
| CN | 114219787 | A | 3/2022 |
| EP | 1426903 | A2 | 6/2004 |
| EP | 1508872 | A1 | 2/2005 |
| EP | 2816525 | A1 | 12/2014 |
| EP | 3043318 | A1 | 7/2016 |
| EP | 3811845 | A1 | 4/2021 |
| GB | 2457577 | A | 8/2009 |
| JP | 2010-029481 | A | 2/2010 |
| JP | 2011-067594 | A | 4/2011 |
| JP | 2012-533384 | A | 12/2012 |
| JP | 2014-006130 | A | 1/2014 |
| JP | 2015-513083 | A | 4/2015 |
| JP | 6013042 | B2 | 10/2016 |
| JP | 2017-500537 | A | 1/2017 |
| JP | 2017-067489 | A | 4/2017 |
| JP | 6170284 | B2 | 7/2017 |
| JP | 2017-198697 | A | 11/2017 |
| JP | 2019-537714 | A | 12/2019 |
| SE | 524500 | C2 | 8/2004 |
| TW | 201201847 | A | 1/2012 |
| TW | 201825049 | A | 7/2018 |
| TW | 201941750 | A | 11/2019 |
| TW | 202006742 | A | 2/2020 |
| WO | WO-99/05503 | A2 | 2/1999 |
| WO | WO-2007/062135 | A2 | 5/2007 |
| WO | WO-2009/084995 | A1 | 7/2009 |
| WO | WO-2010/071999 | A1 | 7/2010 |
| WO | WO-2011/010231 | A1 | 1/2011 |
| WO | WO-2011/077303 | A1 | 6/2011 |
| WO | WO-2011/091378 | A1 | 7/2011 |
| WO | WO-2011/095580 | A1 | 8/2011 |
| WO | WO-2013/059177 | A1 | 4/2013 |
| WO | WO-2013/126147 | A2 | 8/2013 |
| WO | WO-2015/058151 | A2 | 4/2015 |
| WO | WO-2016/087592 | A1 | 6/2016 |
| WO | WO-2018/014475 | A1 | 1/2018 |
| WO | WO-2018/015953 | A1 | 1/2018 |
| WO | WO-2018/081354 | A1 | 5/2018 |
| WO | WO-2019/005722 | A1 | 1/2019 |
| WO | WO-2019/103912 | A2 | 5/2019 |
| WO | WO-2019/136349 | A2 | 7/2019 |
| WO | WO-2020/144134 | A1 | 7/2020 |
| WO | WO-2020/146032 | A1 | 7/2020 |
| WO | WO-2020/190821 | A1 | 9/2020 |
| WO | WO-2020/219619 | A1 | 10/2020 |
| WO | WO-2020/219620 | A1 | 10/2020 |
| WO | WO-2021/061315 | A1 | 4/2021 |
| WO | WO-2022/008374 | A1 | 1/2022 |
| WO | WO-2022/215530 | A1 | 10/2022 |
| WO | WO-2023/057411 | A9 | 7/2023 |
| WO | WO-2023/239829 | A2 | 12/2023 |
| WO | WO-2024/173297 | A1 | 8/2024 |
| WO | WO-2024/211651 | A1 | 10/2024 |
| WO | WO-2025/072177 | A1 | 4/2025 |

OTHER PUBLICATIONS

American College of Radiology (ACR) and the Society for Pediatric Radiology (SPR), ACR-SPR Practice Parameter For The Performance Of Skeletal Scintigraphy (Bone Scan), Resolution 28, (2013—Revused2017), available from: <http://www.acr.org>, 9 pages (2017).

(56) References Cited

OTHER PUBLICATIONS

Anand, A. et al., A Pre-Analytical Validation Study of Automated Bone Scan Index: Effect on Accuracy and Reproducibility Due to the Procedural Variabilities in Bone Scan Image Acquisition. J Nucl Med. pages 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

Armstrong, A. J. et al., Phase 3 prognostic analysis of the automated bone scan index (aBSI) in men with bone-metastatic castration-resistant prostate cancer (CRPC), Meeting Library ASC University, 11 pages (2017).

Bai, P. et. al., Body region localization in whole-body low-dose CT images of PET/CT scans using virtual landmarks, Medical Physics Wiley USA, 46(3): 1286-1299 (2019).

Belal, S. et al., Association of PET Index quantifying skeletal uptake in NaF PET/CT images with overall survival in prostate cancer patients, ASCO GU 2017, Poster 178, 1 page, presented Feb. 16, 2017.

Belal, S. et al., PET Index quantifying skeletal uptake in NaF PET/CT images with overall survival in prostate cancer patients, ASCO GU 2017, Abstract, 1 page, (Feb. 13, 2017).

Belal, S. L. et al., 3D skeletal uptake of $^{18}$F sodium fluoride in PET/CT images is associate with overall survival in patients with prostate cancer, EJNMMI Research, 7(15):1-8 (2017).

Belal, S.L. et al., Automated evaluation of normal uptake in different skeletal parts in 18F-sodium fluoride (NaF) PET/CT using a new convolutional neural network method, Ejnmmi, Eanm '17, 44(Suppl 2):S119-S956, Abstract EP-0116 (2017).

Blue Earth Diagnostics, Posluma Highlights of Prescribing Information, 12 pages, (2023).

Bombardieri, E. et al., Bone scintigraphy: procedure guidelines for tumour imaging, Eur J. Nucl. Med. Mol. Imaging, 30:BP99-BP106, (2003).

Brynolfsson, J., et. al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pages S1 and S403-404, Retrieved Sep. 18, 2020.

Brynolfsson, J., et al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.

Bushberg, J. T. et al., Essential Physics of Medical Imaging, Essential Physics of Medical Imaging, 19.3: p. 581 (table 15-3), p. 713 paragraph 6, section 19.3 and p. 720, (2011).

Capobianco, N. et al., Whole-body uptake classification and prostate cancer staging in $^{68}$Ga-PSMA-11 PET/CT using dual-tracer learning, European Journal of Nuclear Medicine and Molecular Imaging, (2021), <https:/doi.org/10.1007/s00259-021-05473-2> 10 pages. Retrieved on Apr. 18, 2021.

Ceci, F. et al., E-PSMA: the EANM standardized reporting guidelines v1.0 for PSMA-PET, European Journal of Nuclear Medicine and Molecular Imaging, 48:1626-1638, (2021).

Cha, K. H., et al. Urinary bladder segmentation in CT urography using deep-learning convolutional neural network and level sets, Medical physics, 43(4):1882-1896, (2016).

Christ, P.F. et al., Automatic Liver and Tumor Segmentation of CT and MRI Volumes Using Cascaded Fully Convolutional Neural Networks, Arxiv.org, Cornell University Library, 20 pages, (2017).

Ciernik, I. F., et al. 3D-segmentation of the 18F-choline PET signal for target volume definition in radiation therapy of the prostate, Technology in cancer research & treatment 6(1): 23-30, (2007).

Dennis, E. et al., Bone Scan Index: A Quantitative Treatment Response Biomarker for Castration-Resistant Metastatic Prostate Cancer, Journal of Clinical Oncology, 30(5):519-524 (2012).

Dertat, A., Applied Deep Learning—Part 4: Convolutional Neural Networks, Towards Data Science,<http://towardsdatascience.com/applied-deep-learning-part-4-convolutional-neural-networks-584bc134c1e2> 26 pages, (2017).

Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).

Emmett, L. et al., The PRIMARY Score: Using Intraprostatic 68Ga-PSMA PET/CT Patterns to Optimize Prostate Cancer Diagnosis, J. Nucl. Med., 63(11):1644-1650 (2022).

Fendler, W.P. et al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).

Gafita, A. et al., Novel Framework for Treatment Response Evaluation Using PSMA PET/CT in Patients with Metastatic Castration-Resistant Prostate Cancer (RECIP 1.0): An International Multicenter Study, J. Nucl. Med., 63(11):1651-1658 (2022).

GE Healthcare, Spect/CT Cameras, 2 pages, retrieved Oct. 25, 2017: <http://www3.gehealthcare.com.sg/en-gb/products/categories/nuclear_medicine/spect-ct_cameras>.

Ghosh, P. and Mitchell, M., Prostate segmentation on pelvic CT images using a genetic algorithm, Proceedings of SPIE, vol. 6914, Medical Imaging 2008: Image Processing, 8 pages, (2008).

Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).

Gjertsson, K., et. al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.

Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.

Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).

(56) References Cited

OTHER PUBLICATIONS

Gorthi, S. et al., Segmentation of Head and Neck Lymph Node Regions for Radiotherapy Planning Using Active Contour-Based Atlas Registration, IEEE Journal of Selected Topics in Signal Processing, 3(1):135-147 (2009).
Grahovac, M. et al., Machine learning predictive performance evaluation of conventional and fuzzy radiomics in clinical cancer imaging cohorts, Eur. J. Med. Mol. Imaging, 50(6):1607-1620 (2023).
Guan, H. et al., Automatic Hot Spot Detection and Segmentation in Whole Body FDG-PET Images, IEEE International Conference on Image Processing, 4 pages, (2006).
Guimond, A. et al., Average Brain Models: A Convergence Study, Computer Vision and Image Understanding, 77:192-210 (2000).
Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).
He, K. et al., Pelvic Organ Segmentation Using Distinctive Curve Guided Fully Convolutional Networks, IEEE Trans. Med. Imaging, 38(2):585-595 (2019).
Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.
Horikoshi, H. et al., Computer-aided diagnosis system for bone scintigrams from Japanese patients: importance of training database, Annals of Nuclear Medicine, 26(8):622-626 (2012).
Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).
Im, HJ, et al., et al., Current Methods to Define Metabolic Tumor vol. in Positron Emission Tomography: Which One is Better?, Nucl. Med. Mol. Imaging, 52(1):5-15, (2018).
Inoue, T., What cancers can be understood and not known by "PET"?—Effects of PET scanning by site, Medical Note Interview, 4 pages, (2015), retrieved from the internet at: https://medicalnote.jp/contents/150715-000003-CYJIZE.
International Search Report for PCT/EP2020/050132, filed Jan. 6, 2020, 3 pages, mailed (Mar. 12, 2020).
Johnsson, K. et al., Analytical performance of aPROMISE: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.
Johnsson, K., et al., miPSMA Index: Comprehensive and Automated Quantification of 18F-DCFPyL (PyL-PSMA) PET/CT for Prostate Cancer Staging, J Nucl Med., 61: (Supplement 1): 1435, 5 pages, (2020).
Kaboteh R. et al., Progression of bone metastases in patients with prostate cancer—automated detection of new lesions and calculation of bone scan index, EJNMMI Research, 3:64, 6 pages, (2013).
Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).
Kawakami, K. et al., Introduction of bone scintigraphy diagnosis support software "BONENAVI" (Topics), Journal of Nuclear Medicine (Japanese), 63:41-51 (2011).
Kawakami, K., Evaluation of bone metastasis by bone scintigraphy diagnostic support software BONENAVI, Communication of the Imaging Group of the JSRT, 36(1):74-77 (2013).
Kertesz, H. et al., Implementation of a Spatially-Variant and Tissue-Dependent Positron Range Correction for PET/CT Imaging, Front. Physiol., 13:818463 (2022).
Kertesz, H. et al., Positron range in combination with point-spread-function correction: an evaluation of different implementations for [124I]-PET imaging, ENJMMI Phys., 9(1):56 (2022).
Khurshid, Z. et al., Role of textural heterogeneity parameters in patient selection for 177Lu-PSMA therapy via response prediction, Oncotarget., 9(70):33312-33321 (2018).
Kiess, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.
Knutsson, H., and Andersson, M., Morphons: Segmentation using Elastic Canvas and Paint on Priors, IEEE International Conference on Image Processing (ICIP 2005), Genova, Italy, 4 pages (2005).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Krajnc, D. et al., Automated data preparation for in vivo tumor characterization with machine learning, Front. Oncol., 12:1017911 (2022).
Lin, T.Y. et al., Feature Pyramid Networks for object detection, FAIR, 10 pages, (2016), <https://arxiv.org/abs/1612.03144v1>.
Litjens, G. et al., A survey on deep learning in medical image analysis, Medical Image Analysis, 42:60-88, (2017).
Liu, L. et al., Computer-Aided Detection of Prostate Cancer with MRI: Technology and Applications, Acad Radiol. Author manuscript, 50 pages 2016.
Ma, L. et al., Automatic segmentation of the prostate on CT images using deep learning and multi-atlas fusion, Proc. of SPIE vol. 10133:1013320-1-1013320-9 (2017).
Ma, L. et al., Combining Population and Patient-Specific Characteristics for Prostate Segmentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Matsubara, N. et al., A Phase II, Randomized, Open-Label, Multi-arm Study of TAS-115 for Castration-Resistant Prostate Cancer Patients With Bone Metastases, Clinical Genitourinary Cancer, 000(xxx):1-10, (2021).
Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.
Meyer, A., et al., Deep learning algorithm improves identification of men with low-risk prostate cancer using PSMA targeted 99mTc-MIP-1404 SPECT/CT, Journal of Clinical Oncology, 37:(15), (2019).
Nakajima, K. et al., Enhanced diagnostic accuracy for quantitative bone scan using an artificial neural network system: a Japanese multi-center database project, EJNMMI Research, 3:83, 9 pages, (2013).
National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.
Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.
Nickols, N.G., et al., A deep learning algorithm to predict coexisting metastatic disease using intraprostatic [F18]DCFPYL Psma image alone in veterans with prostate cancer, Journal of Clinical Oncology 38, (Supplement 6), 2020.
Nogi, S. et al., Metastatic bone tumor quantified by computer-assisted diagnosis system of bone scintigraphy, Nuclear Medicine in Clinic, 45(3):35-37 (2012).

(56) References Cited

OTHER PUBLICATIONS

Ohlsson, M., et al., Automated decision support for bone scintigraphy, Computer-based medical systems, pp. 1-6, (2009).
Papp, L. et al., Glioma Survival Prediction with Combined Analysis of In Vivo 11C-MET PET Features, Ex Vivo Features, and Patient Features by Supervised Machine Learning, J. Nucl. Med., 59(6):892-899 (2018).
Papp, L. et al., Optimized Feature Extraction for Radiomics Analysis of 18F-FDG PET Imaging, J. Nucl. Med., 60(6):864-872 (2019).
Papp, L. et al., Supervised machine learning enables non-invasive lesion characterization in primary prostate cancer with [68Ga]Ga-PSMA-11 PET/MRI, Eur. J. Nucl. Mol. Imaging, 48(6):1795-1805 (2021).
Partin, A.W. et al., Combination of prostate-specific antigen, clinical stage, and Gleason score to predict pathological stage of localized prostate cancer. A multi-institutional update, JAMA, 277(18):1445-1451 (1997).
Partin, A.W. et al., The use of prostate specific antigen, clinical stage and Gleason score to predict pathological stage in men with localized prostate cancer, J. Urol., 150(1):110-114 (1993).
Paschalis, A. et al., Prostate-specific Membrane Antigen Heterogeneity and DNA Repair Defects in Prostate Cancer, European Urology, 76(4):469-478, (2019).
Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).
Polymeri, E. et al., Analytical validation of an automated method for segmentation of the prostate gland in CT images, Ejnmmi, Eanm '17, 44(Suppl 2):S119-S956, Abstract EP-0641 (2017).
Polymeri, E., et al., Deep learning-based quantification of PET/CT prostate gland uptake: association with overall survival, Clinical Physiology Functional Imaging, DOI: 10.1111/cpf.12611, 40(2):106-113, (2019).
Poulakis, V. et al., Preoperative neural network using combined magnetic resonance imaging variables, prostate specific antigen, and Gleason score to predict prostate cancer recurrence after radical prostatectomy, Eur. Urol., 46(5):571-578 (2004).
Pouliot, F., et al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.
radiologyinfo.org for Patients, Computed Tomography (CT), 2 pages, retrieved Oct. 25, 2017: <https://www.radiologyinfo.org/en/submenu.cfm?pg=ctscan>.
Ren, S., et al., Faster R-CNN: Towards Real-Time Object Detection with Region Proposal Networks, 14 pages, (2015), <http://image-net.org/challenges/LSVRC/2015/results>.
Ronneberger, O., et. al., U-Net: Convolutional Networks for Biomedical Image Segmentation, Springer International Publishing, pp. 234-241, (2015), <http://lmb.informatik.uni-freiburg.de/>. Published online on Nov. 18, 2015.
Rowe, S. P. et al., PET Imaging of prostate-specific membrane antigen in prostate cancer: current state of the art and future challenges, Prostate Cancer and Prostatic Diseases, pp. 1-8 (2016).
Rowe, S. P. et al., PSMA-Based [$^{18}$F]DCFPyL PET/CT Is Superior to Conventional Imaging for Lesion Detection in Patients with Metastatic Prostate Cancer, Mol Imaging Biol, 18:411-419, (2016).
Sabbatini, P. et al., Prognostic Significance of Extent of Disease in Bone in Patients With Androgen-Independent Prostate Cancer, Journal of Clinical Oncology, 17(3):948-957 (1999).
Sadik, M. et al., 3D prostate gland uptake of 18F-choline-association with overall survival in patients with hormone-naïve prostate cancer, The Journal of Nuclear Medicine, 58(Suppl. 1):Abstract 544, 2 pages, (2017).
Sadik, M. et al., A new computer-based decision-support system for the interpretation of bone scans, Nuclear Medicine Communications, 27(5):417-423 (2006).
Sadik, M. et al., Automated 3D segmentation of the prostate gland in CT images—a first step towards objective measurements of prostate uptake in PET and SPECT images, Journal of Nuclear Medicine, 58(1):1074, (2017).
Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).
Sadik, M. et al., Computer-assisted interpretation of planar whole-body bone scans, Journal Nuclear Medicine, 49(12):1958-65, 2008.
Sadik, M. et al., Convolutional neural networks for segmentation of 49 selected bones in CT images show high reproducibility, EJNMMI, EANM '17, 44(Suppl 2):S119-S956, Abstract OP-657 (2017).
Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.
Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).
Sajn, L. et al., Computerized segmentation of whole-body bone scintigrams and its use in automated diagnostics, Computer Methods and Programs in Biomedicine, 80:47-55 (2005).
Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).
Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).
Seifert, R. et al., Second Version of the Prostate Cancer Molecular Imaging Standardized Evaluation Framework Including Response Evaluation for Clinical Trials (PROMISE V2), Eur. Urol., 83(5):405-412 (2023).
Shi, F. et al., Deep learning empowered vol. delineation of whole-body organs-at-risk for accelerated radiotherapy, Nat. Commun., 13(1):6566 (2022).
Sjöstrand K. et al., Statistical regularization of deformation fields for atlas-based segmentation of bone scintigraphy images, MICCAI 5761:664-671 (2009).
Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).
Sjostrand, K., et al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).
Sluimer, I. et al., Toward Automated Segmentation of the Pathological Lung in CT, IEEE Transactions on Medical Imaging, 24(8):1025-1038 (2005).
Teng, C. et al., Head and neck lymph node region delineation using a hybrid image registration method, 3rd IEEE International Symposium on Biomedical Imaging: Nano to Macro, 4 pages, (2006).
Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of SPIE 10135:101351L-1-101351L-6 12 pages, (2017).
Tian, Z., et al., Superpixel-based Segmentation for 3D Prostate MR Images, IEEE Trans Med Imaging, Author manuscript, pp. 558-569, (2016).
Trägårdh, E., et al., RECOMIA—a cloud-based platform for artificial intelligence research in nuclear medicine and radiology, EJNMMI Physics, <https://doi.org/10.1186/s40658-020-00316-9>, 7:51, 12 pages, (2020).

(56) References Cited

OTHER PUBLICATIONS

Ulmert, D. et al., A Novel Automated Platform for Quantifying the Extent of Skeletal Tumour Involvement in Prostate Cancer Patients Using the Bone Scan Index, European Urology, 62(1):78-84 (2012).
US Food and Drug Administration, Clinical Trial Endpoints for the Approval of Cancer Drugs and Biologics, 21 pages, (2018).
Valladares, A. et al., A multi-modality physical phantom for mimicking tumor heterogeneity patterns in PET/CT and PET/MRI, Med. Phys., 49(9):5819-5829 (2022).
Wallis, J.W. et al., Three-dimensional display in nuclear medicine, IEEE Trans Med Imaging, 8(4):297-303, (1989).
Washino, H., Injectable for bone scintigraphy: Technetium hydroxymethylenediphosphonate (99mTc) injection solution (Revised Edition), 9 pages, (2007), retrieved from the internet at:https://rada.or.jp/database/home4/normal/ht-docs/member/synopsis/030292.html#:%7E:text=%E6%A6%82%E8%A6%81).
Wrangsjo, A. et al., Non-rigid Registration Using Morphons, Proceedings of the 14th Scandinavian Conference on Image Analysis (SCIA '05), pp. 501-510 (2005).
Written Opinion for PCT/EP2020/050132, filed Jan. 6, 2020, 11 pages, mailed (Mar. 12, 2020).
Yin, T.-K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).
Chen, X. et al., TensorMask: A Foundation for Dense Object Segmentation, Proceedings of the IEEE/CVF International Conference on Computer Vision (ICCV), 10 pages, (2019).
De Brabandere, B. et al., Semantic Instance Segmentation with a Discriminative Loss Function, arXiv preprint, 10 pages, (2017).
Hatamizadeh, A. et al., UNETR: Transformers for 3D Medical Image Segmentation, Proceedings of the IEEE/CVF Winter Conference on Applications of Computer Vision (WACV), 11 pages, (2022).
Milletari, F. et al., V-Net: Fully Convolutional Neural Networks for Volumetric Medical Image Segmentation, 2016 Fourth International Conference on 3D Vision (3DV), 11 pages, (2016).
Benitez, C.M. et al., Treatment Response Assessment According to Updated PROMISE Criteria in Patients with Metastatic Prostate Cancer Using an Automated Imaging Platform for Identification, Measurement, and Temporal Tracking of Disease, European Urology Oncology, 9 pages, (2024).
Defendant's Memorandum of Law in Support of Motion to Dismiss Second Amended Complaint (including Appendix A thereto), *Progenics Pharmaceuticals Inc. and Exini Diagnostics AB* v. *MIM Software Inc.*, Civil Action No. 1:24-cv-10437-PBS (D. Mass.), Jun. 17, 2024.
Defendant's Motion to Dismiss Second Amended Complaint and Request for Oral Argument, *Progenics Pharmaceuticals Inc. and Exini Diagnostics AB* v. *MIM Software Inc.*, Civil Action No. 1:24-cv-10437-PBS (D. Mass.), Jun. 17, 2024.
Defendant's Reply Memorandum in Support of Motion to Dismiss Second Amended Complaint, *Progenics Pharmaceuticals Inc. and Exini Diagnostics AB* v. *MIM Software Inc.*, Civil Action No. 1:24-cv-10437-PBS (D. Mass.), Jul. 26, 2024.
Plaintiffs' Opposition to Defendant's Motion to Dismiss Second Amended Complaint, *Progenics Pharmaceuticals Inc. and Exini Diagnostics AB* v. *MIM Software Inc.*, Civil Action No. 1:24-cv-10437-PBS (D. Mass.), Jul. 19, 2024.
Plaintiffs' Sur-Reply in Opposition to Defendant's Motion to Dismiss Second Amended Complaint (including Appendix A thereto), *Progenics Pharmaceuticals Inc. and Exini Diagnostics AB* v. *MIM Software Inc.*, Civil Action No. 1:24-cv-10437-PBS (D. Mass.), Aug. 6, 2024.
Second Amended Complaint, *Progenics Pharmaceuticals Inc. and Exini Diagnostics AB* v. *MIM Software Inc.*, Civil Action No. 1:24-cv-10437-PBS (D. Mass.), Apr. 5, 2024.
Afshar-Oromieh, A. et al., Radiation dosimetry of (68)Ga-PSMA-11 (HBED-CC) and preliminary evaluation of optimal imaging timing, Eur. J. Nucl. Med. Mol. Imaging, 43(9):1611-1620 (2016).
Gandaglia, G. et al., Distribution of metastatic sites in patients with prostate cancer: A population-based analysis, Prostate, 74(2):210-216 (2014).
Giesel, F.L. et al., (18)F-Labelled PSMA-1007 shows similarity in structure, biodistribution and tumour uptake to the theragnostic compound PSMA-617, Eur. J. Nucl. Med. Mol. Imaging, 43(10):1929-1930 (2016).
Greenspan, H. et al., Deep Learning in Medical Imaging: Overview and Future Promise of an Exciting New Technique, IEEE Transactions on Medical Imaging, 35(5):1153-1159 (2016).
Guntur, A.R. and Rosen, C.J., Bone as an endocrine organ, Endocr. Pract., 18(5):758-762 (2012).
Kaur, D. and Kaur, Y., Various Image Segmentation Techniques: A Review, International Journal of Computer Science and Mobile Computing, 3(5):809-814 (2014).
Pizzuto, D.A. et al., The central zone has increased 68Ga-PSMA-11 uptake: "Mickey Mouse ears" can be hot on 68Ga-PSMA-11 PET, Eur. J. Nucl. Med. Mol. Imaging, 45(8):1335-1343 (2018).
Seifert, S. et al., Hierarchical parsing and semantic navigation of full body CT data, Medical Imaging 2009: Image Processing, Proceedings of SPIE vol. 7259, 8 pages, (2009).
Sharma, N. and Aggarwal, L.M., Automated medical image segmentation techniques, J. Med. Phys., 35(1):3-14 (2010).
Shen, D. et al., Deep Learning in Medical Image Analysis, Annu. Rev. Biomed. Eng., 19:221-248 (2017).
Weineisen, M. et al., 68Ga- and 177Lu-Labeled PSMA I&T: Optimization of a PSMA-Targeted Theranostic Concept and First Proof-of-Concept Human Studies, J. Nucl. Med., 56(8):1169-1176 (2015).
Iandola, F.N. et al., SqueezeNet: AlexNet-level accuracy with 50x fewer parameters and <0.5MB model size, arXiv, 13 pages, (2016).
Kumar, A. et al., Designing user interfaces to enhance human interpretation of medical content-based image retrieval: application to PET-CT images, Int. J. Comput. Assist. Radiol. Surg., 8(6):1003-1014 (2013).
Mata, C. et al., ProstateAnalyzer: GUI in Medical Domain with Management of DICOM Images of Prostate Cancer (PCa), 1 page, (2012).
Nitta, S. et al., Assisted Diagnosis System by Automatic Extraction of Tumor Candidate Areas from PET/CT Images, Medical Imaging Technology, 24(3):181-190 (2006). English translation included.
Petition for Inter Partes Review of U.S. Pat. No. 10,665,346, *MIM Software Inc.* v. *Progenics Pharmaceuticals, Inc.*, Inter Partes Review No. IPR2025-00630, Feb. 21, 2025.
Petition for Inter Partes Review of U.S. Pat. No. 11,424,035, *MIM Software Inc.* v. *Progenics Pharmaceuticals, Inc.*, Inter Partes Review No. IPR2025-00725, Mar. 14, 2025.
Petition for Inter Partes Review of U.S. Pat. No. 11,894,141, *MIM Software Inc.* v. *Progenics Pharmaceuticals, Inc.*, Inter Partes Review No. IPR2025-00726, Mar. 14, 2025.
Petition for Inter Partes Review of U.S. Pat. No. 11,941,817, *MIM Software Inc.* v. *EXINI Diagnostics AB.*, Inter Partes Review No. IPR2025-00827, Apr. 4, 2025.
Roman-Jimenez, G. et al., Detection of bladder metabolic artifacts in (18)F-FDG PET imaging, Comput. Biol. Med., 71:77-85 (2016).
Saha, M. et al., An Advanced Deep Learning Approach for Ki-67 Stained Hotspot Detection and Proliferation Rate Scoring for Prognostic Evaluation of Breast Cancer, Sci. Rep., 7(1):3213 (2017).

1000

1010 — PET [F18]DCFPyL (PyL) CT

1012 — Find Anatomical Context

1014 — Measure PET Image

1016

1018a    1018b 1020a    1020b    1020c

SYSTEMS AND METHODS FOR PLATFORM AGNOSTIC WHOLE BODY IMAGE SEGMENTATION

CROSS-REFERENCE TO RELATED APPLICATIONS

This application is a divisional of U.S. Non-Provisional application Ser. No. 18/127,991, filed Mar. 29, 2023 (now U.S. Pat. No. 11,941,817), which is a divisional of U.S. Non-Provisional application Ser. No. 16/734,599 (now U.S. Pat. No. 11,657,508), filed Jan. 6, 2020, which claims priority to and benefit of U.S. Provisional Application No. 62/789,155, filed Jan. 7, 2019, U.S. Provisional Application No. 62/837,941, filed Apr. 24, 2019, U.S. Provisional Application No. 62/863,608, filed Jun. 19, 2019, U.S. Provisional Application No. 62/870,210, filed Jul. 3, 2019, U.S. Provisional Application No. 62/907,158, filed Sep. 27, 2019, U.S. Provisional Application No. 62/934,305, filed Nov. 12, 2019, the content of each of which is hereby incorporated by reference in its entirety.

FIELD OF THE INVENTION

This invention relates generally to methods, systems, and architectures for automated analysis of medical images. More particularly, in certain embodiments, the invention relates to automated identification of one or more particular regions of interest (e.g., corresponding to specific organs or tissue) within images of a subject.

BACKGROUND OF THE INVENTION

Targeted image analysis involves the use of radiolabeled small molecules that bind to specific receptors, enzymes and proteins in the body that are altered during the evolution of disease. After administration to a patient, these molecules circulate in the blood until they find their intended target. The bound radiopharmaceutical remains at the site of disease, while the rest of the agent clears from the body. The radioactive portion of the molecule serves as a beacon so that an image may be obtained depicting the disease location and concentration using commonly available nuclear medicine cameras, known as single-photon emission computerized tomography (SPECT) or positron emission tomography (PET) cameras, found in most hospitals throughout the world. Physicians can then use this information to determine the presence and the extent of disease in a patient. The physician can use this information to provide a recommended course of treatment to the patient and to track the progression of disease.

There are a variety of software-based analytical techniques available for analysis and enhancement of PET and SPECT images that can be used by a radiologist or physician. There are also a number of radiopharmaceuticals available for imaging particular kinds of cancer. Imaging agents used in the art include, among others include, without limitation $^{18}F$—NaF, $^{11}C$-Choline, 2-deoxy-2 [18F] fluoro-d-glucose (FDG), and the like. For example, the small molecule diagnostic 1404 targets the extracellular domain of prostate specific membrane antigen (PSMA), a protein amplified on the surface of >95% of prostate cancer cells and a validated target for the detection of primary and metastatic prostate cancer. 1404 is labeled with technetium-99m, a gamma-emitter isotope that is widely available, relatively inexpensive, facilitates efficient preparation, and has spectrum characteristics attractive for nuclear medicine imaging applications.

Another example radiopharmaceutical is PyL™ (also known as [$^{18}F$]DCFPyL, and 18F-PyL), which is a clinical-stage, fluorinated PSMA-targeted PET imaging agent for prostate cancer. A proof-of-concept study published in the April 2016 issue of the Journal of Molecular Imaging and Biology demonstrated that PET imaging with PyL™ showed high levels of PyL™ uptake in sites of putative metastatic disease and primary tumors, suggesting the potential for high sensitivity and specificity in detecting prostate cancer.

An oncologist may use images from a targeted PET or SPECT study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the PET or SPECT images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results.

If an imaging study shows that the patient has a particular disease or condition (e.g., cancer), the physician discusses various treatment options, including surgery, as well as risks of doing nothing or adopting a watchful waiting or active surveillance approach, rather than having surgery.

There are limitations associated with this process, both from the perspective of the physician and from the perspective of the patient. While the radiologist's report is certainly helpful, the physician must ultimately rely on her experience in formulating an assessment and recommendation for her patient. Furthermore, the patient must place a great deal of trust in his physician. The physician may show the patient his PET/SPECT images and may tell the patient a numerical risk associated with various treatment options or likelihood of a particular prognosis, but the patient may very well struggle to make sense of this information. Moreover, the patient's family will likely have questions, particularly if cancer is diagnosed but the patient opts not to have surgery. The patient and/or his family members may search online for supplemental information and may become misinformed about risks of the diagnosed condition. A difficult ordeal may become more traumatic.

Thus, there remains a need for systems and methods for improved automated analysis of medical imaging studies and communication of those results, diagnoses, prognoses, treatment recommendations, and associated risks to a patient. Of particular need is an image analysis system to consistently, efficiently, and accurately detect anatomical regions, including soft tissue organs, in the entire body.

SUMMARY OF THE INVENTION

Presented herein are systems and methods that provide for automated analysis of three-dimensional (3D) medical images of a subject in order to automatically identify specific 3D volumes within the 3D images that correspond to specific anatomical regions e.g., organs and/or tissue). Notably, the image analysis approaches described herein are not limited to a single particular organ or portion of the body. Instead, they are robust and widely applicable, providing for consistent, efficient, and accurate detection of anatomical regions, including tissue and/or organs, in the entire body. In certain embodiments, the accurate identification of one or more such volumes is used to automatically determine quantitative metrics that represent uptake of radiopharmaceuticals in particular organs and/or tissue regions. These uptake metrics can be used to assess disease state in a subject, determine a prognosis for a subject, and/or determine efficacy of a treatment modality.

The capability of the approaches described herein to handle 3D images is an important advantage over certain other image analysis that only identify 2D regions in 2D images. For example, one approach relevant for cancer detection, EXINI Diagnostics AB's Bone Scan Index (BSI) software, detects regions of suspected bone cancer (see also U.S. Pat. No. 8,855,387, issued Oct. 7, 2014). However, the BSI analysis is carried out on two-dimensional scintigraphy images, as opposed to on three dimensional images.

Moreover, with the increase in the choices of imaging agents available to a physician to detect cancer, there remains a need for software with utility in analyzing images from any variety of imaging agents, using multiple detection modalities (SPECT/CT, PET/CT, and the like). Functional images such as SPECT and PET provide detailed and specific information on biological processes in the body, but their potential is only realized when combined with a detailed anatomical map so that function can be localized to individual organs and structures. Although CT and MRI provide detailed anatomical information, conventional (e.g., manual) identification of organs and structures is difficult, subjective and time consuming, making certain assessment infeasible without computer support. Accordingly, by providing platform agnostic image analysis approaches that allow for accurate and robust image segmentation applicable to a variety of imaging modalities, the systems and methods described herein facilitate image analysis of particular relevance to cancer detection, diagnosis, staging, and the like.

For example, the full body segmentation approaches described herein allow for automated analysis of combinations of anatomical and functional images in order to accurately identify and grade cancerous lesions within a subject. In particular, a PET/CT composite image can be acquired for a subject following administration of a radiopharmaceutical, such as a PSMA binding agent like PyL™. The automated, machine learning-based segmentation approaches described herein are used to identify, within the CT image of the PET/CT composite, target volumes of interest (VOIs) representing target tissue regions where cancerous lesions may be found. For example, a skeletal VOI corresponding to a graphical representation of one or more bones of the subject may be identified. Once the skeletal VOI is identified in the anatomical, CT, image, it can be mapped to the PET image to identify a corresponding skeletal volume therein. The corresponding skeletal volume in the PET image is then analyzed to detect one or more localized regions of relatively high intensity, referred to as hotspots. These hotspots correspond, physically, to local regions of increased radiopharmaceutical accumulation and, accordingly, prospective cancerous lesions.

In certain embodiments, the ability to accurately and rapidly perform full body segmentation via the approaches described herein is leveraged to provide a useful and uniform scale on which to evaluate and/or measure radiopharmaceutical uptake levels in physical lesions corresponding to detected hotspots (e.g., to thereby grade expression levels of particular biomolecules, such as PSMA). In particular, in addition to detecting target VOIs corresponding to specific target tissue regions in which cancerous lesions may occur, additional target VOIs corresponding to reference tissue regions are also detected. These reference VOIs are also mapped to the PET image, to identify corresponding reference volumes therein. Measures of intensity, such as a mean, peak, maximum, etc., within these reference volumes are then computed and used as reference points against which to evaluate intensities of individual detected hotspots and convert them to index values on the scale.

For example, in certain embodiments, an aorta and a liver VOI, corresponding to a representation of a portion of an aorta and liver, respectively, are identified within the anatomical image and mapped to the functional image to identify corresponding reference volumes therein. Intensity levels of each of these reference volumes are determined (e.g., as a mean, median, peak, etc. of intensities of voxels within each reference volume), and assigned corresponding index levels on a scale. Then, for each particular individual hotspot, a hotspot intensity level is determined (e.g., similarly, as a mean, median, peak, etc. of voxel intensities within the detected hotspot). A corresponding individual hotspot index value is then determined based individual hotspot intensity level, the aorta reference intensity level, and the liver reference intensity level. This approach provides a standardized scale on which to evaluate and measure uptake associated with hotspots across different images. This allows, for example, for comparison of multiple images obtained for a single subject at different time points, as well as comparison between images of different subjects.

In certain embodiments, individual hotspot indices are used to compute an overall index for the subject and/or particular target tissue region analyzed for presence of cancerous lesions. The overall index can serve as an indicator of disease severity and/or risk, for example by reflecting a total lesion volume within a particular target tissue region, with the weighting based on the hotspot index values for the individual detected hotspots to account for radiopharmaceutical uptake within the lesions. For example, a PSMA weighted total lesion volume within a skeletal volume can be computed as a weighted sum of individual detected hotspot volumes weighted by their corresponding index values. Such an index may reflect a level and/or aggressiveness of metastasis into bone.

Volumes corresponding to other tissue regions may be similarly identified and used to determine overall index values. For example, lymph node volumes may also be used to assess severity of metastases. Volumes corresponding to tissue regions where localized disease is initially found may also be identified and analyzed to detect lesions. For example, a prostate volume may be used to assess prostate cancer severity at its initial stages. Likewise, breast volumes representing breast tissue regions and lung volumes representing lung tissue regions can be used for assessment of localized breast and lung cancers, respectively.

According, by providing for full body segmentation and automated image-based analysis of cancerous lesions throughout various relevant target tissue regions throughout a subject's body, the AI-based systems and methods described herein allow for analysis of a variety of cancers at various stages. The techniques can be used to identify and stage localized disease in relevant tissue regions such as the prostate, for example for early stage screening and monitoring, as well as to monitor regions such as bone and lymph nodes for metastasis as disease progresses. As such, the approaches described herein provide a complete set of tools for automated image-based detection of cancer, and tracking disease evolution, progression, and response to treatment.

In one aspect, the invention is directed to a method for automatically processing a 3D image to identify 3D volumes within the 3D image that correspond to particular target tissue regions, the method comprising: (a) receiving, by a processor of a computing device, a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) automatically identifying, by the processor, using one or more machine learning modules (e.g., wherein at least one of the one or more machine learning modules is a Convolutional Neural Network (CNN) module) for each of a plurality of target tissue regions, a corresponding target volume of interest (VOI) within the 3D anatomical image; (c) determining, by the processor, a 3D segmentation map representing a plurality of 3D segmentation masks, each 3D segmentation mask representing a particular identified target VOI (e.g., automatically, digitally stitching together the plurality of 3D segmentation masks to form the 3D segmentation map); and (d) storing and/or providing for display and/or further processing, the 3D segmentation map.

In certain embodiments, the 3D anatomical image is a full body image.

In certain embodiments, step (c) comprises digitally stitching together the plurality of 3D segmentation masks to form the 3D segmentation map {e.g., by creating an initially empty image volume (e.g., initializing all voxel values to zero) and then inserting labels from each segmentation mask into the image volume [e.g., by mapping labeled (e.g., as representing a particular target tissue region as determined by a machine learning module) voxels of input images to one or machine learning modules to voxels of the image volume (e.g., so as to match voxels of the image volume to voxels of the input images that represent a same physical location, thereby labeling voxels of the image volume correctly)]}.

In certain embodiments, step (b) comprises, for at least one specific target tissue region: determining, using a first module (e.g., a localization module)(e.g., a first machine learning module), an initial VOI within the 3D anatomical image, the initial VOI corresponding to an anatomical region (e.g., a group of related tissue, such as a pelvic region, a chest region, a head and/or neck region, and the like) containing the specific target tissue region (e.g., wherein the initial VOI excludes more voxels of the 3D anatomical image than it includes; e.g., wherein the initial VOI includes less than 25% of the voxels of the 3D anatomical image; e.g., wherein a majority of voxels within the initial VOI represent physical volumes within the anatomical region); and identifying, using a second module (e.g., a segmentation module)(e.g., a second machine learning module), the target VOI corresponding to the specific target tissue region within the initial VOI.

In certain embodiments, the second module is a CNN module that implements a CNN.

In certain embodiments, the first module is a CNN module that implements a CNN to perform a coarse segmentation to automatically identify the initial VOI corresponding to the anatomical region containing the specific target tissue region [e.g., by automatically identifying a graphical representation of a group of related tissue within the anatomical image (e.g., and, subsequently, determining the initial VOI as a rectangular region (e.g., rectangular prism or rectangular box) entirely enclosing the identified graphical representation of the group of related tissue)][e.g., by, for each of one or more particular tissue regions anticipated to be located within the anatomical region, automatically identifying a corresponding VOI in the anatomical image (e.g., via the coarse segmentation), e.g., and determining the initial VOI as a rectangular region entirely enclosing all of the identified VOIs corresponding to the particular tissue regions].

In certain embodiments, the first module receives a sub-sampled [e.g., by a factor of two or more (e.g., four) along one or more dimensions] version of the anatomical image as input and identifies the initial VOI using the sub-sampled version of the anatomical image [e.g., and wherein the second module receives a full resolution version of the anatomical image, cropped to the initial VOI (e.g., such that the first module operates on an lower resolution image that represents a larger physical volume than the second module, while the second module operates on a higher resolution image but representing a smaller physical volume)].

In certain embodiments, the first module is a first CNN module and the second module is a second CNN module, and wherein the first CNN module comprises additional filters in order to account for increased variability in image size with respect to the second CNN module.

In certain embodiments, the 3D anatomical image is a full body image and step (b) comprises: automatically determining, using one or more localization modules implementing machine learning technique(s) (e.g., wherein each localization module is a CNN module that implements a CNN), a plurality of initial VOIs within the 3D anatomical image, each initial VOI corresponding to a particular anatomical region (e.g., a group of related tissue, such as a pelvic region, a chest region, a head and/or neck region, a spine region, an upper body region, a lower body region, etc.) and in which an associated subset of the target VOIs are located; and for each initial VOI, automatically identifying, using one or more segmentation modules implementing machine learning technique(s) (e.g., wherein each segmentation module is a CNN module that implements a CNN) the associated subset of target VOIs.

In certain embodiments, the plurality of initial VOIs comprises one or more members selected from the group consisting of: a pelvic region initial VOI corresponding to a pelvic region of the subject (e.g., wherein the subset of target VOIs located in the pelvic region initial VOI comprise one or more target VOIs corresponding to target tissue regions selected from the group consisting of a left and/or right ilium, a sacrum, and a coccyx); a spine region initial VOI corresponding to a spine of the subject (e.g., wherein the subset of target VOIs located in the pelvic region initial VOI comprise one or more target VOIs corresponding to target tissue regions selected from the group consisting of a thoracic vertebra, a lumber vertebra, and a sternum); a left upper body region initial VOI corresponding to a left side of the subject's upper body (e.g., wherein the subset of target VOIs located in the pelvic region initial VOI comprise one or more target VOIs corresponding to target tissue regions selected from the group consisting of one or more left rib(s), a left scapula, and a left clavicle); and a right upper body region initial VOI corresponding to a right side of the subject's upper body (e.g., wherein the subset of target VOIs located in the pelvic region initial VOI comprise one or more target VOIs corresponding to target tissue regions selected from the group consisting of one or more right rib(s), a right scapula, and a right clavicle).

In certain embodiments, the method comprises: (e) receiving, by the processor, a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more of the target tissue regions of the subject]; and (f) identifying, by the processor, within the 3D functional image, one or more 3D volume(s), each corresponding to an identified target VOI, using the 3D segmentation map (e.g., by mapping 3D segmentation masks of the 3D segmentation map to the 3D functional image).

In certain embodiments, the method comprises: (g) determining, by the processor, a cancer status [(e.g., a prostate cancer status; e.g., a metastatic cancer status (e.g., metastatic cancer, including, e.g., metastatic prostate cancer, breast cancer, lung cancer, colon cancer, skin cancer, etc.)] for the subject (e.g., using intensities of voxels within the functional image and the one or more identified 3D volumes)(e.g., based on detected lesions) [e.g., a likelihood of the subject having and/or developing prostate cancer and/or a particular stage of prostate cancer (e.g., metastatic prostate cancer)] [e.g., a likelihood of the subject having and/or developing a metastatic cancer (including, e.g., metastatic prostate cancer, breast cancer, lung cancer, colon cancer, skin cancer, etc.)].

In certain embodiments, the method comprises performing steps (a)-(g) repeatedly for a plurality of anatomical and corresponding functional images collected at different time points to determine, at each time point, a cancer status of the subject, thereby tracking cancer status over time (e.g., to evaluate disease progression and/or treatment efficacy).

In certain embodiments, the method comprises (e.g., prior to step (g)): (h) automatically adjusting, by the processor, intensities of voxels of the 3D functional image to correct for background uptake (e.g., of the radiopharmaceutical) in one or more background tissue regions (e.g., correcting for uptake of the radiopharmaceutical that occurs in the one or more background tissue regions under normal circumstances, and which is not necessarily indicative of presence of cancerous lesions).

In certain embodiments, the target tissue regions comprise the one or more background tissue regions and step (h) comprises: using the 3D segmentation map to identify, within the 3D functional image, one or more 3D background tissue volume(s), each corresponding a particular background tissue region (e.g., by mapping 3D segmentation masks of the 3D segmentation map to the 3D functional image); and adjusting intensities of voxels of the 3D functional image based on intensities of voxels within the 3D background tissue volumes (e.g., by using intensities of voxels within the 3D background tissue volumes to estimate a contribution to intensities outside of the 3D background tissue volumes).

In certain embodiments, the one or more background tissue regions comprise one or more members selected from the group consisting of: a bladder (e.g., a urinary bladder), a kidney, a duodenum, a small intestine, a spleen, a liver, a pancreas, a stomach, an adrenal gland, a rectum, and testes.

In certain embodiments, the method comprises: (i) automatically detecting, by the processor, one or more hotspots within the 3D functional image determined to represent lesions based on intensities of voxels within the 3D functional image [e.g., based on a comparison of intensities within the 3D functional image with a threshold value (e.g., wherein the 3D functional image is a 3D PET image and the threshold is a particular standard uptake value (SUV) level)] (e.g., and also based on the one or more 3D volumes identified within the 3D functional image).

In certain embodiments, step (i) comprises using one or more thresholds [e.g., comparing intensities of voxels in the 3D functional image with the one or more thresholds (e.g., wherein the one or more thresholds comprises a plurality of region-specific thresholds, each used for a specific sub-set of the one or more 3D volumes identified within the 3D functional image)].

In certain embodiments, step (i) comprises applying one or more filters to the 3D functional image [e.g., as in a blob detection technique; e.g., wherein the one or more filters comprises one or more Gaussian filters (e.g., a high pass Gaussian filter and a low pass Gaussian filter, as in a Difference of Gaussians approach); e.g., wherein the one or more filters comprises a Laplacian filter (e.g., as in a Laplacian of a Gaussian technique); e.g., wherein different filter kernels are used for different sub-sets of the one or more 3D volumes identified within the 3D functional image].

In certain embodiments, step (i) comprises using a combination of two or more techniques for identification of hotspots in different sub-sets of the one or more 3D volumes identified within the 3D functional image [e.g., using a first filtering approach (e.g., as in paragraphs above) for a first sub-set of the one or more 3D volumes and using a second filtering approach for a second sub-set; e.g., using thresholding approach (e.g., as in paragraphs above) for a first sub-set of the one or more 3D volumes and using a filtering approach (e.g., as in paragraphs above) for a second sub-set of the one or more 3D volumes].

In certain embodiments, step (i) comprises detecting an initial set of hotspots and, for at least a portion of the hotspots of the initial set, classifying each hotspot of at least a portion of the detected hotspots as either a cancerous lesion or not a cancerous lesion (e.g., as noise) [e.g., using a machine learning module; e.g., based on a shape and/or location of the hotspot (e.g., in combination with anatomical knowledge; e.g., wherein the location includes an identification of a particular target tissue region corresponding to the 3D volume in which the hotspot is located and/or a relative position of the hotspot within the particular target tissue region); e.g., and removing hotspots classified as not a cancerous lesion from the initial set, thereby obtaining a final set of hotspots determined to represent lesions].

In certain embodiments, the target tissue regions comprise one or more background tissue regions and the method comprises: using the 3D segmentation map to identify, within the 3D functional image, one or more 3D background tissue volume(s), each corresponding a particular background tissue region (e.g., a background tissue region in which significant radiopharmaceutical uptake occurs under normal circumstances and is not necessarily indicative of presence of cancerous lesions)(e.g., by mapping 3D segmentation masks of the 3D segmentation map to the 3D functional image); and excluding voxels of the 3D within the 3D background tissue from the voxels used to automatically detect the one or more hotspots at step (i).

In certain embodiments, the method comprises using the one or more detected hotspots (e.g., intensities of the one or more detected hotspots) to determine a cancer status for the subject.

In certain embodiments, the target tissue regions comprise one or more reference tissue regions and the method comprises: using the 3D segmentation map to identify, by the processor, within the 3D functional image, one or more 3D reference volume(s), each corresponding to a particular reference tissue region; determining, by the processor, one or more reference intensity values, each associated with a particular 3D reference volume of the one or more 3D reference volume(s) and corresponding to a measure of (e.g., an average/mean, a median, a maximum, etc.) intensity within the particular 3D reference volume; determining, by the processor, one or more individual hotspot intensity values, each associated with a particular hotspot of at least a portion of the detected one or more hotspots and corresponding to a measure of (e.g., an average/mean, a median, a maximum, etc.) intensity of the particular hotspot; and determining, by the processor, one or more individual hotspot index values using the one or more individual hotspot intensity values and the one or more reference intensity values [e.g., wherein each individual hotspot index value is associated with a particular hotspot of the at least a portion of the detected one or more hotspots and determined using (e.g., based on a comparison between) (i) the individual hotspot intensity value associated with the particular hotspot and (ii) the one or more reference intensity values].

In certain embodiments, the determining the one or more individual hotspot index values comprises mapping each of the one or more reference intensity values to a corresponding reference index value on a scale and, for each individual hotspot intensity value, using the reference intensity values and corresponding reference index values to interpolate a corresponding individual hotspot index value.

In certain embodiments, the reference tissue regions comprise one or more members selected from the group consisting of: a liver, an aorta (e.g., a thoracic aorta portion; e.g., an abdominal aorta portion), and a parotid gland.

In certain embodiments, a first reference intensity value (i) is a blood reference intensity value associated with a 3D reference volume corresponding to an aorta portion, and (ii) maps to a first reference index value; a second reference intensity value (i) is a liver reference intensity value associated with a 3D reference volume corresponding to a liver, and (ii) maps to a second reference index value; and the second reference intensity value is greater than the first reference intensity value and the second reference index value is greater than the first reference index value.

In certain embodiments, the reference intensity values comprises a maximum reference intensity value that maps to a maximum reference index value, and hotspots having associated hotspot intensity values greater than the maximum reference intensity value are assigned hotspot index values equal to the maximum reference index value.

In certain embodiments, the method comprises determining, by the processor, an overall index value indicative of a cancer status of the subject using at least a portion of the one or more hotspot index values.

In certain embodiments, the overall index value is determined as a weighted sum of at least a portion [e.g., located within a 3D volume of the functional image that corresponds to a skeletal region of the subject; e.g., located within a 3D volume of the functional image that corresponds to a lymph region of the subject] of the individual hotspot index values [e.g., wherein each hotspot index value in the sum is weighted by a measure of size (e.g., 3D volume; e.g., average diameter) of the associated hotspot].

In certain embodiments, the overall index value is associated with a particular target tissue region corresponding to a particular target VOI identified within the anatomical image; and the overall index value is determined using hotspot index values of a subset of hotspots located within a particular 3D volume in the 3D functional image that corresponds to the particular identified target VOI [e.g., and wherein the overall index value is computed as a weighted sum of the hotspot index values of the subset of hotspots (e.g., wherein the weighted sum is normalized by an estimated volume of the particular target tissue region (e.g., computed as a volume of the particular 3D volume in the function image and/or a volume of the particular target VOI))].

In certain embodiments, the particular target tissue region is selected from the group consisting of: a skeletal region comprising one or more bones of the subject, a lymph region, and a prostate region.

In certain embodiments, the 3D anatomical image is an x-ray computed tomography (CT) image, and the 3D functional image is a 3D single photon emission computed tomography (SPECT) image.

In certain embodiments, the 3D anatomical image is an x-ray computed tomography (CT) image, and the 3D functional image is a 3D positron emission tomography (PET) image.

In certain embodiments, the 3D PET image of the subject is obtained following administration to the subject of a radiopharmaceutical comprising a prostate-specific membrane antigen (PSMA) binding agent.

In certain embodiments, the radiopharmaceutical comprises [18F]DCFPyL.

In certain embodiments, step (b) comprises cropping, by the processor, the 3D anatomical image to remove voxels representing air [e.g., to create a cropped anatomical image, and using the cropped anatomical image to identify the one or more target VOIs (e.g., using the cropped anatomical image is used as input to one or more machine learning modules, as opposed to the original size 3D anatomical image)].

In certain embodiments, the target tissue regions comprise one or more members selected from the group consisting of: a left hip bone, a right hip bone, a sacrum and coccyx region, a left clavicle, a right clavicle, a left rib, a right rib, a left scapula, a right scapula, a sternum, a lumbar vertebra, a thoracic vertebra, a skull, a cervical vertebra, a left femur, a right femur, a left humerus, a right humerus, a prostate, a urinary bladder, a rectum, a left gluteus maximus, a right gluteus maximus, an aorta (e.g., a thoracic aorta portion; e.g., an abdominal aorta portion), a left kidney, a right kidney, a liver, a left lung, a right lung, a spleen, a ventricle, a left adrenal gland, a right adrenal gland, a gallbladder, a brain, a pancreas, a heart, a mandible, a left bronchi, a right bronchi, a trachea, a left common iliac artery, a right common iliac artery, and a parotid gland.

In certain embodiments, one or more of the target tissue regions comprise one or more specific bones selected from the group consisting of: a left clavicle, a right clavicle, a left femur, a right femur, a left fibula, a right fibula, a left hip bone, a right hip bone, a left humerus, a right humerus, a mandible, a left patella, a right patella, left radius, a right radius, a left tibia, a right tibia, a left ulna, a right ulna, a left rib (e.g., a first left rib, a second left rib, a third left rib, a fourth left rib, a fifth left rib, a sixth left rib, a seventh left rib, an eighth left rib, a ninth left rib, a tenth left rib, an eleventh left rib, a twelfth left rib), a right rib (e.g., a first right rib, a second right rib, a third right rib, a fourth right rib, a fifth right rib, a sixth right rib, a seventh right rib, an eighth right rib, a ninth right rib, a tenth right rib, an eleventh right rib, a twelfth right rib), a sacrum and coccyx (e.g., a combined sacrum and coccyx region; e.g., a sacrum and a coccyx individually, so as to distinguish between the two), a left scapula, a right scapula, a skull, sternum, a vertebrae region [e.g., a cervical vertebrae region, comprising one or more (e.g., up to all) cervical vertebrae; e.g., a lumber vertebrae region, comprising one or more (e.g., up to all) lumbar vertebrae; e.g., a thoracic vertebrae region, comprising one or more (e.g., up to all) thoracic vertebrae], and an individual vertebra [e.g., e.g., an individual cervical vertebra (e.g., a first cervical vertebra, a second cervical vertebra, a third cervical vertebra, a fourth cervical vertebra, a fifth cervical vertebra, a sixth cervical vertebra, a seventh cervical vertebra); e.g., an individual lumbar vertebra (e.g., a first lumbar vertebra, a second lumbar vertebra, a third lumbar vertebra, a fourth lumbar vertebra, a fifth lumbar vertebra, a sixth lumbar vertebra); e.g., an individual thoracic vertebra (e.g., a first thoracic vertebra, a second thoracic vertebra, a third thoracic vertebra, a fourth, thoracic vertebra, a fifth thoracic vertebra, a sixth thoracic vertebra, a seventh thoracic vertebra, an eighth thoracic vertebra, a ninth thoracic vertebra, a tenth thoracic vertebra, an eleventh thoracic vertebra, an twelfth thoracic vertebra)].

In certain embodiments, one or more of the target tissue regions comprise one or more specific bones selected from the group consisting of: a left clavicle, a right clavicle, a left hip bone, a right hip bone, a left rib (e.g., a first left rib, a second left rib, a third left rib, a fourth left rib, a fifth left rib, a sixth left rib, a seventh left rib, an eighth left rib, a ninth left rib, a tenth left rib, an eleventh left rib, a twelfth left rib), a right rib (e.g., a first right rib, a second right rib, a third right rib, a fourth right rib, a fifth right rib, a sixth right rib, a seventh right rib, an eighth right rib, a ninth right rib, a tenth right rib, an eleventh right rib, a twelfth right rib), a sacrum and coccyx (e.g., a combined sacrum and coccyx region; e.g., a sacrum and a coccyx individually, so as to distinguish between the two), a left scapula, a right scapula, a sternum, a vertebrae region [e.g., a cervical vertebrae region, comprising one or more (e.g., up to all) cervical vertebrae; e.g., a lumber vertebrae region, comprising one or more (e.g., up to all) lumbar vertebrae; e.g., a thoracic vertebrae region, comprising one or more (e.g., up to all) thoracic vertebrae], and an individual vertebra [e.g., an individual lumbar vertebra (e.g., a first lumbar vertebra, a second lumbar vertebra, a third lumbar vertebra, a fourth lumbar vertebra, a fifth lumbar vertebra); e.g., an individual thoracic vertebra (e.g., a first thoracic vertebra, a second thoracic vertebra, a third thoracic vertebra, a fourth, thoracic vertebra, a fifth thoracic vertebra, a sixth thoracic vertebra, a seventh thoracic vertebra, an eighth thoracic vertebra, a ninth thoracic vertebra, a tenth thoracic vertebra, an eleventh thoracic vertebra, an twelfth thoracic vertebra)].

In certain embodiments, one or more of the target tissue regions comprise one or more soft-tissue regions (e.g., organs) selected from the group consisting of: a left adrenal gland, a right adrenal gland, an aorta (e.g., a thoracic aorta portion; e.g., an abdominal aorta portion), a brain, a left bronchi, a right bronchi, a gallbladder, a left gluteus maximus, a right gluteus maximus, a heart, a left common iliac artery, a right common iliac artery, a left kidney, a right kidney, a liver, a left lung, a right lung, a pancreas, a prostate, a rectum, a spleen, a trachea, a urinary bladder, a ventricle, and a parotid gland.

In certain embodiments, the one or more target tissue regions comprise one or more soft-tissue regions (e.g., organs) selected from the group consisting of: a gallbladder, a left kidney, a right kidney, a liver, a left lung, a right lung, a prostate, and a urinary bladder.

In certain embodiments, the target tissue regions comprise one or more bone regions, each corresponding to a specific bone [e.g., where the target tissue regions comprise at least a portion of (e.g., up to all) the bones listed in paragraphs above and one or more soft tissue regions, each corresponding to a specific soft-tissue region [e.g., where the target tissue regions comprise at least a portion of (e.g., up to all) the soft-tissue regions listed in paragraphs above.

In another aspect, the invention is directed to a method for automatically processing 3D images to automatically identify cancerous lesions within a subject, the method comprising: (a) receiving, by a processor of a computing device, a 3D anatomical image of a subject obtained using an anatomical imaging modality [e.g., x-ray computed tomography (CT); e.g., magnetic resonance imaging (MRI); e.g., ultrasound], wherein the 3D anatomical image comprises a graphical representation of tissue (e.g., soft-tissue and/or bone) within the subject; (b) automatically identifying, by the processor, using one or more machine learning modules (e.g., wherein at least one of the one or more machine learning modules is a Convolutional Neural Network (CNN) module), for each of a plurality of target tissue regions, a corresponding target volume of interest (VOI) within the 3D anatomical image; (c) determining, by the processor, a 3D segmentation map representing a plurality of 3D segmentation masks, each 3D segmentation mask representing a particular identified target VOI (e.g., automatically, digitally stitching together the plurality of 3D segmentation masks to form the 3D segmentation map); (d) receiving, by the processor, a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more of the target tissue regions of the subject]; (e) identifying, within the 3D functional image, one or more 3D volume(s), each corresponding to an identified target VOI, using the 3D segmentation map (e.g., by mapping 3D segmentation masks of the 3D segmentation map to the 3D functional image); and (f) automatically detecting, by the processor, within at least a portion of the one or more 3D volumes identified within the 3D functional image, one or more hotspots determined to represent lesions based on intensities of voxels within the 3D functional image [e.g., based on a comparison of intensities within the 3D functional image with a threshold value (e.g., wherein the 3D functional image is a 3D PET image and the threshold is a particular standard uptake value (SUV) level)].

In certain embodiments, the method comprises using, by the processor, the one or more detected hotspots (e.g., intensities of the one or more detected hotspots) to determine a cancer status for the subject.

In certain embodiments, the target tissue regions comprise one or more reference tissue regions and wherein the method comprises: using the 3D segmentation map to identify, by the processor, within the 3D functional image, one or more 3D reference volume(s), each corresponding to a particular reference tissue region; determining one or more reference intensity values, each associated with a particular 3D reference volume of the one or more 3D reference volume(s) and corresponding to a measure of (e.g., an average/mean, a median, a maximum, etc.) intensity within the particular 3D reference volume; determining, by the processor, one or more individual hotspot intensity values, each associated with a particular hotspot of at least a portion of the detected one or more hotspots and corresponding to a measure of (e.g., an average/mean, a median, a maximum, etc.) intensity of the particular hotspot; and determining, by the processor, one or more individual hotspot index values using the one or more individual hotspot intensity values and the one or more reference intensity values [e.g., wherein each individual hotspot index value is associated with a particular hotspot of the at least a portion of the detected one or more hotspots and determined using (e.g., based on a comparison between) (i) the individual hotspot intensity value associated with the particular hotspot and (ii) the one or more reference intensity values].

In certain embodiments, the reference tissue regions comprise one or more members selected from the group consisting of: a liver, an aorta (e.g., a thoracic aorta portion; e.g., an abdominal aorta portion), and a parotid gland.

In certain embodiments, the method comprises determining, by the processor, an overall index value indicative of a cancer status of the subject using at least a portion of the one or more hotspot index values.

In certain embodiments, the overall index value is determined as a weighted sum of at least a portion [e.g., located within a 3D volume of the functional image that corresponds to a skeletal region of the subject; e.g., located within a 3D volume of the functional image that corresponds to a lymph region of the subject] of the individual hotspot index values [e.g., wherein each hotspot index value in the sum is weighted by a measure of size (e.g., 3D volume; e.g., average diameter) of the associated hotspot].

In certain embodiments, the 3D anatomical image is an x-ray computed tomography (CT) image, and the 3D functional image is a 3D positron emission tomography (PET) image.

In certain embodiments, the 3D PET image of the subject is obtained following administration to the subject of a radiopharmaceutical comprising a prostate-specific membrane antigen (PSMA) binding agent.

In certain embodiments, the radiopharmaceutical comprises [18F]DCFPyL.

In another aspect, the invention is directed to a method for automatically processing 3D images to identify, and measure uptake of radiopharmaceutical in, cancerous lesions (e.g., metastases) within a subject having or at risk for a cancer (e.g., prostate cancer, breast cancer, lung cancer; e.g., a metastatic cancer, such as metastatic prostate cancer, metastatic breast cancer, metastatic lung cancer), the method comprising: (a) receiving, by a processor of a computing device, a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) automatically identifying, by the processor, using one or more machine learning modules (e.g., wherein at least one of the machine learning modules is a Convolutional Neural Network (CNN) module), within the 3D anatomical image: a first skeletal volume comprising a graphical representation of one or more bones of the subject; a first aorta volume comprising a graphical representation of at least a portion of an aorta of the subject; and a first liver volume comprising a graphical representation of a liver of the subject; (c) determining, by the processor, a 3D segmentation map representing a plurality of 3D segmentation masks, including a skeletal mask representing the identified first skeletal volume, an aorta mask representing the identified first aorta volume, and a liver mask representing the identified first liver volume; (d) receiving, by the processor, a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more bones, an aorta portion, and/or a liver of the subject]; (e) automatically identifying, within the 3D functional image, using the 3D segmentation map (e.g., by mapping the 3D segmentation masks of the 3D segmentation map to the 3D functional image): a second skeletal volume corresponding to the first identified skeletal volume, within the 3D anatomical image; a second aorta volume corresponding to the first aorta volume, identified within the 3D anatomical image; and a second liver volume corresponding to the first liver volume, identified within the 3D anatomical image; (f) automatically detecting, by the processor, within the second skeletal volume, one or more hotspots determined to represent lesions based on intensities of voxels within the second skeletal volume (e.g., the one or more hotspots corresponding to localized regions of relatively high intensity, e.g., identified based on a comparison of intensities of voxels located within the second skeletal volume with a threshold value); and (g) determining, by the processor, for each of the one or more detected hotspots, an individual hotspot index (e.g., indicative of a measure of radiopharmaceutical uptake in the lesions represented by the detected hotspot) value by: determining an aorta reference intensity level based on a measure (e.g., a mean, a maximum, a median, etc.) of intensity of voxels within the second aorta volume; determining a liver reference intensity level based on a measure (e.g., a mean, a maximum, a median, etc.) of intensity of voxels within the second liver volume; and for each individual detected hotspot: determining a corresponding individual hotspot intensity level based on a measure (e.g., a mean, a maximum, a median, etc.) of intensity of voxels of the detected hotspot; and determining a corresponding individual hotspot index level from the individual hotspot intensity level, the aorta reference intensity level, and the liver reference intensity level.

In certain embodiments, the method comprises determining, by the processor, an overall index value indicative of a cancer status of the subject based on the individual hotspot index values of at least a portion of the one or more detected hotspots.

In certain embodiments, the subject has or is at risk for prostate cancer.

In certain embodiments, step (b) comprises automatically identifying, within the 3D anatomical image, a first prostate volume comprising a graphical representation of a prostate of the subject, the 3D segmentation map determined at step (c) further includes a prostate mask representing the identified first prostate volume, step (e) comprises automatically identifying, within the 3D functional image, a second prostate volume corresponding to the first identified prostate volume, within the 3D anatomical image, step (f) comprises automatically detecting one or more hotspots in the second prostate volume, and the method further comprises: determining, by the processor, (i) an overall bone index value indicative of a lesion content (e.g., and severity) in the one or more bones of the subject based on the individual hotspot index values of at least a portion of the one or more detected hotspots located in the second skeletal volume and (ii) an overall prostate index value indicative of a lesion content (e.g., and severity) in the prostate of the subject based on the individual hotspot index values of at least a portion of the one or more detected hotspots located in the second prostate volume.

In certain embodiments, the subject has or is at risk for metastatic cancer (e.g., metastatic prostate cancer, metastatic breast cancer, metastatic lung cancer, and other metastatic bone cancers).

In another aspect, the invention is directed to a method for automatically processing a set of full body 3D anatomical images of varying sizes to automatically identify, within each 3D anatomical image, a plurality of 3D volumes that correspond to particular target tissue regions, the method comprising: (a) receiving, by a processor of a computing device, the set of 3D anatomical images of one or more subject(s) obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within each of the one or more subject(s), wherein the set of 3D anatomical images has a mean x-dimension, a mean y-dimension, and a mean z-dimension, at least one of which (the mean x-, mean y-, or mean z-dimension) having a standard deviation at least 3% of the corresponding mean [e.g., at least one of which (the mean x-, mean y-, or mean z-dimension) having a relative standard deviation of at least 3%, at least 5%, at least 10%, at least 15%, or at least 20%]; and (b) automatically determining, by the processor, using a localization module that implements a CNN, within each image of the set of 3D anatomical images, at least one initial VOI corresponding to a particular anatomical region (e.g., a group of related tissue, such as a pelvic region and a spin region) that comprises one or more particular associated target tissue regions (e.g., one or more specific bones, e.g., one or more specific organs), thereby identifying at least one initial VOI for the corresponding 3D anatomical image; and (c) for each initial VOI, automatically identifying, by the processor, using one or more segmentation modules each implementing a CNN, for each of the one or more particular target tissue regions associated with the particular anatomical region to which the initial VOI corresponds, a corresponding target VOI (e.g., a graphical representation of the particular target tissue region).

In another aspect, the invention is directed to a system for automatically processing a 3D image to identify 3D volumes within the 3D image that correspond to particular target tissue regions, the system comprising: a processor of a computing device; and a memory having instructions stored thereon, wherein the instructions, when executed by the processor, cause the processor to: (a) receive a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) automatically identify, using one or more machine learning modules (e.g., wherein at least one of the one or more machine learning modules is a Convolutional Neural Network (CNN) module), for each of a plurality of target tissue regions, a corresponding target volume of interest (VOI) within the 3D anatomical image; (c) determine 3D segmentation map representing a plurality of 3D segmentation masks, each 3D segmentation mask representing a particular identified target VOI (e.g., automatically, digitally stitching together the plurality of 3D segmentation masks to form the 3D segmentation map); and (d) store and/or provide the 3D segmentation map for display and/or further processing.

In certain embodiments, the 3D anatomical image is a full body image.

In certain embodiments, at step (c) the instructions cause the processor to digitally stitch together the plurality of 3D segmentation masks to form the 3D segmentation map {e.g., by creating an initially empty image volume (e.g., initializing all voxel values to zero) and then inserting labels from each segmentation mask into the image volume [e.g., by mapping labeled (e.g., as representing a particular target tissue region as determined by a machine learning module) voxels of input images to one or machine learning modules to voxels of the image volume (e.g., so as to match voxels of the image volume to voxels of the input images that represent a same physical location, thereby labeling voxels of the image volume correctly)]}.

In certain embodiments, at step (b), the instructions cause the processor to, for at least one specific target tissue region: determine, using a first module (e.g., a localization module) (e.g., a first machine learning module), an initial VOI within the 3D anatomical image, the initial VOI corresponding to an anatomical region (e.g., a group of related tissue, such as a pelvic region, a chest region, a head and/or neck region, and the like) containing the specific target tissue region (e.g., wherein the initial VOI excludes more voxels of the 3D anatomical image than it includes; e.g., wherein the initial VOI includes less than 25% of the voxels of the 3D anatomical image; e.g., wherein a majority of voxels within the initial VOI represent physical volumes within the anatomical region); and identify, using a second module (e.g., a segmentation module)(e.g., a second machine learning module), the target VOI corresponding to the specific target tissue region within the initial VOI.

In certain embodiments, the second module is a CNN module that implements a CNN.

In certain embodiments, the first module is a CNN module that implements a CNN to perform a coarse segmentation to automatically identify the initial VOI corresponding to the anatomical region containing the specific target tissue region [e.g., by automatically identifying a graphical representation of a group of related tissue within the anatomical image (e.g., and, subsequently, determining the initial VOI as a rectangular region (e.g., rectangular prism or rectangular box) entirely enclosing the identified graphical representation of the group of related tissue)][e.g., by, for each of one or more particular tissue regions anticipated to be located within the anatomical region, automatically identifying a corresponding VOI in the anatomical image (e.g., via the coarse segmentation), e.g., and determining the initial VOI as a rectangular region entirely enclosing all of the identified VOIs corresponding to the particular tissue regions].

In certain embodiments, the first module receives a sub-sampled [e.g., by a factor of two or more (e.g., four) along one or more dimensions] version of the anatomical image as input and identifies the initial VOI using the sub-sampled version of the anatomical image [e.g., and wherein the second module receives a full resolution version of the anatomical image, cropped to the initial VOI (e.g., such that the first module operates on an lower resolution image that represents a larger physical volume than the second module, while the second module operates on a higher resolution image but representing a smaller physical volume)].

In certain embodiments, the first module is a first CNN module and the second module is a second CNN module, and wherein the first CNN module comprises additional filters in order to account for increased variability in image size with respect to the second CNN module.

In certain embodiments, the 3D anatomical image is a full body image and wherein, at step (b), the instructions cause the processor to: automatically determine, using one or more localization modules implementing machine learning technique(s) (e.g., wherein each localization module is a CNN module that implements a CNN), a plurality of initial VOIs within the 3D anatomical image, each initial VOI corresponding to a particular anatomical region (e.g., a group of related tissue, such as a pelvic region, a chest region, a head and/or neck region, a spine region, an upper body region, a lower body region, etc.) and in which an associated subset of the target VOIs are located; and for each initial VOI, automatically identify, using one or more segmentation modules implementing machine learning technique(s) (e.g., wherein each segmentation module is a CNN module that implements a CNN) the associated subset of target VOIs.

In certain embodiments, the plurality of initial VOIs comprises one or more members selected from the group consisting of: a pelvic region initial VOI corresponding to a pelvic region of the subject (e.g., wherein the subset of target VOIs located in the pelvic region initial VOI comprise one or more target VOIs corresponding to target tissue regions selected from the group consisting of a left and/or right ilium, a sacrum, and a coccyx); a spine region initial VOI corresponding to a spine of the subject (e.g., wherein the subset of target VOIs located in the pelvic region initial VOI comprise one or more target VOIs corresponding to target tissue regions selected from the group consisting of a thoracic vertebra, a lumber vertebra, and a sternum); a left upper body region initial VOI corresponding to a left side of the subject's upper body (e.g., wherein the subset of target VOIs located in the pelvic region initial VOI comprise one or more target VOIs corresponding to target tissue regions selected from the group consisting of one or more left rib(s), a left scapula, and a left clavicle); and a right upper body region initial VOI corresponding to a right side of the subject's upper body (e.g., wherein the subset of target VOIs located in the pelvic region initial VOI comprise one or more target VOIs corresponding to target tissue regions selected from the group consisting of one or more right rib(s), a right scapula, and a right clavicle).

In certain embodiments, the instructions cause the processor to: (e) receive a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more of the target tissue regions of the subject]; and (f) identify, within the 3D functional image, one or more 3D volume(s), each corresponding to an identified target VOI, using the 3D segmentation map (e.g., by mapping 3D segmentation masks of the 3D segmentation map to the 3D functional image).

In certain embodiments, the instructions cause the processor to: (g) determine a cancer status [(e.g., a prostate cancer status; e.g., a metastatic cancer status (e.g., metastatic cancer, including, e.g., metastatic prostate cancer, breast cancer, lung cancer, colon cancer, skin cancer, etc.)] for the subject (e.g., using intensities of voxels within the functional image and the one or more identified 3D volumes)(e.g., based on detected lesions) [e.g., a likelihood of the subject having and/or developing prostate cancer and/or a particular stage of prostate cancer (e.g., metastatic prostate cancer)] [e.g., a likelihood of the subject having and/or developing a metastatic cancer (including, e.g., metastatic prostate cancer, breast cancer, lung cancer, colon cancer, skin cancer, etc.)].

In certain embodiments, the instructions cause the processor to perform steps (a)-(g) repeatedly for a plurality of anatomical and corresponding functional images collected at different time points to determine, at each time point, a cancer status of the subject, thereby tracking cancer status over time (e.g., to evaluate disease progression and/or treatment efficacy).

In certain embodiments, the instructions cause the processor to (e.g., prior to step (g)): (h) automatically adjust intensities of voxels of the 3D functional image to correct for background uptake (e.g., of the radiopharmaceutical) in one or more background tissue regions (e.g., correcting for uptake of the radiopharmaceutical that occurs in the one or more background tissue regions under normal circumstances, and which is not necessarily indicative of presence of cancerous lesions).

In certain embodiments, the target tissue regions comprise the one or more background tissue regions and wherein, at step (h), the instructions cause the processor to: use the 3D segmentation map to identify, within the 3D functional image, one or more 3D background tissue volume(s), each corresponding a particular background tissue region (e.g., by mapping 3D segmentation masks of the 3D segmentation map to the 3D functional image); and adjust intensities of voxels of the 3D functional image based on intensities of voxels within the 3D background tissue volumes (e.g., by using intensities of voxels within the 3D background tissue volumes to estimate a contribution to intensities outside of the 3D background tissue volumes).

In certain embodiments, the one or more background tissue regions comprise one or more members selected from the group consisting of: a bladder (e.g., a urinary bladder), a kidney, a duodenum, a small intestine, a spleen, a liver, a pancreas, a stomach, an adrenal gland, a rectum, and testes.

In certain embodiments, the instructions cause the processor to: (i) automatically detect one or more hotspots within the 3D functional image determined to represent lesions based on intensities of voxels within the 3D functional image [e.g., based on a comparison of intensities within the 3D functional image with a threshold value (e.g., wherein the 3D functional image is a 3D PET image and the threshold is a particular standard uptake value (SUV) level)] (e.g., and also based on the one or more 3D volumes identified within the 3D functional image).

In certain embodiments, at step (i), the instructions cause the processor to use one or more thresholds [e.g., comparing intensities of voxels in the 3D functional image with the one or more thresholds (e.g., wherein the one or more thresholds comprises a plurality of region-specific thresholds, each used for a specific sub-set of the one or more 3D volumes identified within the 3D functional image)].

In certain embodiments, at step (i), the instructions cause the processor to apply one or more filters to the 3D functional image [e.g., as in a blob detection technique; e.g., wherein the one or more filters comprises one or more Gaussian filters (e.g., a high pass Gaussian filter and a low pass Gaussian filter, as in a Difference of Gaussians approach); e.g., wherein the one or more filters comprises a Laplacian filter (e.g., as in a Laplacian of a Gaussian technique); e.g., wherein different filter kernels are used for different sub-sets of the one or more 3D volumes identified within the 3D functional image].

In certain embodiments, at step (i), the instructions cause the processor to use a combination of two or more techniques for identification of hotspots in different sub-sets of the one or more 3D volumes identified within the 3D functional image [e.g., using a first filtering approach (e.g., as in paragraphs above) for a first sub-set of the one or more 3D volumes and using a second filtering approach for a second sub-set; e.g., using thresholding approach (e.g., as in paragraphs above) for a first sub-set of the one or more 3D volumes and using a filtering approach (e.g., as in paragraphs above) for a second sub-set of the one or more 3D volumes].

In certain embodiments, at step (i), the instructions cause the processor to detect an initial set of hotspots and, for at least a portion of the hotspots of the initial set, classify each hotspot of at least a portion of the detected hotspots as either a cancerous lesion or not a cancerous lesion (e.g., as noise)[e.g., using a machine learning module; e.g., based on a shape and/or location of the hotspot (e.g., in combination with anatomical knowledge; e.g., wherein the location includes an identification of a particular target tissue region corresponding to the 3D volume in which the hotspot is located and/or a relative position of the hotspot within the particular target tissue region); e.g., and removing hotspots classified as not a cancerous lesion from the initial set, thereby obtaining a final set of hotspots determined to represent lesions].

In certain embodiments, the target tissue regions comprise one or more background tissue regions and the instructions cause the processor to: use the 3D segmentation map to identify, within the 3D functional image, one or more 3D background tissue volume(s), each corresponding a particular background tissue region (e.g., a background tissue region in which significant radiopharmaceutical uptake occurs under normal circumstances and is not necessarily indicative of presence of cancerous lesions)(e.g., by mapping 3D segmentation masks of the 3D segmentation map to the 3D functional image); and exclude voxels of the 3D within the 3D background tissue from the voxels used to automatically detect the one or more hotspots at step (i).

In certain embodiments, the instructions cause the processor to use the one or more detected hotspots (e.g., intensities of the one or more detected hotspots) to determine a cancer status for the subject.

In certain embodiments, the target tissue regions comprise one or more reference tissue regions and the instructions cause the processor to: use the 3D segmentation map to identify, within the 3D functional image, one or more 3D reference volume(s), each corresponding to a particular reference tissue region; determine one or more reference intensity values, each associated with a particular 3D reference volume of the one or more 3D reference volume(s) and corresponding to a measure of (e.g., an average/mean, a median, a maximum, etc.) intensity within the particular 3D reference volume; determine one or more individual hotspot intensity values, each associated with a particular hotspot of at least a portion of the detected one or more hotspots and corresponding to a measure of (e.g., an average/mean, a median, a maximum, etc.) intensity of the particular hotspot; and determine one or more individual hotspot index values using the one or more individual hotspot intensity values and the one or more reference intensity values [e.g., wherein each individual hotspot index value is associated with a particular hotspot of the at least a portion of the detected one or more hotspots and determined using (e.g., based on a comparison between) (i) the individual hotspot intensity value associated with the particular hotspot and (ii) the one or more reference intensity values].

In certain embodiments, the instructions cause the processor to determine the one or more individual hotspot index values by mapping each of the one or more reference intensity values to a corresponding reference index value on a scale and, for each individual hotspot intensity value, using the reference intensity values and corresponding reference index values to interpolate a corresponding individual hotspot index value.

In certain embodiments, the reference tissue regions comprise one or more members selected from the group consisting of: a liver, an aorta (e.g., a thoracic aorta portion; e.g., an abdominal aorta portion), and a parotid gland.

In certain embodiments, a first reference intensity value (i) is a blood reference intensity value associated with a 3D reference volume corresponding to an aorta portion, and (ii) maps to a first reference index value; a second reference intensity value (i) is a liver reference intensity value associated with a 3D reference volume corresponding to a liver, and (ii) maps to a second reference index value; and the second reference intensity value is greater than the first reference intensity value and the second reference index value is greater than the first reference index value.

In certain embodiments, the reference intensity values comprises a maximum reference intensity value that maps to a maximum reference index value, and wherein hotspots having associated hotspot intensity values greater than the maximum reference intensity value are assigned hotspot index values equal to the maximum reference index value.

In certain embodiments, the instructions cause the processor to determine an overall index value indicative of a cancer status of the subject using at least a portion of the one or more hotspot index values.

In certain embodiments, the overall index value is determined as a weighted sum of at least a portion [e.g., located within a 3D volume of the functional image that corresponds to a skeletal region of the subject; e.g., located within a 3D volume of the functional image that corresponds to a lymph region of the subject] of the individual hotspot index values [e.g., wherein each hotspot index value in the sum is weighted by a measure of size (e.g., 3D volume; e.g., average diameter) of the associated hotspot].

In certain embodiments, the overall index value is associated with a particular target tissue region corresponding to a particular target VOI identified within the anatomical image; and the overall index value is determined using hotspot index values of a subset of hotspots located within a particular 3D volume in the 3D functional image that corresponds to the particular identified target VOI [e.g., and wherein the overall index value is computed as a weighted sum of the hotspot index values of the subset of hotspots (e.g., wherein the weighted sum is normalized by an estimated volume of the particular target tissue region (e.g., computed as a volume of the particular 3D volume in the function image and/or a volume of the particular target VOI))].

In certain embodiments, the particular target tissue region is selected from the group consisting of: a skeletal region comprising one or more bones of the subject, a lymph region, and a prostate region.

In certain embodiments, the 3D anatomical image is an x-ray computed tomography (CT) image, and the 3D functional image is a 3D single photon emission computed tomography (SPECT) image.

In certain embodiments, the 3D anatomical image is an x-ray computed tomography (CT) image, and the 3D functional image is a 3D positron emission tomography (PET) image.

In certain embodiments, the 3D PET image of the subject is obtained following administration to the subject of a radiopharmaceutical comprising a prostate-specific membrane antigen (PSMA) binding agent.

In certain embodiments, the radiopharmaceutical comprises [18F]DCFPyL.

In certain embodiments, at step (b), the instructions cause the processor to crop the 3D anatomical image to remove voxels representing air [e.g., to create a cropped anatomical image, and using the cropped anatomical image to identify the one or more target VOIs (e.g., using the cropped anatomical image is used as input to one or more machine learning modules, as opposed to the original size 3D anatomical image)].

In certain embodiments, the target tissue regions comprise one or more members selected from the group consisting of: a left hip bone, a right hip bone, a sacrum and coccyx region, a left clavicle, a right clavicle, a left rib, a right rib, a left scapula, a right scapula, a sternum, a lumbar vertebra, a thoracic vertebra, a skull, a cervical vertebra, a left femur, a right femur, a left humerus, a right humerus, a prostate, a urinary bladder, a rectum, a left gluteus maximus, a right gluteus maximus, an aorta (e.g., a thoracic aorta portion; e.g., an abdominal aorta portion), a left kidney, a right kidney, a liver, a left lung, a right lung, a spleen, a ventricle, a left adrenal gland, a right adrenal gland, a gallbladder, a brain, a pancreas, a heart, a mandible, a left bronchi, a right bronchi, a trachea, a left common iliac artery, a right common iliac artery, and a parotid gland.

In certain embodiments, one or more of the target tissue regions comprise one or more specific bones selected from the group consisting of: a left clavicle, a right clavicle, a left femur, a right femur, a left fibula, a right fibula, a left hip bone, a right hip bone, a left humerus, a right humerus, a mandible, a left patella, a right patella, left radius, a right radius, a left tibia, a right tibia, a left ulna, a right ulna, a left rib (e.g., a first left rib, a second left rib, a third left rib, a fourth left rib, a fifth left rib, a sixth left rib, a seventh left rib, an eighth left rib, a ninth left rib, a tenth left rib, an eleventh left rib, a twelfth left rib), a right rib (e.g., a first right rib, a second right rib, a third right rib, a fourth right rib, a fifth right rib, a sixth right rib, a seventh right rib, an eighth right rib, a ninth right rib, a tenth right rib, an eleventh right rib, a twelfth right rib), a sacrum and coccyx (e.g., a combined sacrum and coccyx region; e.g., a sacrum and a coccyx individually, so as to distinguish between the two), a left scapula, a right scapula, a skull, sternum, a vertebrae region [e.g., a cervical vertebrae region, comprising one or more (e.g., up to all) cervical vertebrae; e.g., a lumber vertebrae region, comprising one or more (e.g., up to all) lumbar vertebrae; e.g., a thoracic vertebrae region, comprising one or more (e.g., up to all) thoracic vertebrae], and an individual vertebra [e.g., e.g., an individual cervical vertebra (e.g., a first cervical vertebra, a second cervical vertebra, a third cervical vertebra, a fourth cervical vertebra, a fifth cervical vertebra, a sixth cervical vertebra, a seventh cervical vertebra); e.g., an individual lumbar vertebra (e.g., a first lumbar vertebra, a second lumbar vertebra, a third lumbar vertebra, a fourth lumbar vertebra, a fifth lumbar vertebra, a sixth lumbar vertebra); e.g., an individual thoracic vertebra (e.g., a first thoracic vertebra, a second thoracic vertebra, a third thoracic vertebra, a fourth, thoracic vertebra, a fifth thoracic vertebra, a sixth thoracic vertebra, a seventh thoracic vertebra, an eighth thoracic vertebra, a ninth thoracic vertebra, a tenth thoracic vertebra, an eleventh thoracic vertebra, an twelfth thoracic vertebra)].

In certain embodiments, one or more of the target tissue regions comprise one or more specific bones selected from the group consisting of: a left clavicle, a right clavicle, a left hip bone, a right hip bone, a left rib (e.g., a first left rib, a second left rib, a third left rib, a fourth left rib, a fifth left rib, a sixth left rib, a seventh left rib, an eighth left rib, a ninth left rib, a tenth left rib, an eleventh left rib, a twelfth left rib), a right rib (e.g., a first right rib, a second right rib, a third right rib, a fourth right rib, a fifth right rib, a sixth right rib, a seventh right rib, an eighth right rib, a ninth right rib, a tenth right rib, an eleventh right rib, a twelfth right rib), a sacrum and coccyx (e.g., a combined sacrum and coccyx region; e.g., a sacrum and a coccyx individually, so as to distinguish between the two), a left scapula, a right scapula, a sternum, a vertebrae region [e.g., a cervical vertebrae region, comprising one or more (e.g., up to all) cervical vertebrae; e.g., a lumber vertebrae region, comprising one or more (e.g., up to all) lumbar vertebrae; e.g., a thoracic vertebrae region, comprising one or more (e.g., up to all) thoracic vertebrae], and an individual vertebra [e.g., an individual lumbar vertebra (e.g., a first lumbar vertebra, a second lumbar vertebra, a third lumbar vertebra, a fourth lumbar vertebra, a fifth lumbar vertebra); e.g., an individual thoracic vertebra (e.g., a first thoracic vertebra, a second thoracic vertebra, a third thoracic vertebra, a fourth, thoracic vertebra, a fifth thoracic vertebra, a sixth thoracic vertebra, a seventh thoracic vertebra, an eighth thoracic vertebra, a ninth thoracic vertebra, a tenth thoracic vertebra, an eleventh thoracic vertebra, an twelfth thoracic vertebra)].

In certain embodiments, one or more of the target tissue regions comprise one or more soft-tissue regions (e.g., organs) selected from the group consisting of: a left adrenal gland, a right adrenal gland, an aorta (e.g., a thoracic aorta portion; e.g., an abdominal aorta portion), a brain, a left bronchi, a right bronchi, a gallbladder, a left gluteus maximus, a right gluteus maximus, a heart, a left common iliac artery, a right common iliac artery, a left kidney, a right kidney, a liver, a left lung, a right lung, a pancreas, a prostate, a rectum, a spleen, a trachea, a urinary bladder, a ventricle, and a parotid gland.

In certain embodiments, the one or more target tissue regions comprise one or more soft-tissue regions (e.g., organs) selected from the group consisting of: a gallbladder, a left kidney, a right kidney, a liver, a left lung, a right lung, a prostate, and a urinary bladder.

In certain embodiments, the target tissue regions comprise one or more bone regions, each corresponding to a specific bone [e.g., where the target tissue regions comprise at least a portion of (e.g., up to all) the bones listed in paragraphs above and one or more soft tissue regions, each corresponding to a specific soft-tissue region [e.g., where the target tissue regions comprise at least a portion of (e.g., up to all) the soft-tissue regions listed in paragraphs above.

In another aspect, the invention is directed to a system for automatically processing 3D images to automatically identify cancerous lesions within a subject, the system comprising: a processor of a computing device; and a memory having instructions stored thereon, wherein the instructions, when executed by the processor, cause the processor to: (a) receive a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) automatically identify, using one or more machine learning modules (e.g., wherein at least one of the one or more machine learning modules is a Convolutional Neural Network (CNN) module), for each of a plurality of target tissue regions, a corresponding target volume of interest (VOI) within the 3D anatomical image; (c) determine a 3D segmentation map representing a plurality of 3D segmentation masks, each 3D segmentation mask representing a particular identified target VOI (e.g., automatically, digitally stitching together the plurality of 3D segmentation masks to form the 3D segmentation map); (d) receive a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more of the target tissue regions of the subject]; (e) identify, within the 3D functional image, one or more 3D volume(s), each corresponding to an identified target VOI, using the 3D segmentation map (e.g., by mapping 3D segmentation masks of the 3D segmentation map to the 3D functional image); and (f) automatically detect, within at least a portion of the one or more 3D volumes identified within the 3D functional image, one or more hotspots determined to represent lesions based on intensities of voxels within the 3D functional image [e.g., based on a comparison of intensities within the 3D functional image with a threshold value (e.g., wherein the 3D functional image is a 3D PET image and the threshold is a particular standard uptake value (SUV) level)].

In certain embodiments, the instructions cause the processor to use the one or more detected hotspots (e.g., intensities of the one or more detected hotspots) to determine a cancer status for the subject.

In certain embodiments, the target tissue regions comprise one or more reference tissue regions and wherein the instructions cause the processor to: use the 3D segmentation map to identify, within the 3D functional image, one or more 3D reference volume(s), each corresponding to a particular reference tissue region; determine one or more reference intensity values, each associated with a particular 3D reference volume of the one or more 3D reference volume(s) and corresponding to a measure of (e.g., an average/mean, a median, a maximum, etc.) intensity within the particular 3D reference volume; determine one or more individual hotspot intensity values, each associated with a particular hotspot of at least a portion of the detected one or more hotspots and corresponding to a measure of (e.g., an average/mean, a median, a maximum, etc.) intensity of the particular hotspot; and determine one or more individual hotspot index values using the one or more individual hotspot intensity values and the one or more reference intensity values [e.g., wherein each individual hotspot index value is associated with a particular hotspot of the at least a portion of the detected one or more hotspots and determined using (e.g., based on a comparison between) (i) the individual hotspot intensity value associated with the particular hotspot and (ii) the one or more reference intensity values].

In certain embodiments, the reference tissue regions comprise one or more members selected from the group consisting of: a liver, an aorta (e.g., a thoracic aorta portion; e.g., an abdominal aorta portion), and a parotid gland.

In certain embodiments, the instructions cause the processor to determine an overall index value indicative of a cancer status of the subject using at least a portion of the one or more hotspot index values.

In certain embodiments, the overall index value is determined as a weighted sum of at least a portion [e.g., located within a 3D volume of the functional image that corresponds to a skeletal region of the subject; e.g., located within a 3D volume of the functional image that corresponds to a lymph region of the subject] of the individual hotspot index values [e.g., wherein each hotspot index value in the sum is weighted by a measure of size (e.g., 3D volume; e.g., average diameter) of the associated hotspot].

In certain embodiments, the 3D anatomical image is an x-ray computed tomography (CT) image, and the 3D functional image is a 3D positron emission tomography (PET) image.

In certain embodiments, the 3D PET image of the subject is obtained following administration to the subject of a radiopharmaceutical comprising a prostate-specific membrane antigen (PSMA) binding agent.

In certain embodiments, the radiopharmaceutical comprises [18F]DCFPyL.

In another aspect, the invention is directed to a system for automatically processing 3D images to identify, and measure uptake of radiopharmaceutical in, cancerous lesions (e.g., metastases) within a subject having or at risk for a cancer (e.g., prostate cancer, breast cancer, lung cancer; e.g., a metastatic cancer, such as metastatic prostate cancer, metastatic breast cancer, metastatic lung cancer), the system comprising: a processor of a computing device; and a memory having instructions stored thereon, wherein the instructions, when executed by the processor, cause the processor to: (a) receive a 3D anatomical image of a subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (b) automatically identify using one or more machine learning modules (e.g., wherein at least one of the machine learning modules is a Convolutional Neural Network (CNN) module), within the 3D anatomical image: a first skeletal volume comprising a graphical representation of one or more bones of the subject; a first aorta volume comprising a graphical representation of at least a portion of an aorta of the subject; and a first liver volume comprising a graphical representation of a liver of the subject; (c) determine a 3D segmentation map representing a plurality of 3D segmentation masks, including a skeletal mask representing the identified first skeletal volume, an aorta mask representing the identified first aorta volume, and a liver mask representing the identified first liver volume; (d) receive a 3D functional image of the subject obtained using a functional imaging modality [e.g., single-photon emission computed tomography (SPECT); e.g., positron emission tomography (PET)][e.g., wherein the 3D functional image comprises a plurality of voxels, each representing a particular physical volume within the subject and having an intensity value that represents detected radiation emitted from a the particular physical volume, wherein at least a portion of the plurality of voxels of the 3D functional image represent physical volumes within one or more bones, an aorta portion, and/or a liver of the subject]; (e) automatically identify, within the 3D functional image, using the 3D segmentation map (e.g., by mapping the 3D segmentation masks of the 3D segmentation map to the 3D functional image): a second skeletal volume corresponding to the first identified skeletal volume, within the 3D anatomical image; a second aorta volume corresponding to the first aorta volume, identified within the 3D anatomical image; and a second liver volume corresponding to the first liver volume, identified within the 3D anatomical image; (f) automatically detect, within the second skeletal volume, one or more hotspots determined to represent lesions based on intensities of voxels within the second skeletal volume (e.g., the one or more hotspots corresponding to localized regions of relatively high intensity, e.g., identified based on a comparison of intensities of voxels located within the second skeletal volume with a threshold value); and (g) determine, for each of the one or more detected hotspots, an individual hotspot index (e.g., indicative of a measure of radiopharmaceutical uptake in the lesions represented by the detected hotspot) value by: determining an aorta reference intensity level based on a measure (e.g., a mean, a maximum, a median, etc.) of intensity of voxels within the second aorta volume; determining a liver reference intensity level based on a measure (e.g., a mean, a maximum, a median, etc.) of intensity of voxels within the second liver volume; and for each individual detected hotspot: determining a corresponding individual hotspot intensity level based on a measure (e.g., a mean, a maximum, a median, etc.) of intensity of voxels of the detected hotspot; and determining a corresponding individual hotspot index level from the individual hotspot intensity level, the aorta reference intensity level, and the liver reference intensity level.

In certain embodiments, the instructions cause the processor to determine an overall index value indicative of a cancer status of the subject based on the individual hotspot index values of at least a portion of the one or more detected hotspots.

In certain embodiments, the subject has or is at risk for prostate cancer.

In certain embodiments, the instructions cause the processor to: at step (b), automatically identify, within the 3D anatomical image, a first prostate volume comprising a graphical representation of a prostate of the subject; at step (c), include a prostate mask representing the identified first prostate volume in the determined 3D segmentation map; at step (e), automatically identify, within the 3D functional image, a second prostate volume corresponding to the first identified prostate volume, within the 3D anatomical image, at step (f), automatically detect one or more hotspots in the second prostate volume; and determine (i) an overall bone index value indicative of a lesion content (e.g., and severity) in the one or more bones of the subject based on the individual hotspot index values of at least a portion of the one or more detected hotspots located in the second skeletal volume and (ii) an overall prostate index value indicative of a lesion content (e.g., and severity) in the prostate of the subject based on the individual hotspot index values of at least a portion of the one or more detected hotspots located in the second prostate volume.

In certain embodiments, the subject has or is at risk for metastatic cancer (e.g., metastatic prostate cancer, metastatic breast cancer, metastatic lung cancer, and other metastatic bone cancers).

In another aspect, the invention is directed to a system for automatically processing a set of full body 3D anatomical images of varying sizes to automatically identify, within each 3D anatomical image, a plurality of 3D volumes that correspond to particular target tissue regions, the system comprising: a processor of a computing device; and a memory having instructions stored thereon, wherein the instructions, when executed by the processor, cause the processor to: (a) receive the set of 3D anatomical images of one or more subject(s) obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within each of the one or more subject(s), wherein the set of 3D anatomical images has a mean x-dimension, a mean y-dimension, and a mean z-dimension, at least one of which (the mean x-, mean y-, or mean z-dimension) having a standard deviation at least 3% of the corresponding mean [e.g., at least one of which (the mean x-, mean y-, or mean z-dimension) having a relative standard deviation of at least 3%, at least 5%, at least 10%, at least 15%, or at least 20%]; and (b) automatically determine, using a localization module that implements a CNN, within each image of the set of 3D anatomical images, at least one initial VOI corresponding to a particular anatomical region (e.g., a group of related tissue, such as a pelvic region and a spin region) that comprises one or more particular associated target tissue regions (e.g., one or more specific bones, e.g., one or more specific organs), thereby identifying at least one initial VOI for the corresponding 3D anatomical image; and (c) for each initial VOI, automatically identify, using one or more segmentation modules each implementing a CNN, for each of the one or more particular target tissue regions associated with the particular anatomical region to which the initial VOI corresponds, a corresponding target VOI (e.g., a graphical representation of the particular target tissue region).

Features of embodiments described with respect to one aspect of the invention may be applied with respect to another aspect of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which.

Figure 1:
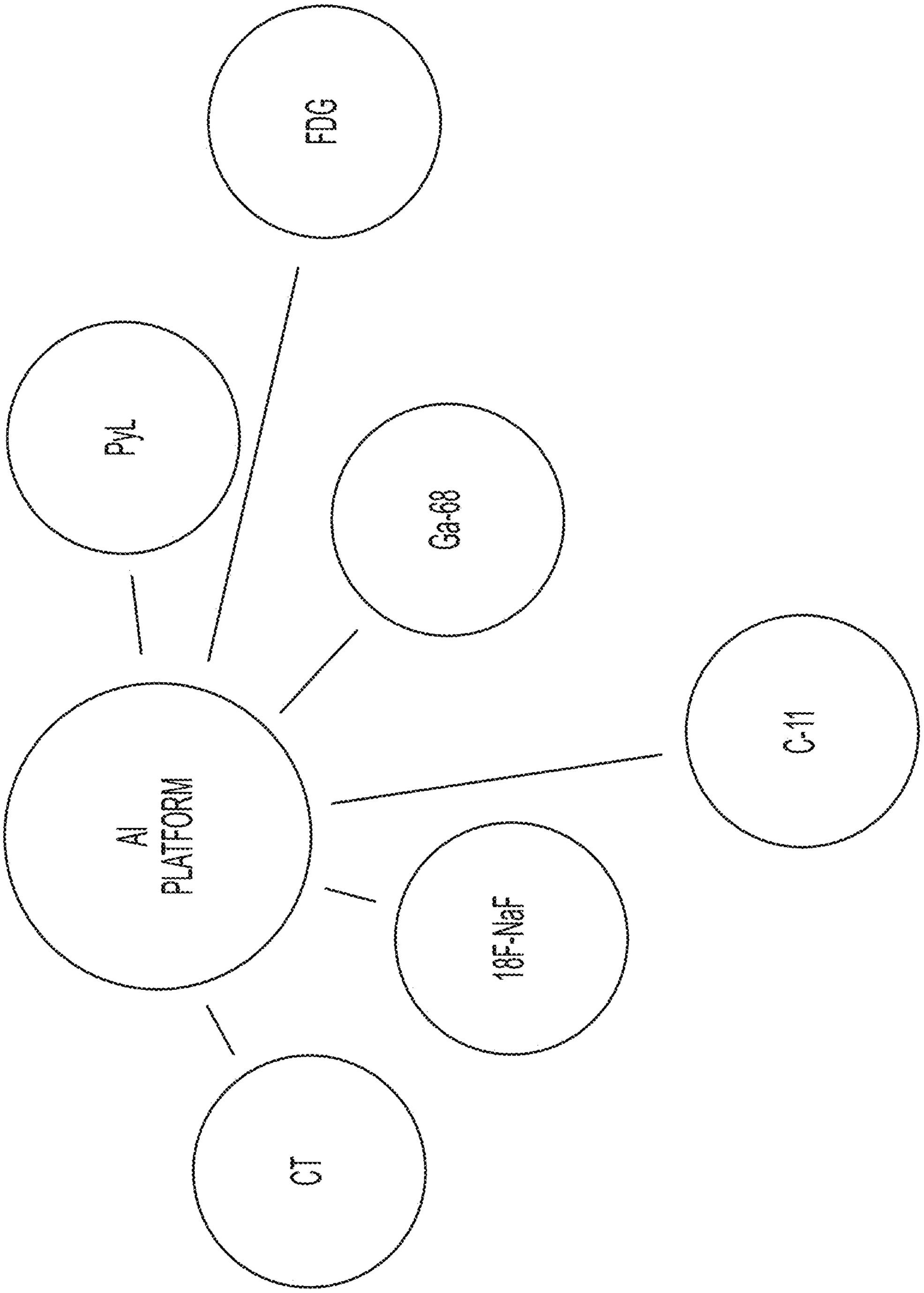
FIG. 1 is a diagram showing integration of various imaging modalities with an artificial intelligence (AI) platform, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

i. Definitions

As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

As used herein, "3D" or "three dimensional" with reference to an "image" means conveying information about three dimensions. A 3D image may be rendered as a dataset in three dimensions and/or may be displayed as a set of two-dimensional representations, or as a three-dimensional representation.

As used herein, an "image"—for example, a 3-D image of a subject—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, a "subject" means a human or other mammal (e.g., rodent (mouse, rat, hamster), pig, cat, dog, horse, primate, rabbit, and the like).

As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

As used herein, the terms "filter", and "filtering", as in a "filtering function" or a "filter", refer to a function that operates on localized portions of an input array (e.g., a multi-dimensional array) of data (e.g., image data, e.g., values computed by a layer of a CNN), referred to herein as "subpatches", computing, for a given subpatch, a response value. In general, a filter is applied in a sliding window fashion across the array to compute a plurality of response values for the array. In particular, for a given multidimensional array, a subpatch of the array can be a rectangular region of the array having a specific size (e.g., having the same number of dimensions as the array). For example, for a 6×3×3 array, a given 3×3×3 subpatch refers to a given 3×3×3 set of adjacent values (e.g., a neighborhood) of the array, such that there are five distinct 3×3×3 subpatches in the 6×3×3 array (each patch shifted one position over along the first dimension).

For example, a filtering function can compute, for a given subpatch of an array, a response value using the values of the subpatch. A filtering function can be applied in a sliding window fashion across an array, computing, for each of a plurality of subpatches of the array, a response value. The computed response values can be stored in an output array such that the positional correspondence between response values and the subpatches of the input array is maintained.

For example, at a first step, beginning with a subpatch in a corner of an input array, a filter can compute a first response value, and store the first response value in a corresponding corner of an output array. In certain embodiments, at a second step, the filter then computes a second response value for a second subpatch, shifted one position over along a specific dimension of the input array. The second response value can be stored in a corresponding position of the output array—that is, shifted one position over along a same dimension of the output array. The step of shifting position of the subpatch, computing a response value, and storing the response value in a corresponding position of the output array can be repeated for the full input array, along each dimension of the input array. In certain embodiments (e.g., a strided filtering approach), the subpatch for which the filter computes a response value is shifted more than one position at a time along a given dimension, such that response values are not computed for every possible subpatch of the input array.

As used herein, the term "convolutional neural network (CNN)" refers to a type of artificial neural network where at least one layer performs one or more filtering functions. As used herein, the term "convolution layer" refers to a layer of a CNN that receives as input an input array and computes an output array, wherein values of the output array are computed by applying one or more filters to the input array. In particular, in certain embodiments, a convolution layer receives as input an input array having n+1 dimensions and produces an output array also having n+1 dimensions. The first n dimensions of input and output arrays operated on by filtering layers of a CNN are referred to herein as "spatial dimensions". The (n+1)th dimension of the input is referred to herein as the "input channel" dimension. The size of the input channel dimension is referred to herein as the "number of input channels". The (n+1)th dimension of the output is referred to herein as the "output channel" dimension. The size of the input channel dimension is referred to herein as the "number of output channels".

In certain embodiments, a convolution layer computes response values by applying a filter that operates on subpatches that are smaller than the input array along the spatial dimensions, but extend across the full output channel dimension. For example, an $N \times M \times L \times K_0$ size input array, has three spatial dimensions and $K_0$ output channels. Filters of a convolution layer may operate on subpatches having sizes of $N_f \times M_f \times L_f \times K_0$, where $N_f \leq N$, $M_f \leq M$ and $L_f \leq L$. Often, a filter of a convolutional layer operates on subpatches having sizes where $N_f < N$, $M_f < M$ and/or $L_f < L$. For example, in certain embodiments, $N_f << N$, $M_f << M$ and/or $L_f << L$.

Accordingly, for each of one or more filters applied by a convolution layer, response values computed by a given filter are stored in a corresponding output channel. Accordingly, a convolution layer that receives an input array having n+1 dimensions computes an output array also having n+1 dimensions, wherein the $(n+1)^{th}$ dimension represents the output channels corresponding to the one or more filters applied by the convolution layer. In this manner, an output array computed by a given convolution layer can be received as input by a subsequent convolution layer.

As used herein, the term "size" in reference to a filter of a convolution layer refers to a size along spatial dimensions of subpatches on which the filter operates (e.g., the subpatch size along the output channel dimension is taken as the full number of output channels). As used herein, the term "size", in reference to a convolution layer, as in "size of a convolution layer" refers to a size of filters of the convolution layer (e.g., each filter of the convolution layer having a same size). In certain embodiments, a filter of a convolution layer has a number of variable parameters that are determined via a machine learning training process. In certain embodiments, the number of parameters of a given filter equals the number of values in a subpatch that the given filter operates on. For example, a size $N_f \times M_f \times L_f$ filter that operates on an input array with $K_0$ output channels has $N_f \times M_f \times L_f \times K_0$ parameters. In certain embodiments, a filter is implemented as an array, and the response value determined by the filter for a given subpatch is computed as a dot product between the filter and the given subpatch.

As used herein, the term "fully convolutional neural network (FCNN)" refers to a CNN wherein each layer of the CNN is a convolution layer.

As used herein, the term "volume", as used in reference to an input or output of a layer of a CNN refers to an input array received or an output array computed by a CNN layer.

As used herein, the term "CNN module" refers to a computer implemented process that implements a specific CNN in order to determine, for a given input, such as an image (e.g., a 2D image; e.g., a 3D image) one or more output values. For example, a CNN module may receive as input a 3D image of a subject (e.g., a CT image; e.g., an MRI), and for each voxel of the image, determine a value that represents a likelihood that the voxel lies within a region of the 3D image that corresponds to a representation of a particular organ or tissue of the subject. A CNN module may be software and/or hardware. For example, a CNN module may be implemented entirely as software, or certain functions of a CNN module may be carried out via specialized hardware (e.g., via an application specific integrated circuit (ASIC)).

As used herein, the term "tissue" refers to bone (osseous tissue) as well as soft-tissue.

In certain embodiments, the approaches described herein can be used to segment and identify target tissue regions within a full body image of a subject. As used herein, the terms "full body" and "whole body" used (interchangeably) in the context of segmentation refer to approaches that evaluate a majority (e.g., greater than 50%) of a graphical representation of a subject's body in a 3D anatomical image to identify target tissue regions of interest. In certain embodiments, full body and whole body segmentation refers to identification of target tissue regions within at least an entire torso of a subject. In certain embodiments, portions of limbs are also included, along with a head of the subject.

A. Detecting and Assessing Cancer Status Via Nuclear Medicine Imaging and Automated Image Segmentation Described herein are systems and methods that provide artificial intelligence (AI)-based segmentation technology that provides a basis for detecting, evaluating, and making predictions about cancer status of subjects. In particular, the AI-based segmentation techniques described herein allow for 3D representations of various tissue regions in medical images to be accurately and rapidly identified. The AI-based segmentation technologies described herein utilize machine learning techniques, such as Convolutional Neural Networks (CNNs) to automatically to identify a plurality of target 3D volumes of interest (VOIs) each corresponding to a specific target tissue region, such as one or more organs, portions of organs, particular bone(s), a skeletal region etc. Each identified 3D VOI may be represented via a segmentation mask. The multiple segmentation masks, identifying multiple target tissue regions across a patient's body, can be stitched together to form a segmentation map. The segmentation map, and/or various segmentation masks that it comprises, may be used compute various quantities from medical images, such as useful indices that serve as measures and/or predictions of cancer status, progression, and response to treatment. Segmentation maps and masks may also be displayed, for example as a graphical representation overlaid on a medical image to guide physicians and other medical practitioners.

In certain embodiments, AI-based segmentation is performed using an anatomical image that provides detailed structural information about locations and extent of tissue within a subject's body. Examples of anatomical images include, without limitation, x-ray computed tomography (CT) images, magnetic resonance images (MRI), and ultrasound. Image contrast in anatomical images is a function of physical properties of underlying tissue, such as density, water and fat content. As described in further detail herein, the AI-based segmentation techniques of the present disclosure analyze contrast variations and patterns in anatomical image to identify target 3D VOIs that correspond to different specific target tissue regions.

In certain embodiments, structural information and identified target VOIs from anatomical images are combined with and/or used to analyze images obtained via functional imaging modalities. Functional images reflect physiological properties and activity in a subject. They are often acquired using probes and have intensity variations that reflect a spatial distribution of the probes within an imaged portion of a subject. For example, nuclear medicine images (e.g., PET scans; e.g., SPECT scans; e.g., whole-body scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

Transferring a segmentation map to a functional image (e.g., a nuclear medicine image, such as a PET image or a SPECT image) provides valuable context for evaluating and deriving meaning from intensity fluctuations in the functional image. In particular, it allows for regions of the functional image to be identified as corresponding to particular tissue regions of the subject. In this manner, intensity values and fluctuations in and across voxels within a particular region can thus be understood as originating from underlying accumulation of a radiopharmaceutical in a specific tissue region (e.g., organ or bone) of the subject.

As described in further detail herein, this anatomical context serves a variety of uses. For example, it allows for measures of radiopharmaceutical uptake in various specific target organs and tissue regions, such as prostate, lymph nodes, and bone, to be assessed, and used as an indicator of presence of cancerous tissue therein. Identifying a what particular region intensities of a functional image are associated with also allows them to be evaluated in proper context. For example intensities of a certain value, if associated with a prostate region, may be more likely to be indicative of cancer than intensities of the same value, when found within another organ, such as a bladder or kidney. In certain embodiments, reference regions are identified and used to compute normalization values and levels on a scale to which intensities in other regions are compared to evaluate a cancer status. Background regions, to either be excluded from the image or used to correct for artifacts may also be identified.

Accordingly, the AI-based segmentation approaches described herein can serve as a platform on which a variety of tools and techniques for detecting, evaluating, and predicting cancer status for patients can be built. Moreover, since the AI-based segmentation tools described herein can identify a variety of important tissue regions across an entire body of a patient, and then transfer those identifications (e.g., segmentation maps) from anatomical images to various functional images, they can be used as a building block for analysis techniques based on a variety of different imaging methods that obtain contrast via a variety of different radiopharmaceuticals.

Figure 2:
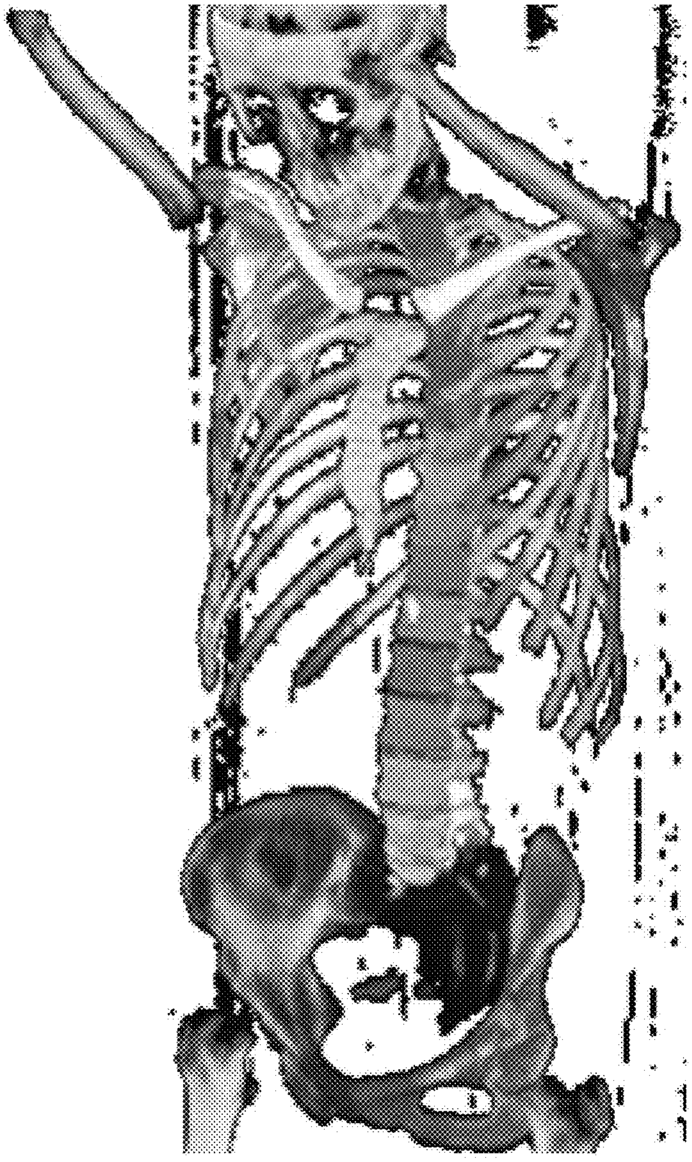
FIG. 2 is an image showing a skeleton of a subject with various specific bones identified, according to an illustrative embodiment.
Figure 3:
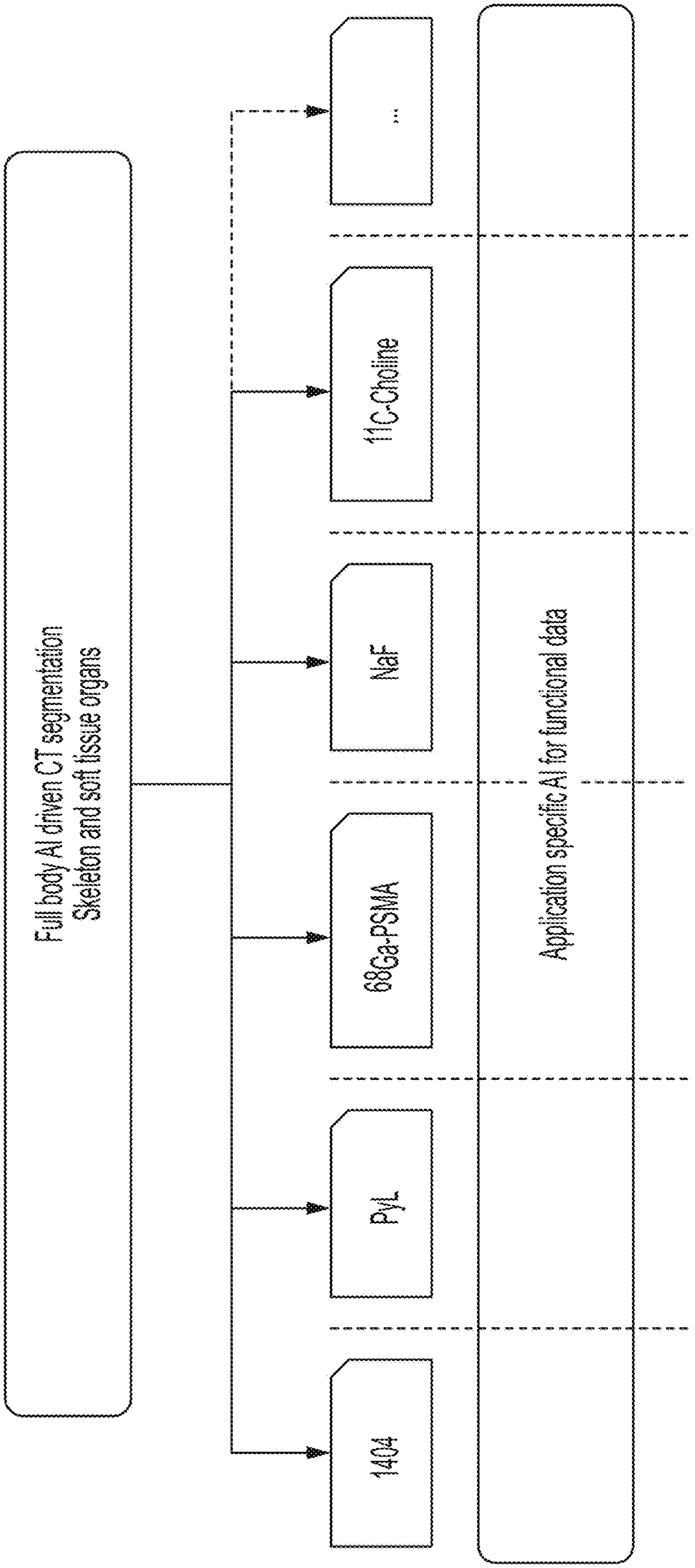
FIG. 3 is a block diagram showing use of full body segmentation in various functional imaging modalities, for various applications, according to an illustrative embodiment.

FIGS. 1-3 illustrate this concept. In particular, FIG. 1 is a schematic illustrating how various anatomical and functional imaging modalities can be integrated in the context of a platform agnostic AI-based segmentation technology. As illustrated in FIG. 1, the AI-segmentation platform described herein can be used as a basis for analysis of a variety of images, such as anatomical CT image themselves, 18NaF images, C-11 images, Ga-68 images, FDG image, and PyL™ images. FIG. 2 shows results of an example segmentation performed on a skeleton of a subject, with different specific bones identified by different colors. The segmentation shown in FIG. 2, performed using a CT image, can be transferred to a functional image in order to identify 3D volumes in the functional image that correspond to the target VOIs identified within the CT image. Other VOIs, such as soft-tissue, may also be identified and used to identify corresponding 3D volumes in a functional image. For example, FIG. 3 is a block flow diagram illustrating how segmentation of various soft-tissue and bone regions based on an anatomical image (e.g., a CT image) can be used and mapped to images obtained via various functional imaging modalities using various probes (e.g., $^{99m}$Tc-MIP-1404, $^{18}$F-PyL, $^{68}$Ga-PSMA-11, $^{18}$F—NaF, $^{11}$C-Choline, [18F]FDG, [18F]FACBC, etc.) to perform image based diagnosis and assessment of disease progression, state, and the like. As shown in FIG. 3, the full body segmentation techniques described herein can serve as a platform that a variety of application specific image analysis techniques that utilize different functional imaging modalities and probes can leverage and be built upon.

Figure 4:
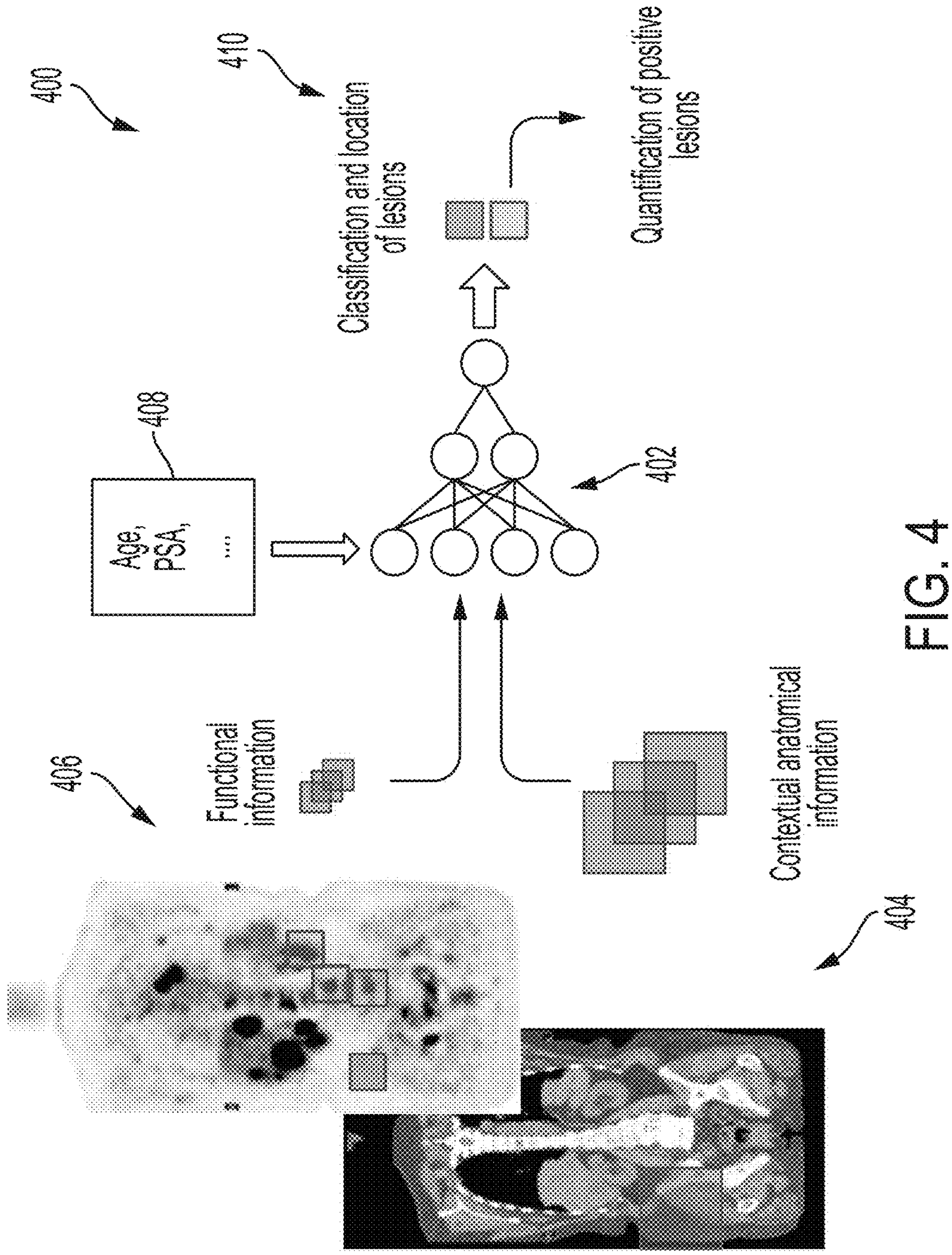
FIG. 4 is a diagram showing processing flow of different informational datasets by an AI module to classify, locate, and quantify cancerous lesions, according to an illustrative embodiment.

FIG. 4 is a diagram showing how artificial intelligence-based image analysis 400 can be performed to classify and locate lesions, as well as quantify positive lesions, e.g., for assessing cancer state in a subject. As shown in FIG. 4, a machine learning module 402, such as a convolutional neural network (CNN), receives contextual anatomical information (e.g., a CT image or other anatomical imaging modality) 404 along with functional information (e.g., a functional image, such as a SPECT, PET, or other functional image obtained using a particular imaging probe) 406. The machine learning module 402 then uses the functional 406 and anatomical 404 information to identify, classify, and/or quantify cancerous lesions in a subject 410. The machine learning module 402 may also leverage additional information 408, such as subject demographic data (e.g., age, weight, etc.) and other diagnostic test results (e.g., a biopsy, Gleason score, genetic testing results, a prostate specific antigen (PSA) test result), clinical treatment(s) (e.g., external beam radiation, brachytherapy, prostatectomy, antiandrogens, immunotherapy (e.g., Provenge), chemotherapy, etc.) as input and base the classification, identification, and/or quantification of cancerous lesions on this additional information as well.

Figure 5A:
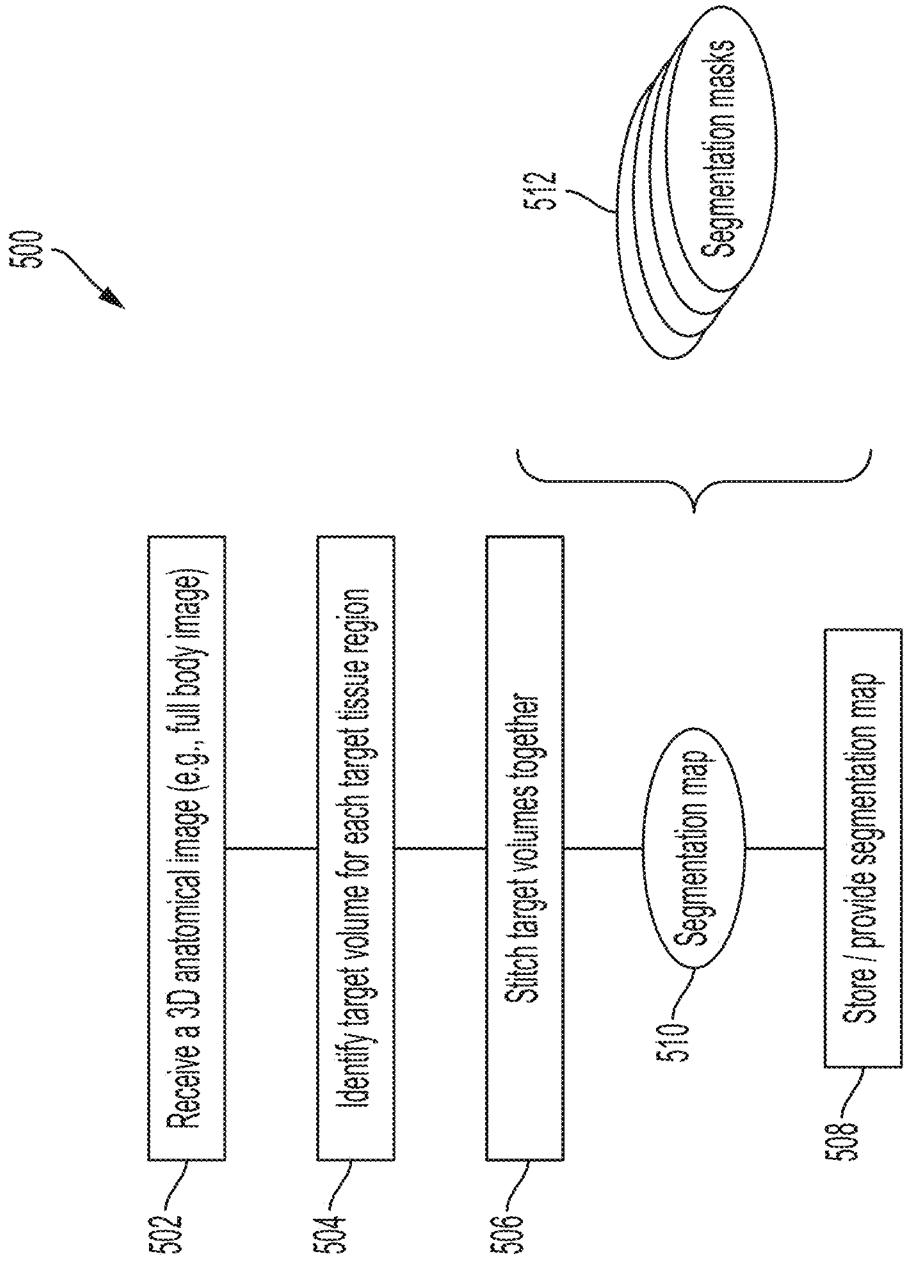
FIG. 5A is a block flow diagram of a process for automatically processing 3D images to identify 3D volumes within the 3D images that correspond to particular target tissue regions, according to an illustrative embodiment.

FIG. 5 is a block flow diagram showing an example process 500 for performing segmentation to identify a plurality of target tissue regions. As shown in FIG. 5, a machine learning module receives a 3D anatomical image (e.g., a full body image) as input 502, and identifies, for each of a plurality of target tissue region, a target volume comprising a graphical representation of the target tissue region within the 3D anatomical image 504. The target volumes are stitched together 506 to form a segmentation map 510 that comprises a plurality of segmentation masks 512, with each segmentation mask representing an identified target volume. The segmentation map 510 can be stored and/or provided for display and/or further processing 508.

i. Image Segmentation using Convolutional Neural Networks (CNNs)

In certain embodiments, the AI-based image segmentation approaches described herein utilize machine learning techniques, such as CNNs to perform segmentation. As described herein, one or more machine learning modules may be used to perform intermediate analysis and processing of images, and ultimately identify target VOIs.

In certain embodiments, the AI-based image segmentation described herein utilizes a two-step approach to identify one or more of the 3D target VOIs representing target tissue regions of interest in an anatomical image. In this two-step approach, an initial volume of interest (VOI) that comprises one or more of the target VOIs is first identified. The initial VOI may be identified using a first module, referred to as a localization module. The localization module may be a first machine learning module, such as a first Convolutional Neural Network (CNN) module. Once the initial VOI is identified, a second module, referred to as a segmentation module [e.g., that implements a second machine learning network (e.g., a second CNN) to perform fine segmentation], is used to identify one or more target VOIs within the initial VOI. This approach is advantageous as allows the segmentation module to operate on a standardized input, of manageable size, without regard to variations in dimensions and boundaries of the original anatomical image received. This two-step approach is especially useful for performing accurate, finely resolved segmentation of tissue regions within a large image, such as a full body scan. The localization module may perform a rough analysis, such as by performing a coarse segmentation, to identify the initial VOI. Freed from having to accommodate varying image sizes, and analyze an entire image, the segmentation module can devote resources to performing fine segmentation to accurately identify the target VOIs within the initial VOI.

Moreover, as described in further detail herein, for example in Example 1, to identify a set of target VOIs spread out across an entire body of a subject, multiple initial VOIs can be identified in order to partition a whole body image into multiple manageable initial VOIs, each comprising a subset of the desired target VOIs to be identified. The partitioning of a whole body image into multiple initial VOIs can be performed using a single localization module, such as a machine learning module that performs a coarse segmentation to identify general anatomical regions such as an upper body, a lower body, a spine, and a pelvic region. In certain embodiments, multiple localization modules (e.g., each tasked with identifying one or more initial VOIs) may be used. For each identified initial VOI, one or more segmentation modules may then be used to perform fine segmentation and identify the one or more desired target VOIs within the initial VOI.

Various localization and segmentation modules may be combined and implemented as a single module and/or a single software application, or may be implemented separately, e.g., as separate software applications.

A number of different approaches may be used by a localization module to identify a particular initial VOI. For example, in one approach, the localization module may implement a CNN that receives a grayscale CT image (e.g., a single input channel) as input and outputs coordinates of opposite corners of a rectangular VOI (e.g., a bounding box). In another approach, the localization module may implement a CNN that receives two input channels: (i) a grayscale CT image, and (ii) a pre-processed version of the CT image. The pre-processed version of the CT image may be a thresholded version of the CT image, wherein the thresholding provides a rough identification of the initial VOI to be identified. The CNN is trained to analyze both these input channels in order to output coordinates representing opposite corners of a rectangular initial VOI (e.g., a bounding box).

In a third approach, in order to identify a particular initial VOI comprising one or more specific target VOIs, the localization module performs a coarse segmentation to roughly identify the specific target VOIs. In this way, the localization module is essentially a rough version of the segmentation modules used to identify the specific target VOIs within the particular initial VOI. A rectangular initial VOI is then generated using the coarsely identified specific target VOIs (e.g., by drawing the smallest box that fits them, or maybe adding some buffer distance). A distinction here is that the output of the localization module in this case is not merely coordinates of cuboid vertices. In this approach, likelihood values are automatically determined for each voxel of the image that give the likelihood as to how the voxel is classified—e.g., whether the voxel is a particular initial VOI, or background, for example.

In certain embodiments, voxel classifications performed by the machine learning modules may be refined via an iterative process in order to mitigate noise in the classification process. In particular, in certain embodiments, a machine learning module such as a CNN module receives an entire image, or portion thereof as input, and outputs, for each particular voxel, a label classifying the particular voxel as (i) one of a set of pre-defined classes corresponding to anatomical regions or target tissue regions, or (ii) background. For example, a localization module trained to identify initial VOIs corresponding to a spine, a pelvic region, and a left and right upper body may label each voxel as 1, 2, 3, or 4 for spine, pelvic region, left upper body, and right upper body, respectively, or 0 for background.

A segmentation module that identifies one or more target tissue regions within a particular initial VOI may receive the particular initial VOI as input, and output an integer label for each voxel, with the integer label identifying that voxel as corresponding to one of the particular target tissue regions, or background. For example, a segmentation module that identifies different vertebrae may receive as input an initial VOI corresponding to the spine, and label each voxel in the initial VOI with an integer corresponding to a particular vertebra (e.g., 1 for a first lumbar vertebra, 2 for a second lumbar vertebra, 3 for a third lumbar vertebra, etc. with other integer labels for other bones).

The classification performed by machine learning modules as described above, may produce noisy results, with certain isolated voxels having different labels than their surroundings. For example, a CNN module may produce an output wherein a majority of voxels within a large volume are assigned a first label, with isolated voxels and/or small groups of voxels assigned different, e.g., second or third labels, identifying them as corresponding to different anatomical regions than their neighbors. Often such isolated voxels and/or islands appear on the edges of a large uniformly labeled region.

These small non-uniformities correspond to noise in the classification process, and can be removed via an iterative procedure as follows. First, for each label representing (i) a particular anatomical region or target tissue region, or (ii) background, an associated largest connected component of labeled voxels is identified. Second, for each particular label, differently labeled isolated voxels and/or voxel islands that are immediately adjacent to voxels of the largest connected component associated with the particular label are identified and re-assigned the particular label. In certain embodiments, in a third step, any remaining isolated differently labeled voxel islands can then be removed. In a fourth step, holes in segmentation regions—voxels that are labeled as background but are completely encapsulated by non-background labeled voxels are filled (e.g., by assigning voxels of the holes a label of the non-background region that encapsulates them). The second through fourth steps, in which isolated voxels and/or voxel islands are relabeled based on their surroundings are repeated until convergence—i.e., no change from on iteration to the next. This approach reduces and/or eliminates isolated voxels of a different label from their surrounding thereby mitigating noise in the classification process.

These various approaches for identifying initial VOIs may be used alone or in combination to identify multiple initial VOIs within an anatomical image of a subject. Once one or more initial VOIs are identified, one or more target VOIs within each initial VOI may be identified. For example, PCT Publication WO2019/136349, the content of which is hereby incorporated by reference in its entirety, provides further detail on how a single initial VOI corresponding to a pelvic region may be identified within a CT image, and how fine segmentation may be performed to identify target VOIs corresponding to organs such as a prostate, bladder, gluteal muscles, as well as various pelvic bones, such as a sacrum, coccyx, and left and right hip bones, may be identified. The approaches described herein, and in particular in Examples 1-4, show how multiple initial VOIs can be identified and used to identify a plurality of target VOIs across a subject's body, thereby providing for accurate whole-body image segmentation that can serve as a basis for detection and assessment of cancer status, progression, and response to treatment at localized stages in various organs and tissue regions, as well as metastatic stages where it is present in multiple regions in a patient's body.

ii. Providing Anatomical Context to 3D Functional Images

Segmentation maps generated by automated AI-based analysis of anatomical images can be transferred to 3D functional images in order to identify, within the 3D functional image, 3D volumes corresponding to the target VOIs identified in the anatomical image. In particular, in certain embodiments, the individual segmentation masks (of the segmentation map) are mapped from the 3D anatomical image to the 3D functional image. The 3D volumes identified within the 3D functional image can be used for a variety of purposes in analyzing images for assessment of cancer status.

Certain identified 3D volumes and corresponding target VOIs correspond to tissue regions where cancer is suspected and/or may occur. Such regions may include, for example, a prostate, breast tissue, lung(s), brain, lymph nodes, and bone. Other regions may also be evaluated. Certain regions, such as prostate, breast, and lungs, are relevant for detecting cancer at earlier, localized stages, while others, such as lymph nodes and bone are relevant for assessing metastatic cancer. Since intensities of functional images, such as PET and SPECT images map spatial distribution of radiopharmaceutical accumulation in a patient's body, by accurately identifying specific 3D volumes in functional images that correspond to specific tissue regions intensities of voxels within those 3D volumes can be used determine a measure of uptake of radiopharmaceutical probes within the specific tissue regions to which they correspond. Since radiopharmaceutical probes can be designed to selectively accumulate in cancerous tissue (e.g., via enhanced affinity to biomolecules that are overexpressed in cancerous tissue, such as prostate specific membrane antigen (PSMA)), detecting and quantifying uptake of particular probes in certain target tissue regions and organs is of interest is indicative of and/or can be used to determining a cancer status for the subject. For example, as described in PCT Publication WO2019/136349, the content of which is hereby incorporated by reference in its entirety, assessing 1404 uptake in a prostate volume can be used to determine a prostate cancer status for a subject. Other probes may be used to assess metastatic cancer, present in a wide variety of other tissue regions, including bones. For example, Examples 2 to 6 describe segmentation used to identify accumulation of PyL™ in cancerous lesions throughout a patient's body.

Accordingly, in certain embodiments, segmentation performed on an anatomical image, such as CT image, is transferred (e.g., mapped) to a co-registered functional image, such as a PET or SPECT image, allowing for specific tissue volumes of interest within the functional image that correspond to particular tissue regions of interest to be identified. Accumulation of radiopharmaceutical within those particular tissue regions can then be quantified based on intensities of functional image voxels that lie within the specific tissue volumes of interest.

A variety of approaches can be used to analyze voxel intensities in functional images. For example, an average, a median, a total, a maximum, etc. intensity within a specific volume may be computed and used for quantification. This computed value may then be compared with other values, e.g., computed for other tissue regions (e.g., for normalization), and used to assign a cancer status to a patient (e.g., based on comparison with one or more predetermined threshold values). In certain embodiments, localized regions of high intensity—referred to as hotspots, are identified within particular 3D volumes. As described in further detail in section B, below, these localized hotspots can be identified as representing cancerous lesions, and used to determine cancer status of a subject. In certain embodiments, machine learning approaches can be used. For example, intensities of functional image voxels lying within one or more specific tissue volumes of interest can be used as inputs to machine learning modules that compute a risk index that can, in itself be used to quantify a risk of cancer, metastasis, or recurrence of cancer, etc. and/or compared with reference values, such as thresholds, to assign a particular cancer status.

In certain embodiments, in addition to identifying specific tissue regions in which cancerous tissue is may be present, e.g., in order to determine the presence and/or the state of cancer therein, other additional tissue regions may be identified. Such additional tissue regions may correspond to background regions in which a particular radiopharmaceutical probe accumulates under normal circumstances, without lesions necessarily being present.

In certain embodiments, identified background regions are used to normalize voxel intensities so as to standardize intensity values from image to image. For example, as described in PCT Publication WO2019/136349, the content of which is hereby incorporated by reference in its entirety, gluteal muscles can be identified and uptake in them can be used to normalize intensities in SPECT images obtained following administration of 1404.

Identification of certain background regions can also be used to account for high probe accumulation levels in these regions. In certain embodiments, certain background regions are identified and excluded from analysis. For example, as described in Example 3, certain probes, such as PyL™ may accumulate in certain background regions under normal circumstances, absent any cancerous lesions or tissue within those regions. Accordingly, these regions may be identified and excluded from, e.g., hotspot detection analysis. Examples of such regions include kidneys, duodenum, small intestines, spleen, liver, pancreas, stomach, adrenal gland, rectum, and testes.

In certain embodiments, identifying 3D volumes in a functional image that correspond to background regions can be used to correct for intensity bleed effects, where high accumulation of radiopharmaceutical in a particular region may produce high intensities in the functional image not only in the 3D volume that corresponds to the particular region, but also in its neighborhood. Such intensity bleed into other regions of functional images can mask useful signal. For example, radiopharmaceutical typically accumulates in high amounts in a patient's bladder. When imaged via a functional imaging modality, this high accumulation in the bladder may, via scattering effects, contribute to intensities in 3D volumes corresponding to tissue regions outside the bladder, such as a prostate. Accordingly, accounting for this intensity bleed or "cross-talk" can improve the accuracy with which intensities in a 3D functional image are used to measure underlying radiopharmaceutical uptake.

In certain embodiments, the 3D volume corresponding to the particular background region producing the intensity bleed is dilated. The dilated background region may be excluded from analysis, so as to avoid using intensities of regions directly adjacent to the background region to determine uptake metrics or identification of hotspots.

In certain embodiments, a suppression method which models the profile of the functional intensities may also be used to adjust the intensity levels in neighboring regions to correct for the intensity bleed. In this approach, for a particular background region that produces intensity bleed, an amount of suppression, that is, intensity bleed, to remove from a particular voxel of the functional image is dependent on a distance from that voxel to a high intensity core region within a particular 3D background volume corresponding to the particular background region. The high intensity core region may be determined as a region comprising voxels having intensities above a predetermined value, or within a specific fraction of a maximum intensity in a specific region of the functional image.

In certain embodiments, this suppression is utilized if a maximum functional image intensity within a 3D volume identified as corresponding to the particular background region is more than a specific multiplier value times a determined background intensity value. Background intensity values may be determined based on intensities of voxels of the 3D functional image corresponding to specific reference volumes corresponding to specific tissue regions, such as gluteal muscles. The suppression approach may be applied to a sub-region of the 3D functional image in the vicinity of the particular background region producing intensity bleed. For example, it may be applied to a rectangular sub-region encompassing the particular region, plus a predetermined margin.

In certain embodiments, one or more intensity bleed functions are determined to perform suppression and thereby correct intensities of voxels of the 3D functional image for bleed (e.g., cross-talk). For example, the 3D functional image may be cropped to the aforementioned rectangular sub-region encompassing the particular region plus the predetermined margin. A determined background intensity value can be subtracted from intensities of voxels within the cropped image region. Sample intensities can then be collected to determine how intensity originating from radiopharmaceutical uptake within the particular background region decreases as one moves away from the particular background 3D volume corresponding to the particular background region. Samples beginning at an extreme top, right, left, and bottom, and then moving outwards up, right, left, and down, respectively, may be used. Other directions are also possible. The sampled intensities provide curves (e.g., sets of sampled intensity data points) showing intensity decrease from the high intensity core. Template functions, such as n-th degree polynomials can be fit to these sampled curves and used to compute intensity values to be used as correction factors in the vicinity of the particular 3D background volume.

For example, PCT Publication WO2019/136349, the content of which is hereby incorporated by reference in its entirety describes how identification of a bladder region can be used to adjust prostate voxel intensities for intensity bleed through due to high accumulation in the bladder in 1404-SPECT images. In certain embodiments, similar approaches can be used for other images obtained with other probes, which may accumulate in the bladder, and/or other regions (e.g., the liver, the kidneys, etc.).

In certain embodiments, the segmentation approaches described herein assume that the 3D anatomical image includes certain anatomical regions. For example, an embodiment of the systems and methods described herein may assume that its input anatomical images always include a pelvic region, and automatically attempts to segment the pelvic region. The systems and methods described herein may also, for other anatomical regions, only segment such regions if they are included in the anatomical image input, for example first performing a determination as to whether they are present.

Approaches for performing whole body segmentation to identify target tissue regions corresponding to bone and/or soft-tissue (e.g., organs) are described in further detail in Examples 1, 2, 3, and 4 below. Also described are approaches for using such whole body segmentation for assessment of disease state, in particular, cancer in a patient.

B. Hotspot and Lesion Detection

In certain embodiments, instead of, or in addition to, quantifying overall uptake in a particular volume within the functional image, localized hotspots (localized regions of relatively high intensity) are detected. In certain embodiments, hotspots are detected via a thresholding approach—by comparing intensities of voxels within the functional image to one or more thresholds values. Groupings of voxels with intensities above a threshold may be detected as hotspots. A single, global, threshold value may be used, or, in certain embodiments, multiple region specific thresholds may also be used. For example, segmentation of the co-registered anatomical image can be used to set different thresholds for different tissue regions used for hotspot detection. Segmentation of the co-registered image can also be used, as described herein, to remove effects of background signal, thereby facilitating hotspot detection (e.g., if a global threshold and/or multiple regional thresholds are used).

In certain embodiments, hotspots can additionally be detected using blob detection techniques. One approach is to use the Difference of Gaussians approach, where a PET image is filtered through a combination of high and low-pass filters approximated by Gaussian kernels. The filters reduce background noise and are invariant to changes in background levels in the different regions of the image (e.g. the thorax might have significantly higher background levels due to significant uptake in liver and kidneys compared to the pelvic region). This cascaded high/low-pass filter approach would allow for hotspot extraction without the utilization of fixed thresholds, but could instead identify local changes in the PET intensities. Another approach is to employ a Laplacian of a Gaussian blob detection method. The Laplacian of a Gaussian approach is a method for detecting edges in images using Laplacian and Gaussian filter kernels. By using different sizes of kernels, edges of structures of different sizes are detected. Choosing appropriate kernel sizes allows the method to detect structures that have properties common to lesions. The described approaches may be used in a stand-alone fashion where only one of the techniques is used for all regions of interest, or they may be used simultaneously, where different methods can be employed for different tissue regions as identified by the semantic segmentation of the co-registered anatomical image in conjunction with either a single global threshold or multiple local thresholds.

Figure 5B:
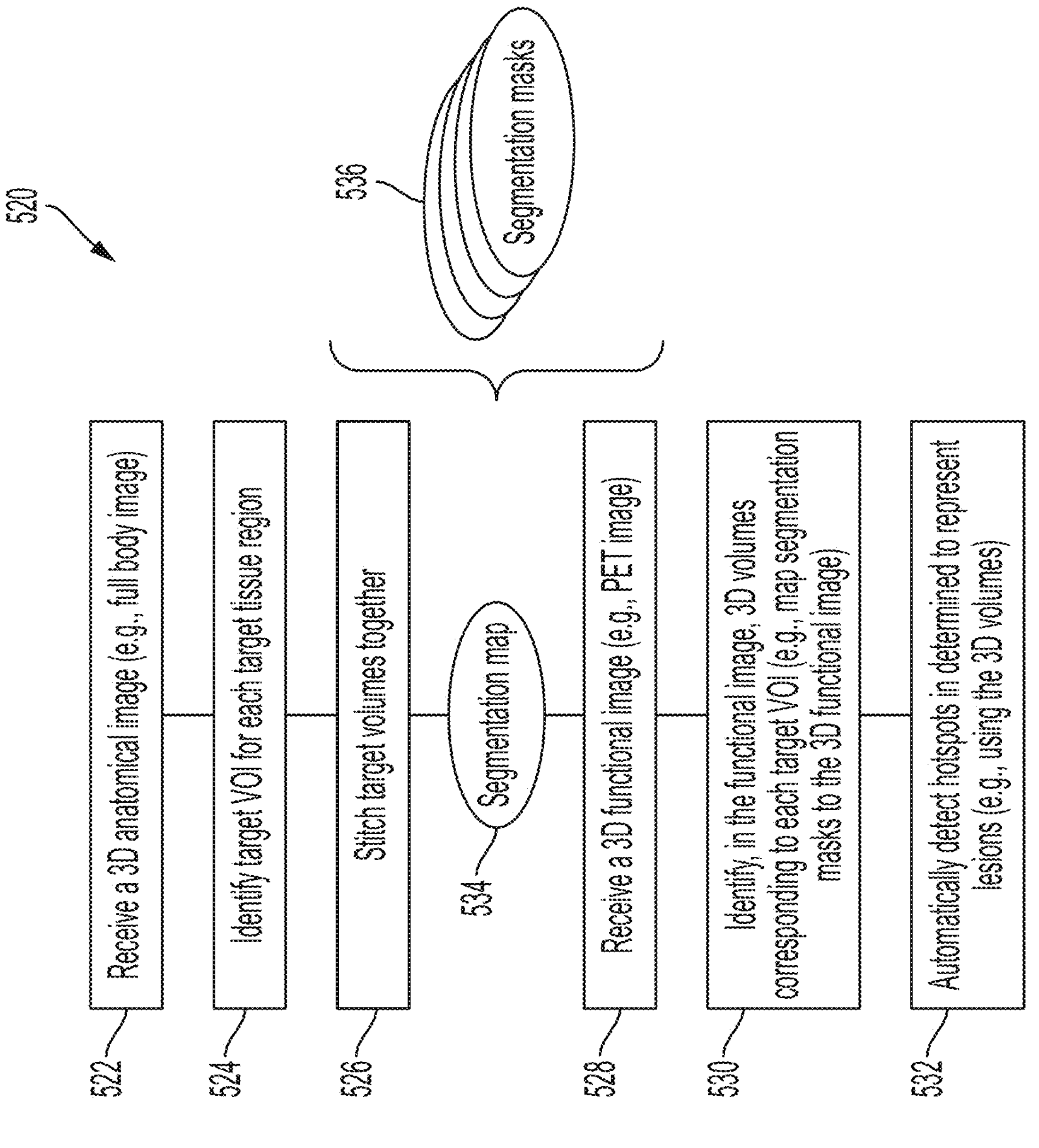
FIG. 5B is a block flow diagram of a process for automatically processing 3D images to identify 3D volumes and use the 3D volumes to detect hotspots representing cancerous lesions, according to an illustrative embodiment.

FIG. 5B shows an example process 520 for using the segmentation approaches described herein to detect hotspots representing cancerous lesions. In a first step, a 3D anatomical image is received 522. A one or more target VOIs corresponding to particular target tissue regions are identified within the 3D anatomical image 524 and the identifications of the target VOIs are stitched together 526 to create a segmentation map 534 comprising a plurality of segmentation masks 536. Each segmentation mask of the segmentation map represents a particular target VOI. Next, a 3D functional image (e.g., a PET image) is received 528 and the segmentation map is transferred to the 3D functional image to identify, for each target VOI, a corresponding 3D volume in the 3D functional image 530. The identified 3D volumes are then used to detect 532, within the 3D functional image, one or more hotspots corresponding to localized regions of high intensity relative to their surroundings. In particular, one or more specific 3D volumes may correspond to specific tissue regions where cancerous lesions may form, and be analyzed to detect hotspots therein. Other 3D volumes may be used to perform background correction, or intentionally be excluded from the hotspot detection process. As described in further detail herein, still other volumes may be relevant in that they are used as reference volumes for computing useful indices that can be assigned to hotspots in order to score them, e.g., to indicate risk/severity of the underlying lesions they represent.

Hotspots may also be classified following their initial detection, e.g., as cancerous or not, and/or assigned likelihood values representing their likelihood of being a metastases. Hotspot classification may be performed by extracting hotspot features (e.g., metrics that describe characteristics of a particular hotspot) and using the extracted hotspot features as a basis for classification, e.g., via a machine learning module.

In certain embodiments, hotspot classification can also be performed without the use of machine learning. In such embodiments, anatomical knowledge can be combined with information relating to the shape and location of a detected hotspot to classify the hotspot as either a cancerous lesion or noise. For example, if a detected hotspot is located on the edge of a rib facing the liver and the detected peak is not the global maximum in the area surrounding the hotspot, it is possible to estimate whether the hotspot is a tumor or not based on the given anatomical and spatial information. The segmentation of the co-registered anatomical image can additionally be used to create intensity models of background tissue regions known to not contain cancerous cells, but where exceptionally high functional image voxel intensities are common. Such background regions may cause intensity bleed outside of the boundaries of the background region itself and impact the neighboring regions where cancerous lesions might exist. Profiles of the intensity levels can be estimated and used to subtract the estimated additional intensity levels present in neighboring tissue regions harboring cancerous lesions to allow a more robust hotspot detection.

Hotspots representing lesions may be used to determine risk indices that provide an indication of disease presence and/or state (e.g., a cancer status, similar to a Gleason score) for a patient. For example, metrics such as number of hotspots, a total summed intensity of identified hotspots, area fraction of a particular body part or region (e.g., skeleton) occupied by hotspots, and the like, may be used themselves as, and/or in calculation of, such risk indices. In certain embodiments, regions identified via the segmentation approaches described herein may be used in computation of risk indices, for example in computing metrics such as area fractions. Examples of approaches for using identified hotspots to compute risk indices is provided herein, in Examples 5 and 7.

C. Example CNN-Based Whole Body Segmentation and Lesion Detection Approaches

The following examples demonstrate use of the AI-based segmentation and hotspot detection approaches described herein for whole-body segmentation, detecting cancerous lesions, and determining useful metrics for evaluating a cancer status of a subject.

i. Example 1—CNN Based Whole Body Segmentation

Example 1 describes an example approach for whole body segmentation. The implementation in this example uses five neural networks to segment bones within an entire torso. A first neural network is used to roughly localize different regions of the body. The results are used to divide the body into four regions. In each of these regions, a corresponding neural network is then used to perform segmentation into distinct bones. The results from all four regions are then combined into a finished result (e.g., a final segmentation map).

This approach is related to the two-step 'bounding box' approach described herein, wherein a first machine learning module (e.g., a localization module) is used to roughly localize an initial volume of interest (VOI) corresponding to an anatomical region that comprises one or more particular target tissue regions (e.g., a prostate). A second machine learning module (e.g., a segmentation module) then performs a fine segmentation within the initial VOI to identify target volume(s) corresponding to the target tissue region(s) within the initial VOI. In this case, for whole body segmentation, the first machine learning module (localization module) identifies multiple initial VOIs, each corresponding to a different anatomical region. Then, for each anatomical region, a corresponding secondary machine learning module (segmentation module) identifies one or more target volumes, each representing a particular target tissue region. The machine learning modules (e.g., neural networks) may be implemented as separate modules, or certain machine learning networks may be combined. For example, each secondary, segmentation network may be implemented as a separate module, or within a single module.

Accordingly, in this example, the first module (localization) is used for identifying the anatomical regions within the CT; that is, to find volumes of interest where networks of the second module can be applied to generate the segmentation map that is used for further analysis. The networks in the second module work with a full-resolution CT image, while the localization network works in low resolution, using a sub-sampled version of the CT image.

Three example versions of CNN networks used in software implementing whole-body segmentation in accordance with the approaches. Versions 1 and 2 segment 49 bones, and version 2 segments 49 bones and 8 soft-tissue regions.

CNN-Based Segmentation Platform Example Version 1

In a first example version of a CNN network used for whole body segmentation, the first machine learning module (localization module) in this example is referred to as "coarse-seg", and was trained to identify 49 bones in sub-sampled CT images (a sub-sampling factor of 4 along each dimension). The localization module was used to differentiate regions of the body in to a pelvic region, a spine, a left upper body, and a right upper body. The four fine segmentation networks were as follows:

- "fine-seg-pelvic": Trained to identify the left and right ilium and the sacrum and coccyx;
- "fine-seg-spine": Trained to identify 12 thoracic vertebrae, 5 lumbar vertebrae, and the sternum;
- "fine-seg-left-upper-body": Trained to identify 12 ribs on the left side of the body, the left scapula, and left clavicle; and "fine-seg-right-upper-body": Trained to identify 12 ribs on the right side of the body, the right scapula, and right clavicle.

The input image sizes for each network were as follows:

TABLE 1

Input image sizes for five neural networks.

| Network Name | Input image size (no. slices, no. rows, no. columns) |
|---|---|
| coarse-seg | (81, 70, 104) |
| fine-seg-pelvic | (93, 146, 253) |
| fine-seg-spine | (194, 204, 94) |
| fine-seg-left-upper-body | (158, 187, 144) |
| fine-seg-right-upper-body | (158, 191, 146) |

While the coarse-seg network of the localization module received, as an input image, an 3D anatomical image representing a large physical volume and comprising a majority of the subject's body, the actual number of voxels in its input image was lower than for the other networks due to the factor of 4 sub-sampling. The number of voxels and size of the input image to the localization module was also reduced by cropping (removing) regions of the image that did not include graphical representations of tissue, but instead represent air. Removing these voxels as a pre-processing step further reduced the size of the image input to the localization module (see e.g., first two columns of Table 4 below). Reducing the size of the image input to the localization module via sub-sampling allows the coarse-seg network to trade resolution of the image on which it operates for additional filters, which allow it to e.g., account for variability in images it receives and perform more accurate and robust coarse segmentation to identify the different initial volumes of interest.

The number of filters and parameters used in each neural network are listed in Tables 2-4, below:

TABLE 2

Number of convolutional filters in five neural networks.

| Network Name | Total Number of Filters | Number of Filters in First Layer |
|---|---|---|
| coarse-seg | 4096 + 49 (49 classes) | 32 |
| fine-seg-pelvic | 4096 + 3 | 32 |
| fine-seg-spine | 2048 + 18 | 16 |
| fine-seg-left-upper-body | 2048 + 14 | 16 |
| fine-seg-right-upper-body | 2048 + 14 | 16 |

TABLE 3

Number of parameters in five neural networks

| Network Name | Total params. | No. trainable params. | No. non-trainable params. |
|---|---|---|---|
| coarse-seg | 5,881,978 | 5,878,678 | 3,300 |
| fine-seg-pelvic | 5,880,276 | 5,877,068 | 3,208 |
| fine-seg-spine | 1,472,815 | 1,471,177 | 1,638 |
| fine-seg-left-upper-body | 1,472,731 | 1,471,101 | 1,630 |
| fine-seg-right-upper-body | 1,472,731 | 1,471,101 | 1,630 |

Table 4 below also shows a variability in input image size for the raw data and five neural networks used in this example. As shown in the table, variability in input image size for the four secondary, fine segmentation networks is less than that for the first, localization network since the identification of the initial VOIs produces a more standardized input for the secondary machine learning modules.

TABLE 4

Input image size for raw data and five neural networks.

| | Raw data | Coarse-seg (cropped by air) | Fine-seg-pelvic (cropped by coarse) | Fine-seg-spine (cropped by coarse) | Fine-seg-left-upper-body (cropped by coarse) | Fine-seg-right-upper-body (cropped by coarse) |
|---|---|---|---|---|---|---|
| rows mean px | 512 | 390 | 121 | 151 | 126 | 129 |
| rows std px | 0 | 39 | 7 | 19 | 20 | 21 |
| rows min px | 512 | 255 | 97 | 107 | 72 | 88 |
| rows max px | 512 | 399 | 136 | 189 | 170 | 188 |
| rows min mm | 700 | 308 | 133 | 146 | 98 | 120 |
| rows max mm | 700 | 546 | 186 | 258 | 232 | 242 |
| columns mean px | 512 | 399 | 207 | 67 | 112 | 113 |
| columns std px | 0 | 61 | 14 | 10 | 13 | 15 |
| columns min px | 512 | 311 | 155 | 45 | 84 | 72 |
| columns max px | 512 | 512 | 236 | 130 | 164 | 215 |
| columns min mm | 700 | 425 | 212 | 62 | 115 | 98 |
| columns max mm | 700 | 700 | 322 | 178 | 224 | 294 |
| slices mean px | 342 | 340 | 74 | 158 | 110 | 111 |
| slices std px | 99 | 95 | 6 | 12 | 11 | 12 |
| slices min px | 274 | 274 | 48 | 125 | 85 | 85 |
| slices max px | 624 | 624 | 92 | 208 | 136 | 140 |
| slices min mm | 822 | 822 | 144 | 375 | 255 | 255 |
| slices max mm | 1872 | 1872 | 276 | 624 | 408 | 420 |

CNN-Based Segmentation Platform Example Version 2

An updated, second, example version of the CNN whole-body segmentation system as described above in this example included adjustments to input image sizes, number of convolutional filters, and parameters used in the neural networks used to perform the segmentation. Tables 5, 6, and 7, as seen below, show updated values for the various parameters used in the five neural networks. Table 5 shows updated values for the input image sizes shown in Table 1, Table 6 shows updated values for the number of convolutional filters for the neural networks shown in Table 2, and Table 7 shows updated values for the number of parameters used by the neural networks shown in Table 3.

TABLE 5

Updated values for input image sizes for five neural networks.

| Network Name | Input image size (no. slices, no. rows, no. columns) |
|---|---|
| coarse-seg | (81, 77, 99) |
| fine-seg-pelvic | (92, 144, 251) |
| fine-seg-spine | (192, 183, 115) |
| fine-seg-left-upper-body | (154, 171, 140) |
| fine-seg-right-upper-body | (154, 170, 140) |

TABLE 6

Updated values for number of convolutional filters in five neural networks.

| Network Name | Total Number of Filters | Number of Filters in First Layer |
|---|---|---|
| coarse-seg | 4096 + 49 (49 classes) | 32 |
| fine-seg-pelvic | 3328 + 3 | 26 |
| fine-seg-spine | 2048 + 18 | 16 |
| fine-seg-left-upper-body | 2048 + 14 | 16 |
| fine-seg-right-upper-body | 2048 + 14 | 16 |

TABLE 7

Updated values for number of parameters in five neural networks

| Network Name | Total params. | No. trainable params. | No. non-trainable params. |
|---|---|---|---|
| coarse-seg | 5,882,423 | 5,879,132 | 3,300 |
| fine-seg-pelvic | 3,881,200 | 3,883,812 | 2,612 |
| fine-seg-spine | 1,472,815 | 1,471,177 | 1,638 |
| fine-seg-left-upper-body | 1,472,731 | 1,471,101 | 1,630 |
| fine-seg-right-upper-body | 1,472,731 | 1,471,101 | 1,630 |

CNN-Based Segmentation Platform Example Version 3

Another, $3^{rd}$, example version of the CNN whole body segmentation approach was used to segment soft-tissue regions as well as bones. As described herein, this $3^{rd}$ version included two coarse segmentation modules, which were used in parallel, referred to herein as "coarse-seg-02" and "coarse-seg-03".

The "coarse-seg-02" module was trained to identify 49 bones in sub-sampled CT images. The "coarse-seg-03" module was trained to identify 49 bones and the liver, in sub-sampled CT images. The "coarse-seg-02" module outperformed the "coarse-seg-03" module for localization of bones and, to take advantage of the benefits of each module, both were used in parallel, to identify initial volumes of interest (e.g., "bounding boxes") for different fine segmentation networks. In particular, in the 3rd version, seven fine segmentation networks were used. Six out of the seven fine segmentation networks used "coarse-seg-02" for initial volume of interest identification and a seventh, "fine-seg-abdomen", used "coarse-seg-03" for the initial volume of interest identification.

The seven fine segmentation networks for this 3rd example version of the CNN whole-body segmentation system are as follows:

"fine-seg-abdomen": Trained to identify the liver, left and right kidney, and gallbladder;

"fine-seg-left-lung": Trained to identify the left lung;

"fine-seg-right-lung": Trained to identify the right lung

"fine-seg-pelvic-region-mixed": Trained to identify the left and right ilium, the prostate, the urinary bladder, and the sacrum and coccyx;

"fine-seg-spine-bone": Trained to identify 12 thoracic vertebrae, 5 lumbar vertebrae, and the sternum;

"fine-seg-left-upper-body-bone": Trained to identify 12 ribs on the left side of the body, the left scapula, and left clavicle; and "fine-seg-right-upper-body-bone": Trained to identify 12 ribs on the right side of the body, the right scapula, and right clavicle.

Tables 8, 9, and 10, below, show values for the various parameters used in seven neural networks in the 3rd version of the CNN-based segmentation system.

TABLE 8

Input image sizes for the seven neural networks and two localization networks.

| Network Name | Input image size (Input image size (no. slices, no. rows, no. columns) |
|---|---|
| coarse-seg-02 | (81, 77, 99) |
| coarse-seg-03 | (81, 77, 99) |
| fine-seg-abdomen | (92, 176, 259) |
| fine-seg-left-lung | (154, 171, 140) |
| fine-seg-right-lung | (154, 171, 141) |
| fine-seg-left-upper-body-bone | (154, 171, 140) |
| fine-seg-right-upper-body-bone | (154, 170, 140) |
| fine-seg-pelvic-region-mixed | (92, 144, 251) |
| fine-seg-spine-bone | (192, 183, 115) |

TABLE 9

Number of convolutional filters in the seven neural networks and two localization networks.

| Network Name | Total Number of Filters | Number of Filters in First Layer |
|---|---|---|
| coarse-seg-02 | 2278 + 49 (49 classes) | 32 |
| coarse-seg-03 | 2278 + 50 | 32 |
| fine-seg-abdomen | 1142 + 16 (not all output classes are included in the complete segmentation platform) | 16 |
| fine-seg-left-lung | 1142 + 15 | 16 |
| fine-seg-right-lung | 1142+ 15 | 16 |
| fine-seg-left-upper-body | 1142 + 14 | 16 |
| fine-seg-right-upper-body | 1142 + 14 | 16 |

TABLE 9-continued

Number of convolutional filters in the seven neural networks and two localization networks.

| Network Name | Total Number of Filters | Number of Filters in First Layer |
|---|---|---|
| fine-seg-pelvic-region-mixed | 1852 + 5 | 26 |
| fine-seg-spine-bone | 1142 + 18 | 16 |

TABLE 10

Number of parameters in seven neural networks and two localization networks.

| Network Name | Total Params | No. trainable params | No. non-trainable params |
|---|---|---|---|
| coarse-seg-02 | 5,882,432 | 5,879,132 | 3,300 |
| coarse-seg-03 | 5,882,469 | 5,879,167 | 3,302 |
| fine-seg-abdomen | 1,473,003 | 1,471,369 | 1,634 |
| fine-seg-left-lung | 1,472,752 | 1,471,120 | 1,632 |
| fine-seg-right-lung | 1,472,752 | 1,471,120 | 1,632 |
| fine-seg-left-upper-body | 1,472,731 | 1,471,101 | 1,630 |
| fine-seg-right-upper-body | 1,472,731 | 1,471,101 | 1,630 |
| fine-seg-pelvic-region-mixed | 3,883,812 | 3,881,200 | 2,612 |
| fine-seg-spine-bone | 1,472,815 | 1,471,177 | 1,638 |

Accordingly, this example demonstrates how segmentation approaches described herein can be used to perform efficient whole body segmentation.

ii. Example 2: Automated Segmentation of the Skeleton in Low-Dose CT and Quantification of Metastatic Prostate Cancer in [$^{18}$F]DCFPyL PET PSMA-PET/CT hybrid imaging is a promising diagnostic platform for prostate cancer patients. While manual delineation of organs in three dimensional CT images is often needed for accurate diagnostics and treatment planning, such manual delineation is a time consuming process. To address this challenge, this example demonstrates automating the process of accurate bone segmentation in whole body CT images using deep learning approaches in accordance with the whole body segmentation technology described herein. As described in this example, the anatomical information gained via such skeletal segmentation can be used to create a fully automated lesion detection algorithm in [$^{18}$F] DCFPyL (PyL™-PSMA) PET/CT images.

A deep learning algorithm based on cascaded deep learning convolutional neural networks for semantic segmentation of 12 skeletal regions was developed. In particular, the 12 skeletal regions were the thoracic and lumbar vertebrae, sinister (left)/dexter (right) ribs, sternum, sinister (left)/dexter (right) clavicle, sinister (left)/dexter (right) scapula, sinister (left)/dexter (right) ilium, and the sacrum. A training set (N=90) and validation set (N=22) of pairs of low-dose CT images and manually crafted segmentation maps were used to develop the deep learning algorithm. The algorithm's performance was assessed on a test set (N=10) of low-dose CT images obtained from a PyL™-PSMA study. In the test set of images, five representatively body parts: sinister (left) ilium, lumbar vertebrae, sinister (left) ribs, dexter (right) scapula, and sternum were manually segmented. These manual segmentations were used as ground truth for evaluation of the automated segmentation procedure.

The automated segmentation can be used for automated lesion detection. For example, automated lesion detection approach using a hard threshold of standard uptake value (SUV) based on PET image voxel intensities can be performed.

Sorensen-Dice scores were used to evaluate accuracy of the automated segmentation. The segmentation approach achieved a Sorensen-Dice score mean and standard deviation of 0.95 and 0.024, respectively, on the training set and a mean and standard deviation of 0.93 and 0.036, respectively, on the validation set. For the test set, mean values (with standard deviation values shown in parentheses) for each of the five regions are as follows: 0.94 (0.016) for dexter (right) clavicle, 0.90 (0.023) for sinister (left) ribs, 0.92 (0.019) for sternum, 0.94 (0.033) for lumbar vertebrae, and 0.97 (0.0033) for sinister (left) ilium. The overall mean (over all body parts) was 0.93, with a standard deviation of 0.030.

Accordingly, this example demonstrates the accuracy of a fully automated segmentation approach for 12 skeletal regions in whole body low-dose CT images and use of an automated lesion detection approach for PyL™-PSMA/CT hybrid imaging.

iii. Example 3: Automated Whole Body Segmentation for PyL™-PET Image Analysis and Lesion Detection This example demonstrates automated segmentation of 49 bones and 27 soft-tissue regions in whole body CT images using deep learning approaches in accordance with the whole body segmentation technology described herein. This example also demonstrates how the anatomical information gained via such segmentation can be used to create a fully automated lesion detection algorithm in [$^{18}$F]DCFPyL (PyL™-PSMA) PET/CT images. This example also shows how the segmentation can be used to remove background signal from PET images to facilitate observation and detection of lesions in which PyL™ has accumulated.

Figure 6A:
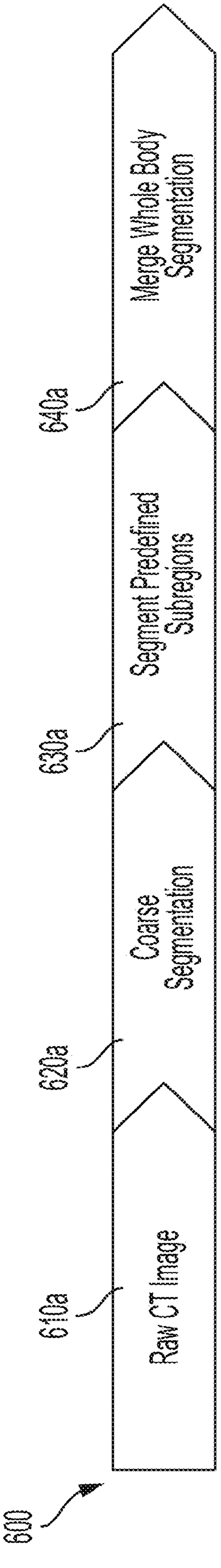
FIG. 6A is a block flow diagram of a process for automatically processing CT images for whole-body segmentation, according to an illustrative embodiment.

FIG. 6A shows a block flow diagram illustrating an embodiment of the segmentation processes described herein that is used in the PyL™-PET/CT image analysis described in this example. As in process 500, shown in FIG. 5, in process 600 an anatomical image is received. In particular, in process 600, a CT image is received 610*a*. In this example, process 600 is used to identify and segment the CT image into target volumes of interest corresponding to 49 specific bones and 8 soft tissue regions (in this example, example version 3 of the CNN-based segmentation approach described in Example 1 is used). In order to identify the target volumes, a coarse segmentation is performed 620*a* to localize a set of initial volumes of interest, or sub-regions, e.g., as described in Example 1. A fine segmentation is then performed within each of the sub-regions to identify the specific target volumes of interest that correspond to the target 49 bone and 8 soft-tissue regions 630*a*. Segmentation masks representing the identified target volumes can be created, and merged 640*a*, for example to create a 3D whole body segmentation map.

As noted in Example 1 (CNN Network Version 3), the specific regions segmented are as follows:

| 49 Bones: |
|---|
| clavicle_left |
| clavicle_right |
| hip_bone_left |
| hip_bone_right |

-continued

| |
|---|
| rib_left_1 |
| rib_left_10 |
| rib_left_11 |
| rib_left_12 |
| rib_left_2 |
| rib_left_3 |
| rib_left_4 |
| rib_left_5 |
| rib_left_6 |
| rib_left_7 |
| rib_left_8 |
| rib_left_9 |
| rib_right_1 |
| rib_right_10 |
| rib_right_11 |
| rib_right_12 |
| rib_right_2 |
| rib_right_3 |
| rib_right_4 |
| rib_right_5 |
| rib_right_6 |
| rib_right_7 |
| rib_right_8 |
| rib_right_9 |
| sacrum_and_coccyx |
| scapula_left |
| scapula_right |
| sternum |
| vertebra_lumbar_1 |
| vertebra_lumbar_2 |
| vertebra_lumbar_3 |
| vertebra_lumbar_4 |
| vertebra_lumbar_5 |
| vertebra_thoracic_1 |
| vertebra_thoracic_10 |
| vertebra_thoracic_11 |
| vertebra_thoracic_12 |
| vertebra_thoracic_2 |
| vertebra_thoracic_3 |
| vertebra_thoracic_4 |
| vertebra_thoracic_5 |
| vertebra_thoracic_6 |
| vertebra_thoracic_7 |
| vertebra_thoracic_8 |
| vertebra_thoracic_9 |
| 8 Soft-Tissue Regions: |
| gall_bladder |
| kidney_left |
| kidney_right |
| liver |
| lung_left |
| lung_right |
| prostate |
| urinary_bladder |

Figure 6B:
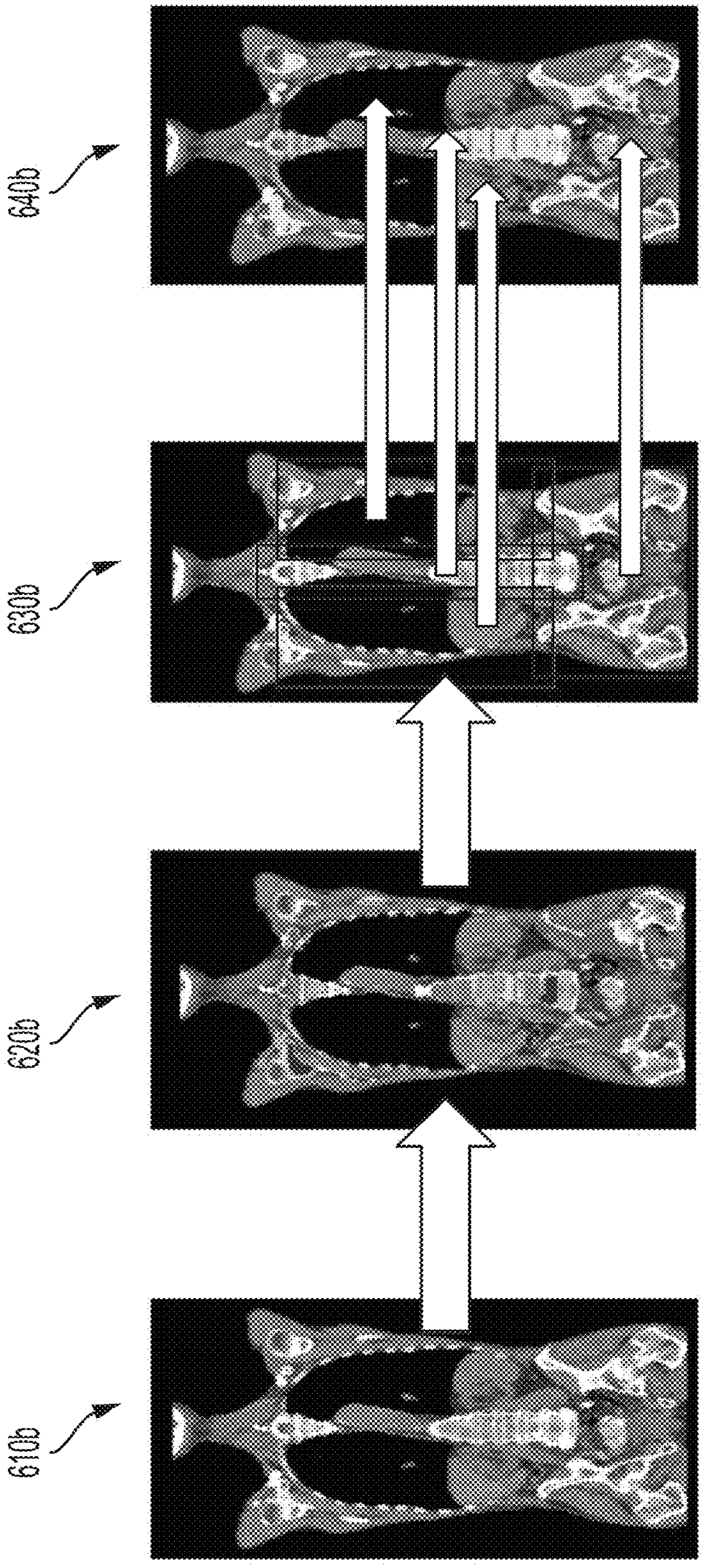
FIG. 6B is a set of CT images showing processing results of various steps of the process shown in FIG. 6A.

FIG. 6B shows a series of CT images overlaid with annotations illustrating the steps in the whole-body segmentation process 600 described in this example. An example raw CT image that is received at step 610*a* is shown in 610*b*. Image 620*b* shows results of a coarse segmentation (different regions identified are shown as colored regions) used to identify the initial volumes of interest in the CT image. Image 630*b* shows "bounding boxes" identifying initial volumes of interest in which fine segmentation is performed to identify the target volumes of interest corresponding to the 49 bones and 8 soft tissue regions. Image 640 illustrates the final, merged whole body segmentation.

Figure 8:
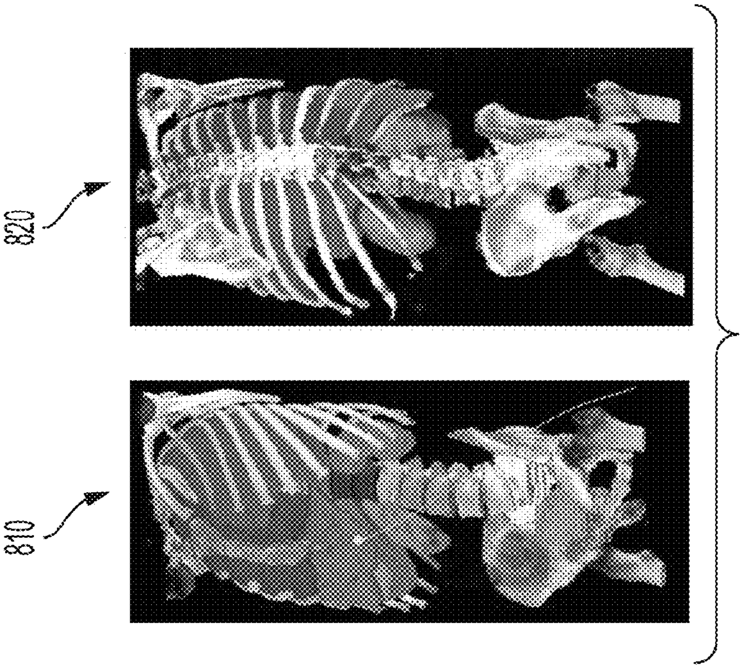
FIG. 8 is a set of two images with identified volumes of interest overlaid.
Figure 7:
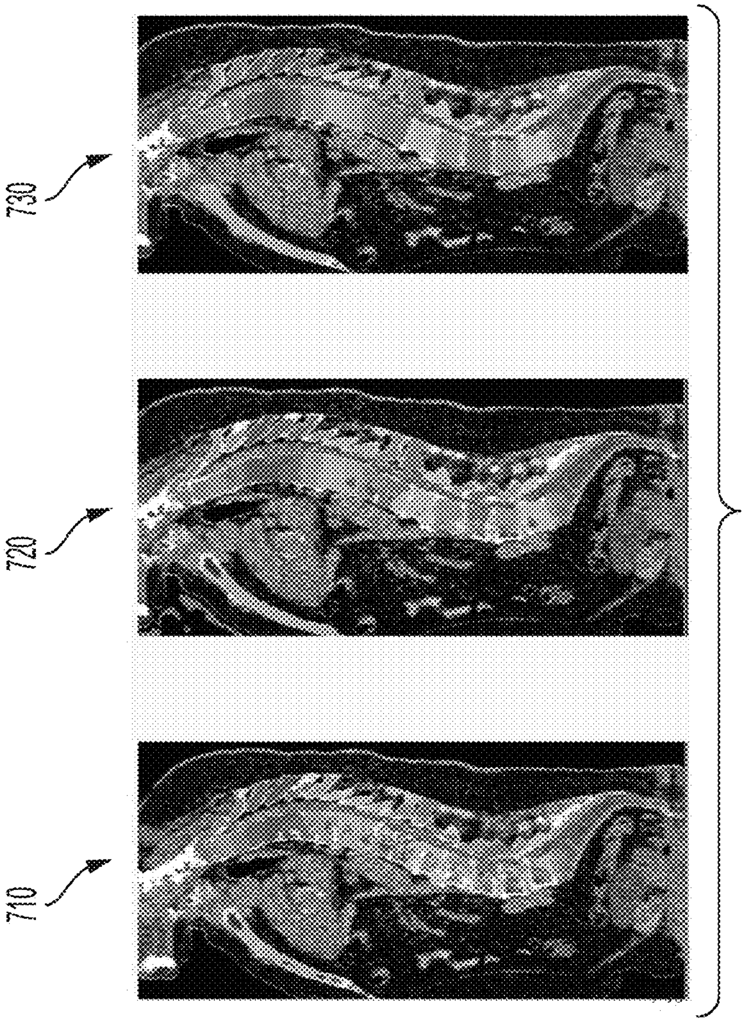
FIG. 7 is a set of three images used as training data for machine learning modules used to segment CT images, according to an illustrative embodiment.
Figure 16B:
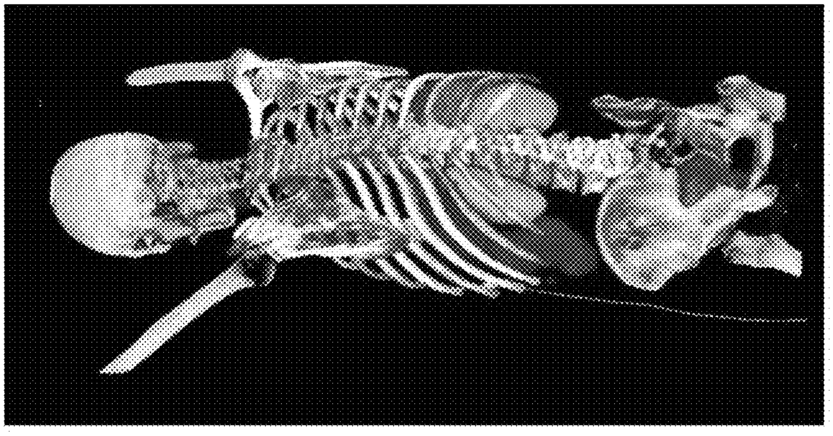
FIG. 16B is another view of the 3D CT image with identified volumes of interest overlaid shown in FIG. 16A.
Figure 16A:
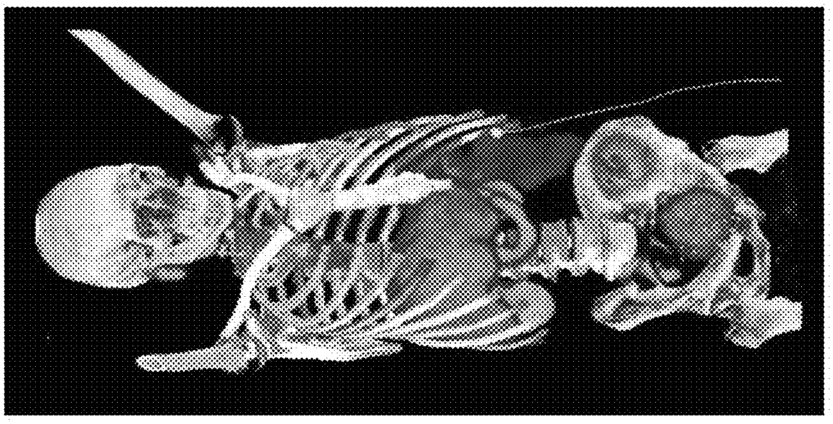
FIG. 16A is a view of a 3D CT image with identified volumes of interest overlaid.

Turning to FIG. 7, in order to train the machine learning modules used to perform the segmentations, numerous pre-labeled sample images, such as the three images (710, 720, 730) shown in FIG. 7, were used as a training data set. The machine learning modules were fine-tuned using 1000's of manually annotated labels along with 100's of models trained on dozens of GPUs over 1000's of hours before optimal configurations for the many components of the segmentation platform were discovered. Once trained, however, segmentation can be performed rapidly, with results such as those shown in FIGS. 8 (810 and 820 are two example images) and FIGS. 16A and 16B obtained in a matter of seconds—typically under 180 seconds.

Figure 9A:
FIG. 9A is a set of 2D views of a 3D PET/CT image obtained from a subject following administration of PyL™.
Figure 9B:
FIG. 9B is the same set of 2D views shown in FIG. 9A, following background correction.
Figure 9C:
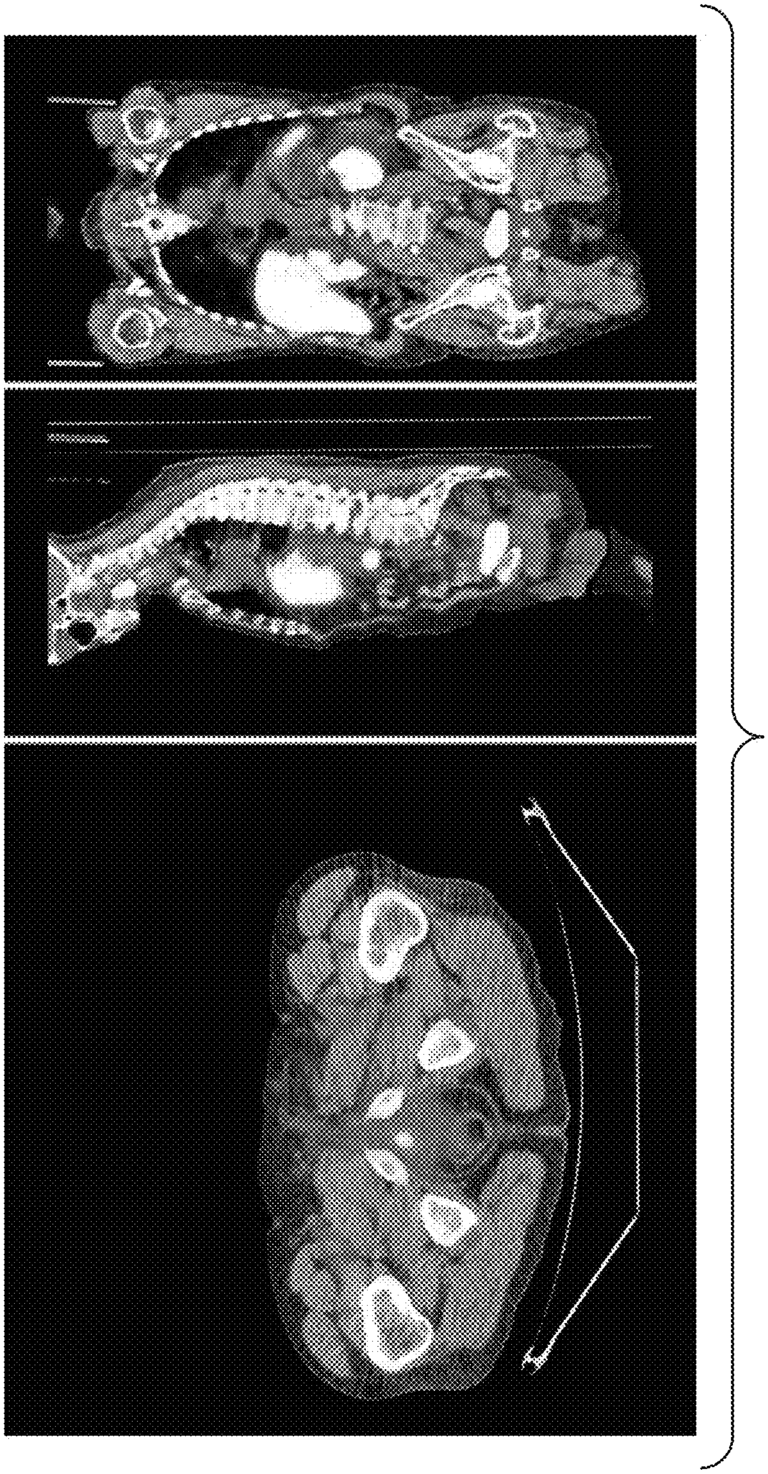
FIG. 9C is a set of 2D views of a 3D PET/CT image obtained from a subject following administration of PyL™.
Figure 9D:
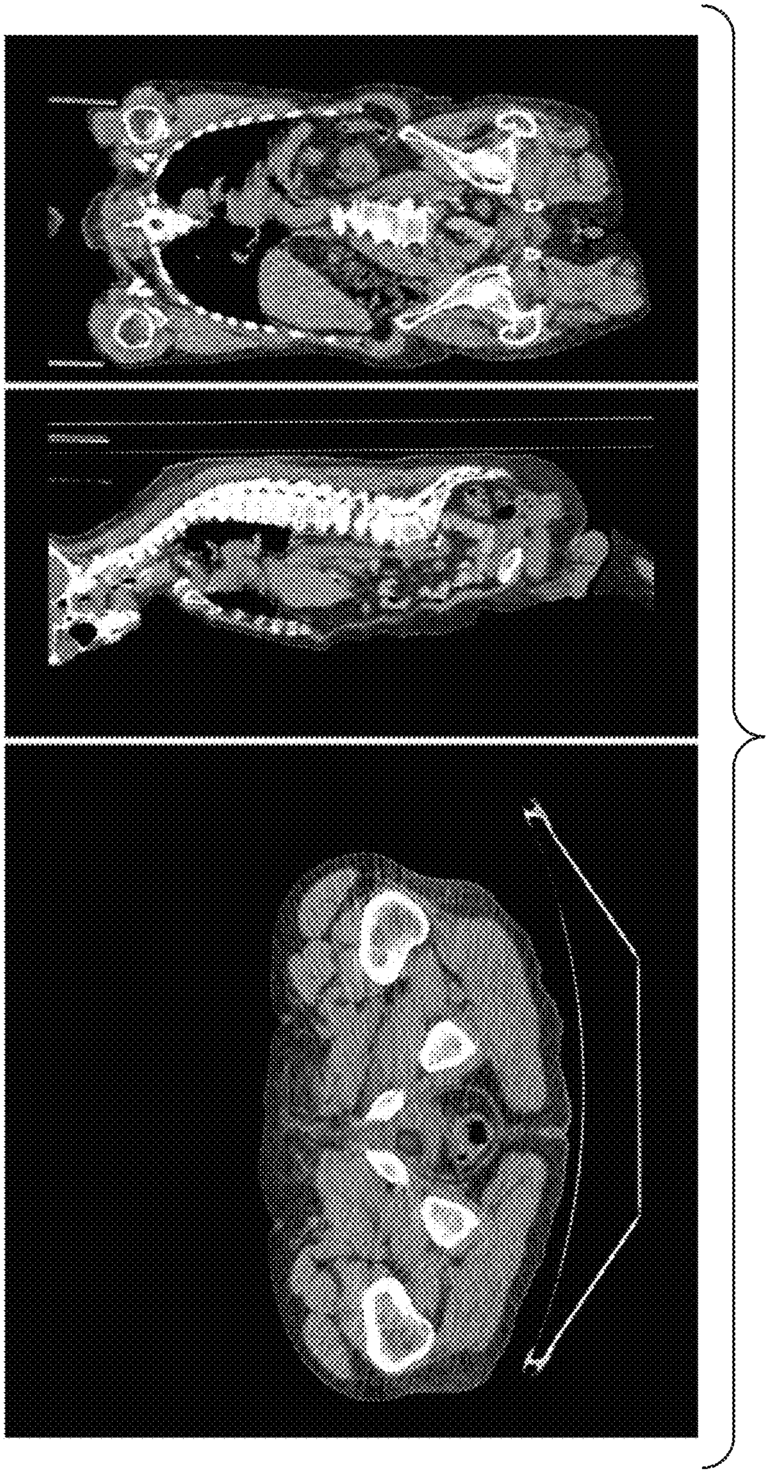
FIG. 9D is the same set of 2D views shown in FIG. 9C, following background correction.

The anatomical context obtained by segmenting the CT image can be used to detect lesions in PET images that are co-registered with the CT image, for example, as in a typical PET/CT imaging modality in which CT and PET images are obtained for a subject in quick succession, with the subject remaining in a substantially same position as the images are recorded. In particular, as demonstrated in this example, segmentation of the CT image can be transferred to the PET image in order to identify regions of interest such as the prostate gland or the skeleton, where the entire functional image except for regions expected to carry either primary or secondary prostate cancer tumors can be excluded from the lesion detection algorithm. Without wishing to be bound to any particular theory, exclusion of regions from the lesion detection algorithm can be especially important for background regions where accumulation leads to high intensity in PET image voxels within and around the background tissue regions. The high intensities in background tissue regions may, if not excluded from the prostatic lesion detection process, lead to erroneous classification of background noise as cancerous lesions. In the regions that remain after the background exclusion process, a simple threshold (e.g., a SUV of 3) in conjunction with a lesion classification algorithm can be employed to find hotspots within the relevant tissue regions. The classification algorithm may be used as a simple check to confirm the hotspots position and to compare the intensity in the hotspot's neighborhood. If the hotspot is part of a larger hotspot and is located on the edge of a body part (e.g. a rib close to the liver), the lesion may be classified as noise and excluded. FIGS. 9A-D illustrate the need for, and benefits obtained by, this background subtraction approach and lesion detection algorithm, where only regions of interest are included in the detection procedure, and portions of the image contains high intensity background voxels. FIGS. 9A and 9C show PET images as white-to-red-to-blue false color overlaid on CT images. Blue color indicates low PET image intensity, transitioning from red to white as intensity increases. FIGS. 9B and 9D show the same PET images as in 9A and 9C, but with all background uptake removed from the PET image. In FIGS. 9B and 9D, a few localized hotspots, corresponding to cancerous lesions are visible. In the PET images without background removal, these hotspots were overwhelmed and masked by the large background signal.

Figure 10A:
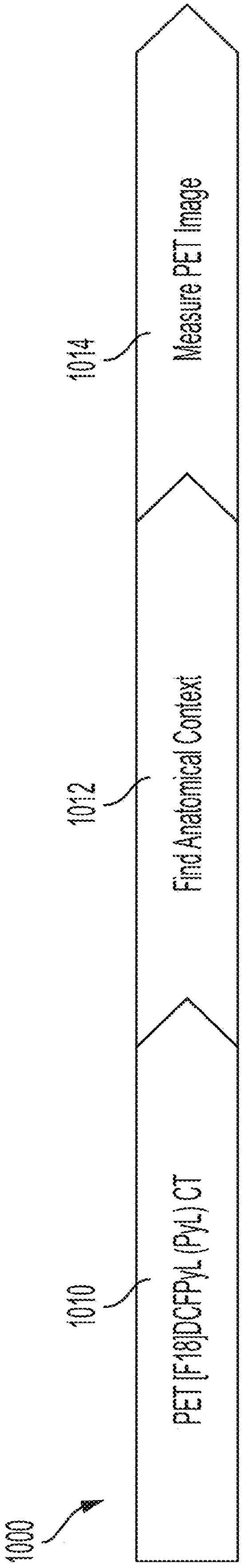
FIG. 10A is a block flow diagram showing an example process for analyzing PyL™-PET images, according to an illustrative embodiment.
Figure 10B:
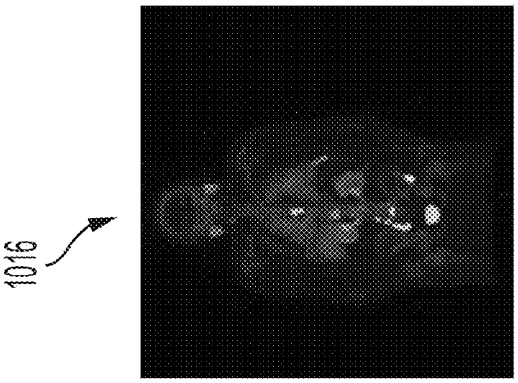
FIG. 10B is a PET/CT image obtained following administration of PyL™ to a subject.
Figure 10C:
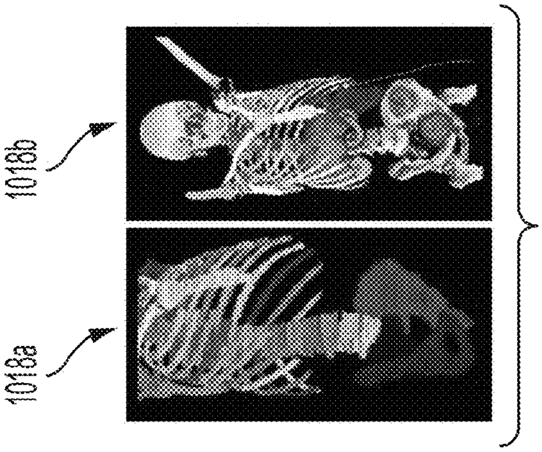
FIG. 10C is a set of two CT images showing volumes of interest identified via the machine learning approaches described herein.
Figure 10D:
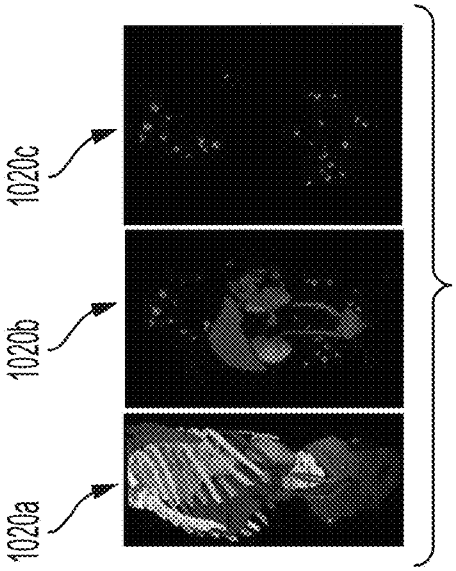
FIG. 10D is a set of 3 images illustrating background correction in PET images, according to an illustrative embodiment.

FIG. 10A shows an example process 1000 for using the anatomical context provided by whole body CT segmentation for detecting lesions and determining useful risk indices that quantify a cancer status (e.g., prostate cancer status) of a subject using PET/CT images obtained following administration of PyL™ as a radiopharmaceutical. As shown in FIG. 10A, PET/CT images are obtained 1010, anatomical context is determined 1012 via segmentation of bones and soft tissue and used to obtain measurements (e.g., of lesions and/or risk indices) from the PET image 1014. FIG. 10B shows an example PET/CT image 1016 and FIG. 10C shows example segmentations of bones and soft tissue 1018*a* and 1018*b*. As shown in FIG. 10D, segmentation of bone and soft-tissue (e.g., shown in image 1020*a*) can be used to remove background signal (e.g., from background tissue regions, such as those shown in image 1020*b*), leaving only desired signal from hotspots indicative of cancerous lesions 1020*c*.

Figure 11B:
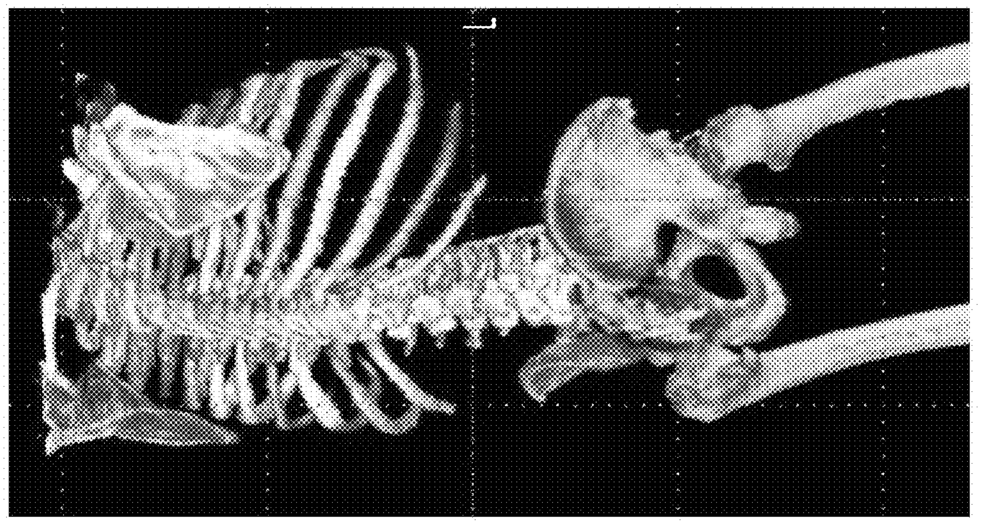
FIG. 11B is another view of the 3D CT image with labeled volumes of interest shown in FIG. 11A.
Figure 11A:
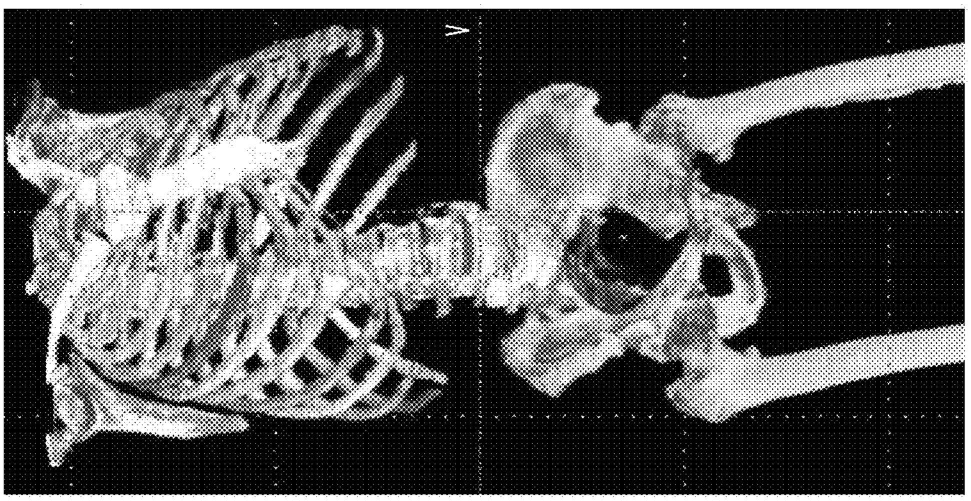
FIG. 11A is a view of a 3D CT image with volumes of interest corresponding to specific bones labeled in color, according to an illustrative embodiment.
Figure 12:
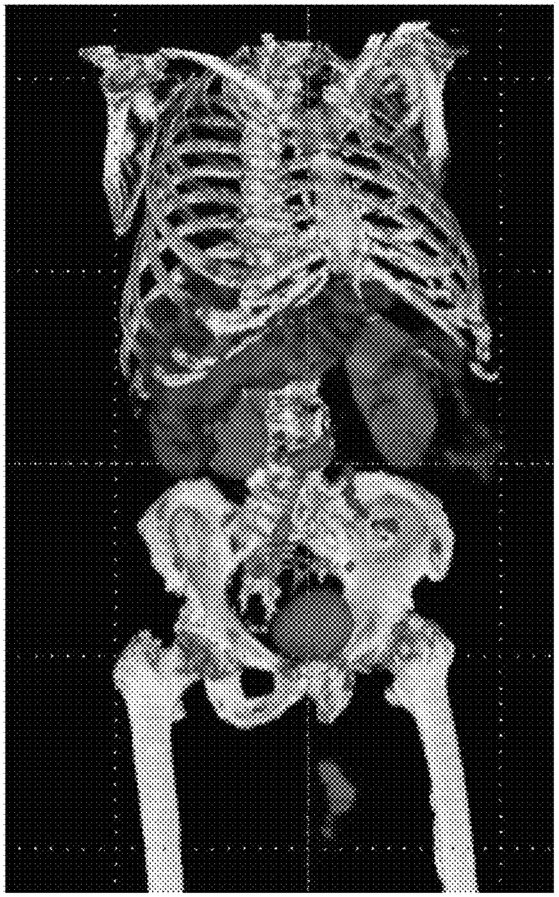
FIG. 12 is a CT image with an overlaid PET image showing identified background tissue regions.

FIGS. 11-13 illustrate this process, showing how segmentation of a CT image can be transferred to a PET image, and are used to provide anatomical context for background removal and lesion detection. In particular, FIG. 11A and FIG. 11B show different views of a CT image, in which segmentation of bones has been performed. The various segmented bones are labeled with different colors in the views shown in FIG. 11A and FIG. 11B. Notably, by virtue of the "bounding box" approach described herein, even such a complex and large scale segmentation can be performed extremely rapidly. The segmentation shown in FIGS. 11A and 11B was performed in less than 180 seconds.

Figure 13A:
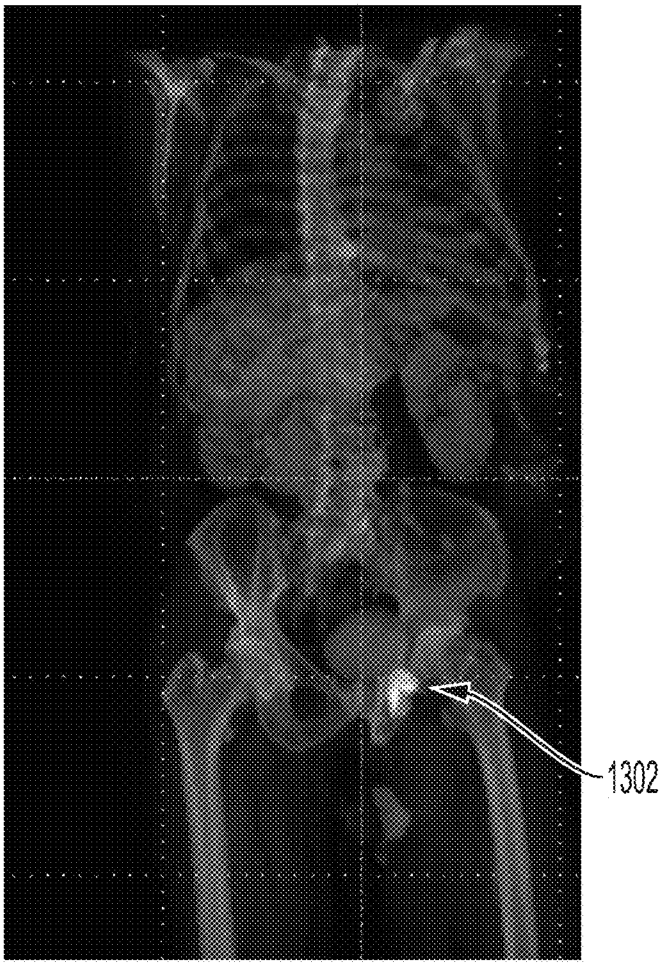
FIG. 13A is view a CT image with an overlaid PET image showing a detected lesion.
Figure 13B:
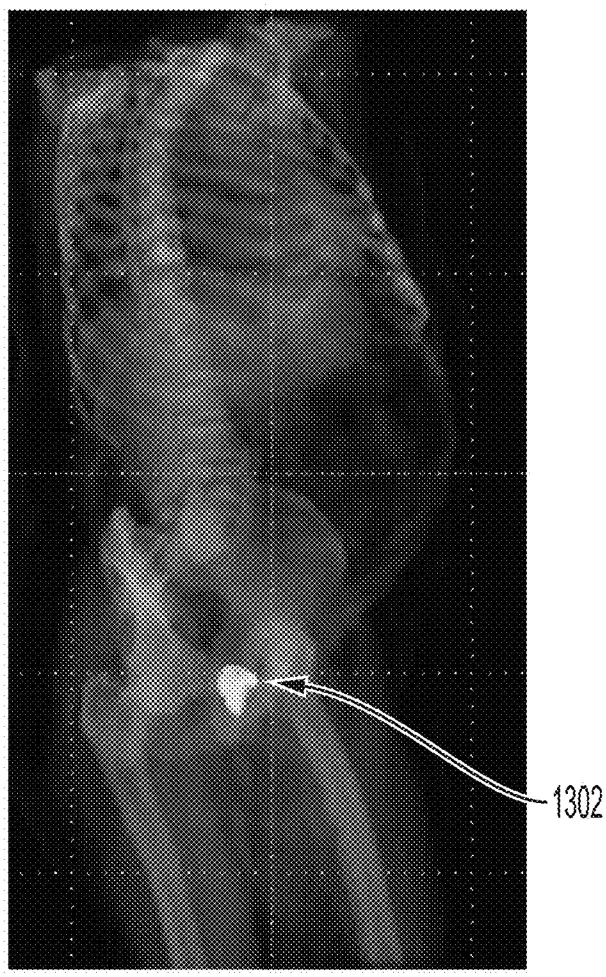
FIG. 13B is another view of the CT image with overlaid PET image of FIG. 13A, showing the detected lesion.
Figure 13C:
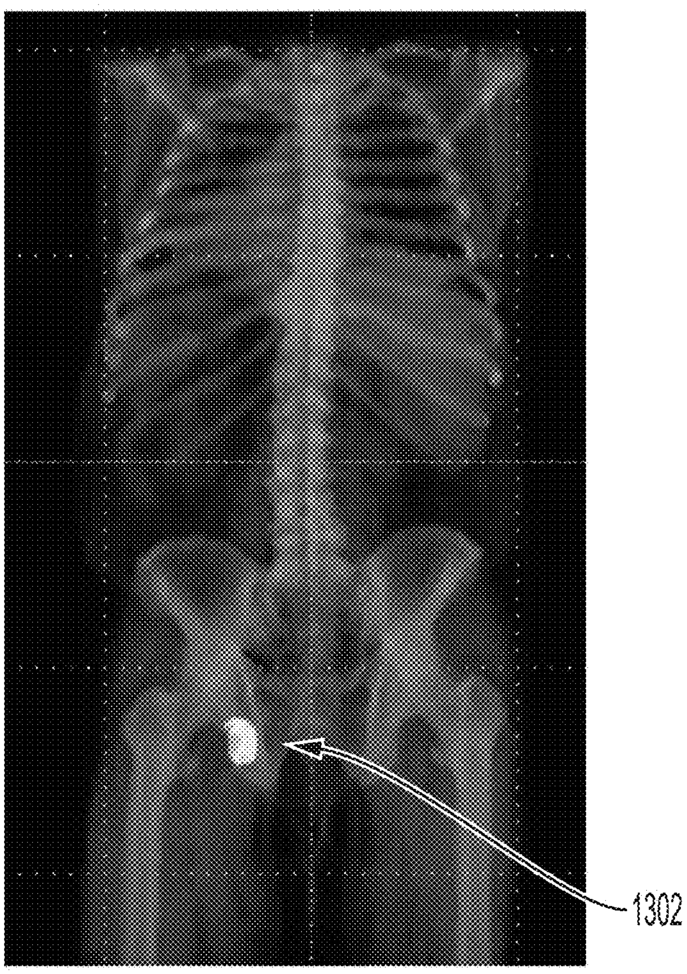
FIG. 13C is another view of the CT image with overlaid PET image of FIG. 13A, showing the detected lesion.
Figure 13D:
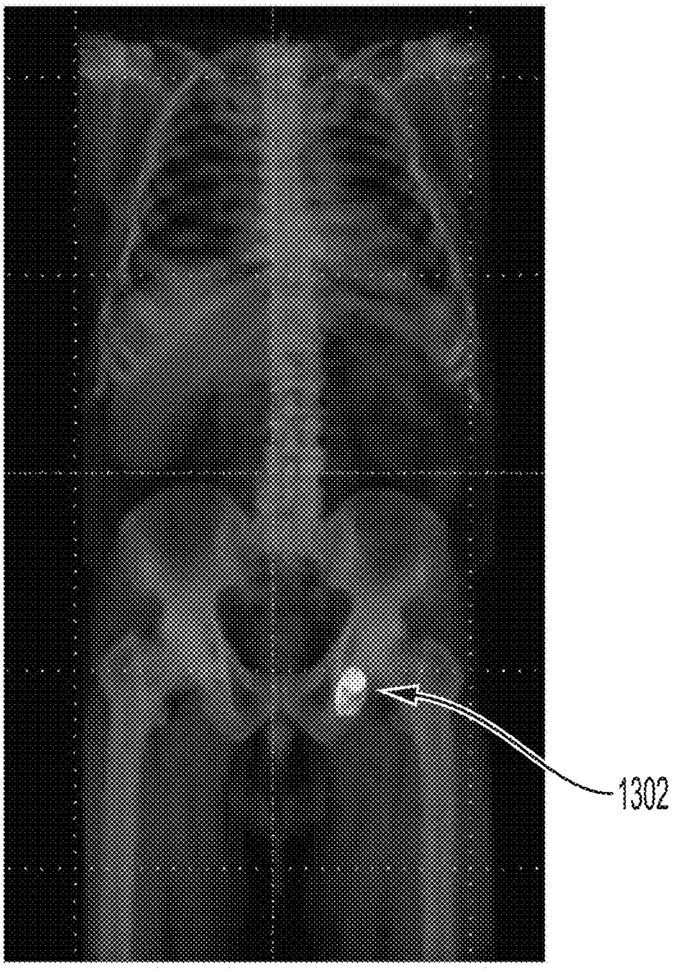
FIG. 13D is another view of the CT image with overlaid PET image of FIG. 13A, showing the detected lesion.

As shown in FIG. 12, segmentation of bones and soft tissue can be used to account for normal uptake in certain background tissue regions, which may occur under normal circumstances and mask useful hotspot signals that indicate presence of cancerous lesions. In PET/CT imaging performed with PyL™, normal uptake can occur in kidneys, duodenum, small intestines, spleen, liver, pancreas, stomach, adrenal gland, rectum, and testes. FIG. 12 shows the aforementioned regions identified in red. As shown in FIG. 13A, once background intensities due to normal PyL™ accumulation in these regions is subtracted out, lesions become readily observable and can be detected. One such lesion 1302 is visible in FIGS. 13A-D. Lesions such as lesion 1302 can be detected, for example via a thresholding approach, and classified as PyL™ positive (i.e., indicative of cancer) e.g., as described above. As with segmentation, lesion detection is also rapid. Lesion 1302 was detected in less than 5 seconds.

Figure 14B:
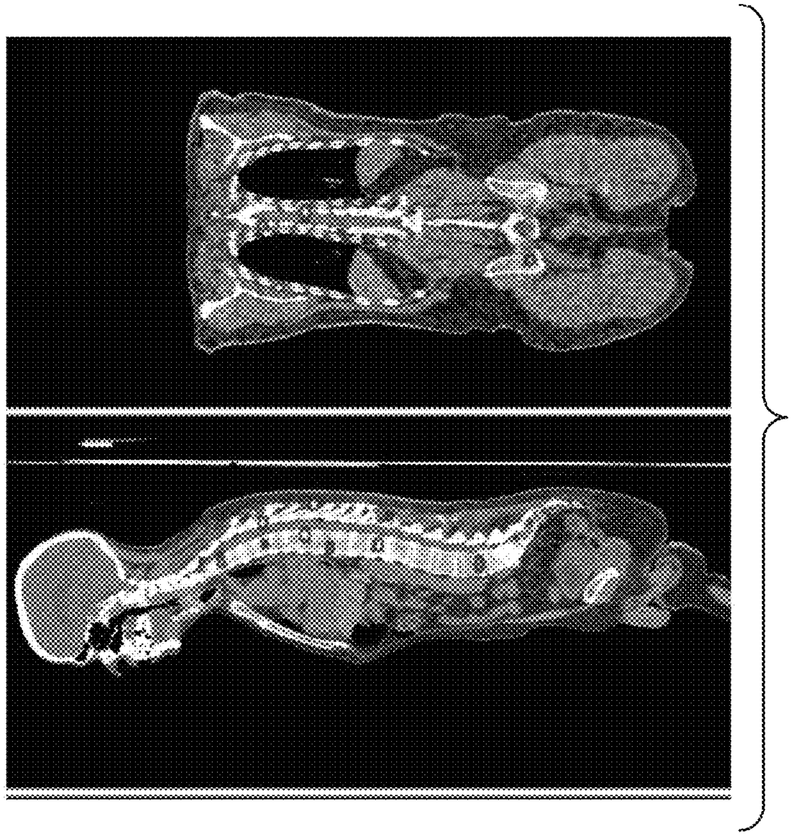
FIG. 14B shows the same views as FIG. 14A, but following processing via the machine learning approaches described herein to provide for background correction and detection of lesions.
Figure 14A:
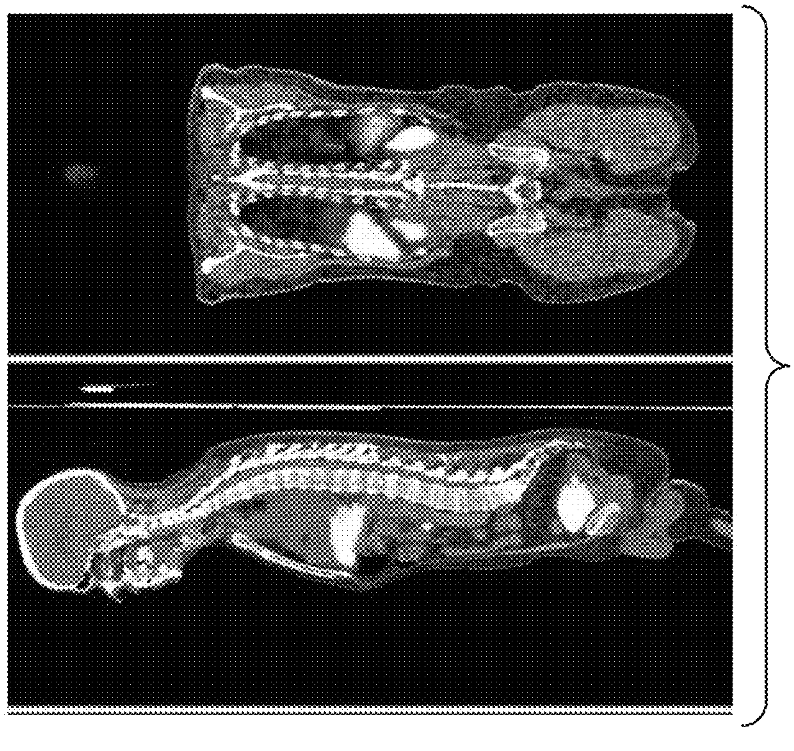
FIG. 14A is a set of two views of a CT image with an overlaid PET image obtained for a subject following administration of PyL™.

FIG. 14A and FIG. 14B show results of the PET image processing and lesion detection approach described above performed on PET/CT images obtained for a 65 year old male with metastatic castration resistant prostate cancer. The patient's prostate specific antigen (PSA) score was 6.8 ng/ml. The PET images were obtained following administration of PyL™ as the radiopharmaceutical. FIG. 14A shows the initial, raw, PET/CT image. FIG. 14B shows the image following the processing described herein. The background intensity is removed, and several small lesions are readily observable. The segmentation of the 49 bones and 8 soft-tissue regions (e.g., organs) was performed in less than 180 seconds.

Figure 15B:
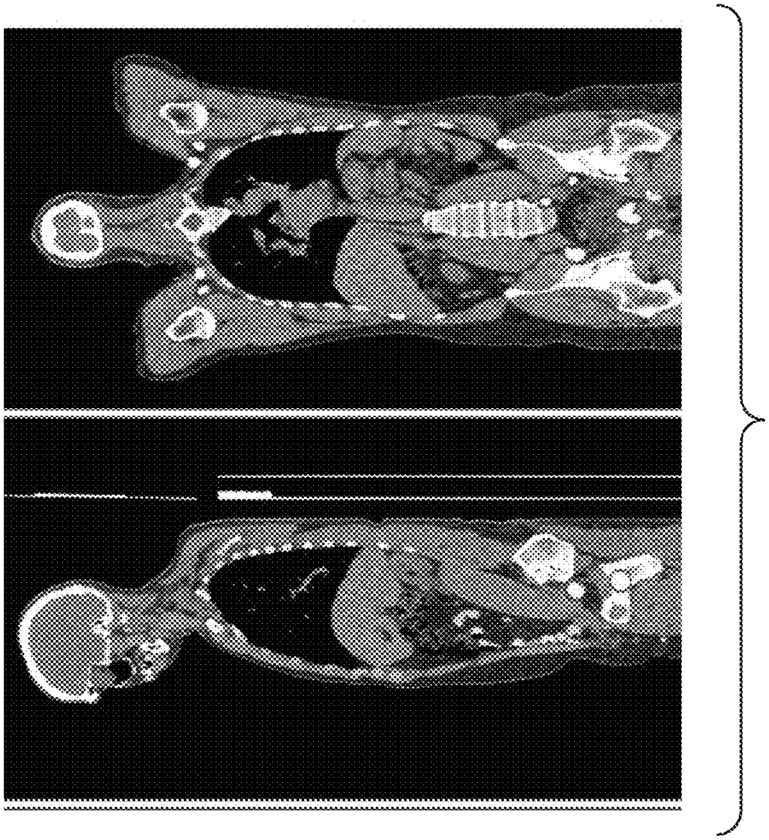
FIG. 15B shows the same views as FIG. 15A, but following processing via the machine learning approaches described herein to provide for background correction and detection of lesions.
Figure 15A:
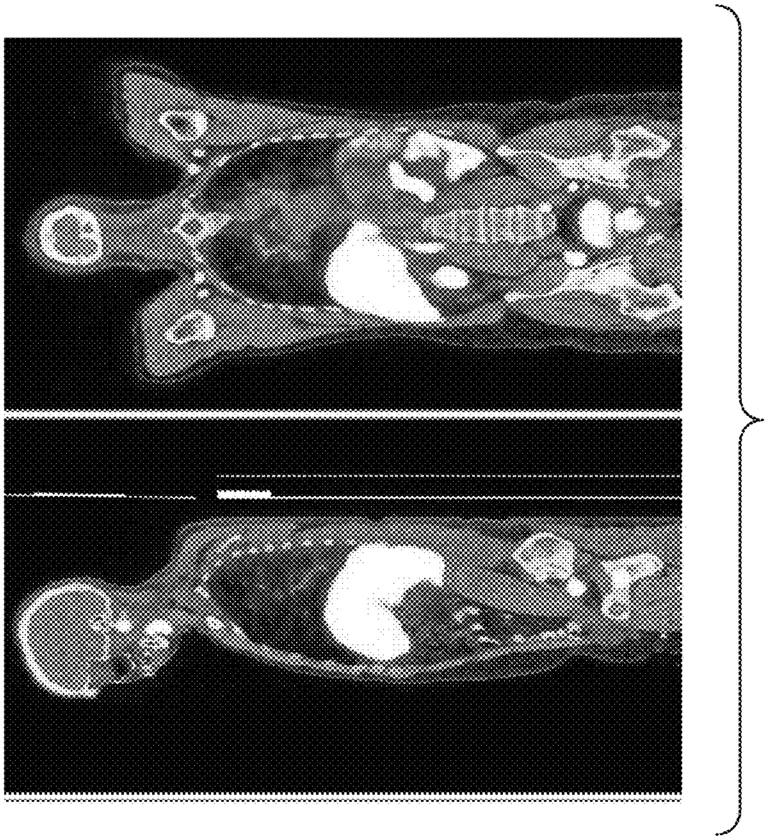
FIG. 15A is a set of two views of a CT image with an overlaid PET image obtained for a subject following administration of PyL™.

FIG. 15A and FIG. 15B show results of the PET image processing and lesion detection approach performed on PET/CT images obtained for a 54 year old male with metastatic castration resistant prostate cancer. The patient's PSA score was 33.55 ng/ml. The PET images were obtained following administration of PyL™ as the radiopharmaceutical. FIG. 15A shows the initial, raw, PET/CT image. FIG. 15B shows the image following the processing described herein. The background intensity is removed, and several small lesions are readily observable. The segmentation of the 49 bones and 8 soft-tissue regions (e.g., organs) was again performed in less than or about 180 seconds.

Accordingly, this example demonstrates how the whole-body segmentation approach described herein contextualizing the PyL™ images, with automated segmentation of 27 soft-tissue organs and 49 bones, to detect, quantify and track PyL™ avid lesions. The approach would allow the clinicians/physicians to ask clinically relevant questions for better management of prostate cancer patients. Advantages such as increased diagnostic accuracy, precision, speed, and reproducibility, were demonstrated (statistically) in the context of artificial intelligence assisted 1404-SPECT image analysis (see, e.g., PCT Publication WO2019/136349, the content of which is hereby incorporated by reference in its entirety), may also be obtained for PyL™-PET images.

iv. Example 4: Example Bone and Soft-Tissue Segmentation Regions

This example provides a listing of a set of example bone and soft-tissue regions that a system developed using the approaches and embodiments described herein can identify via segmentation of CT images. In particular, listed below are 67 bones and 22 soft-tissue regions for that have been manually labeled (e.g., identified by one or more human experts) in a set of CT images. These manually labeled CT images can be used as training data for the machine learning approaches described herein. For example, while Examples 1-3 describe current versions of software implementing whole body segmentation approaches that segment 49 bones and 8 soft-tissue regions, their functionality can readily be updated to segment any number of the 67 bone and 22 soft-tissue regions listed in this example. Accordingly, this example shows that embodiments of the systems and methods described herein may be developed to identify similar regions, including, but not necessarily limited to the specific regions described in this example. Certain systems and methods may identify tissue regions not necessarily listed in this example. In certain embodiments, both bone and soft-tissue regions are identified. In certain embodiments, some systems and methods may identify only bones, or only soft-tissue.

As indicated in the listing below, certain left and right hand side bones are identified as separate tissue regions (e.g., a left clavicle and a right clavicle) and, in certain cases, individual members of large groups of bones are identified separately. For example, the example listing below shows that individual ribs and vertebrae are identified via the segmentation approach of this example (specific ribs and vertebrae are numbered in the listing). This example also should make clear that the approaches described herein can be used to segment a variety of regions throughout the body, including, but not necessarily limited to the regions listed herein.

| Segementation regions: |
| --- |
| Bones (67) |
| clavicle_left |
| clavicle_right |
| femur_left |
| femur_right |
| fibula_left |
| fibula_right |
| hip_bone_left |
| hip_bone_right |
| humerus_left |
| humerus_right |
| mandible |
| patella_left |
| patella_right |
| radius_left |
| radius_right |
| rib_left_1 |
| rib_left_2 |
| rib_left_3 |
| rib_left_4 |
| rib_left_5 |
| rib_left_6 |
| rib_left_7 |

-continued

| Segementation regions: |
| --- |
| rib_left_8 |
| rib_left_9 |
| rib_left_10 |
| rib_left_11 |
| rib_left_12 |
| rib_right_1 |
| rib_right_2 |
| rib_right_3 |
| rib_right_4 |
| rib_right_5 |
| rib_right_6 |
| rib_right_7 |
| rib_right_8 |
| rib_right_9 |
| rib_right_10 |
| rib_right_11 |
| rib_right_12 |
| sacrum_and_coccyx |
| scapula_left |
| scapula_right |
| skull |
| sternum |
| tibia_left |
| tibia_right |
| ulna_left |
| ulna_right |
| vertebra_cervical_all |
| vertebra_lumbar_1 |
| vertebra_lumbar_2 |
| vertebra_lumbar_3 |
| vertebra_lumbar_4 |
| vertebra_lumbar_5 |
| vertebra_lumbar_6 |
| vertebra_thoracic_1 |
| vertebra_thoracic_2 |
| vertebra_thoracic_3 |
| vertebra_thoracic_4 |
| vertebra_thoracic_5 |
| vertebra_thoracic_6 |
| vertebra_thoracic_7 |
| vertebra_thoracic_8 |
| vertebra_thoracic_9 |
| vertebra_thoracic_10 |
| vertebra_thoracic_11 |
| vertebra_thoracic_12 |
| Soft tissue (22): |
| adrenal_gland_left |
| adrenal_gland_right |
| aorta_abdominal_part |
| aorta_thoracic_part |
| brain |
| bronchi_left |
| bronchi_right |
| gallbladder |
| gluteus_maximus_left |
| gluteus_maximus_right |
| heart |
| kidney_left |
| kidney_right |
| liver |
| lung_left |
| lung_right |
| pancreas |
| prostate |
| rectum |
| spleen |
| urinary_bladder |
| ventricle |

v. Example 5: Computing Hotspot Indices for Radiopharmaceutical Uptake Quantification and Clinical Endpoint Assessment Example 5 is an example approach that uses the segmentation and hotspot detection methods described herein to compute, for a particular detected hotspot, a hotpot index value that can be used to infer and/or quantify uptake of radiopharmaceutical within the lesion that the detected hotspot represents. The computed hotspot index can be related to clinical endpoints, including survival rate of a patient and to determine treatment strategy. When computed for multiple images, collected at different time points, the computed index values can be compared with each other for a particular patient, and the change in index used to evaluate efficacy of a treatment and to make a prognosis of how the index will change in the near future. In certain embodiments, the computed index can predict sensitivity towards treatment targeting the imaging-ligand. In certain embodiments, the computed index can also be included in nomograms for effective patient stratification.

The approach in this example uses a CT-PET image set obtained for a particular patient following administration of a radiopharmaceutical comprising a PSMA binding agent, for example, PyL™. However, the approaches described herein are agnostic to the particular radiopharmaceutical used for imaging, and can be utilized with a variety of different radiopharmaceuticals, e.g., $^{99m}$Tc-MIP-1404, $^{18}$F-PyL, $^{68}$Ga-PSMA-11, $^{18}$F—NaF, $^{11}$C-Choline, [18F]FDG, [18F]FACBC, etc.

A machine learning-based approach in accordance with the systems and methods described herein is used to identify various target VOIs within the CT image. As described herein, the target VOIs are volumes in the CT image identified, automatically, by the segmentation approach, to correspond particular target tissue regions. In this example approach, target VOIs corresponding to a liver, an aorta portion, and a parotid gland are identified. As described herein, these particular tissue regions—the liver, aorta portion, and parotid gland—serve as reference regions for computation of the hotspot index. Other target VOIs corresponding to other target tissue regions, in addition to the reference regions, may also be identified. Segmentation masks representing the identified target VOIs are mapped to the PET image to identify corresponding 3D volumes within the PET image. In this manner, 3D reference volumes corresponding to the liver, aorta portion, and parotid gland are identified in the PET image. Once identified, each particular 3D reference volume is used to compute a corresponding reference intensity value that provides a measure of the intensities of voxels within the particular 3D reference volume. In this example, a mean intensity inside each volume is used, though other measures (e.g., a median, a maximum, a mode, etc.) are possible.

To compute an index value for a particular identified hotspot, a hotspot intensity value is computed for that particular hotspot and compared with the reference intensity values. Similar to the reference values, the hotspot intensity value provides a measure of intensity of voxels of the hotspot. In this example, a maximum value is computed, although, as with the reference values, other measures can be used. As this example shows, the particular measure used to compute the hotspot intensity value need not be the same as that used to compute the reference intensity values. To compute the hotspot index value, the reference intensity values can be mapped to reference index values on a scale, and the hotspot index value can then be computed based on whether the hotspot intensity value lies above, below, or in between the reference values.

For example, typically the reference intensity value computed from the reference volume corresponding to the aorta portion (this—aorta—region is used to provide a measure of uptake in the blood pool, and may also be referred to as a blood or blood pool reference value) is lowest in value, followed by the liver and then the parotid region. Accordingly, a hotspot whose hotspot intensity value is equal to the blood reference value will be assigned a hotspot index value equal to 100; a hotspot whose hotspot intensity value is equal to the liver reference value will be assigned a hotspot index value equal to 200; and a hotspot whose hotspot intensity value is equal to the parotid gland reference value will be assigned a hotspot index value equal to 300. Hotspot index values for hotspot intensity values lying in between two reference intensity values can be determined via interpolation (e.g., linear interpolation).

In this manner, a detected hotspot can be assigned an index value that quantifies, in a standardized fashion (e.g., so as to be comparable between different images) a level of radiopharmaceutical uptake in the particular lesion that the hotspot represents. As described herein, these indices can be related to survival, which, in turn, makes them useful for treatment management. For example, depending on the expected outcome of the patient, a more or less aggressive treatment may be considered. Price of treatments can also be included as a factor. The index is especially useful when measured over time. When comparing indices across time and multiple imaging examinations for a patient, the change in index can be used to evaluate the efficacy of a treatment, and to make a prognosis how the index will change in the near future.

Notably, a significant advantage of the approach described in this example over previous approaches is the ability to compute reference intensity values (as well as hotspot intensity values) from automatically identified 3D volumes provided by the artificial intelligence based segmentation approaches described herein. Previous approaches that attempted to quantify regions of images representing lesions relied on hand marking—e.g., via placement of a circular marker—of regions in 2D slices to identify 2D regions of interest lying within a reference tissue region. In contrast to such small 2D regions, the 3D volume that are identified via the approaches used herein capture intensities throughout entire organs, and thereby offer increased accuracy and repeatability. Moreover, by using accurate automated segmentation, further increases in accuracy and repeatability are provided.

In addition, rather than classifying a detected lesion using one of a small number of values, the approach of this example uses a continuously varying index computed via interpolation. This approach provides more detailed information that can be utilized to manage treatment strategy and track disease progression and/or treatment efficacy over time in a finely grained and accurate fashion.

vi. Example 6: Automated Hotspot Detection and Uptake Quantification in Bone and Local Lymph PyL™-PSMA PET/CT hybrid imaging (e.g., images PET/CT images acquired for a patient after administering PyL™ to the patient) is a promising tool for detection of metastatic prostate cancer. Image segmentation, hotspot detection, and quantification technologies of the present disclosure can be used as a basis for providing automated quantitative assessment of abnormal PyL™-PSMA uptake in bone and local lymph (i.e., lymph nodes localized within and/or in substantial proximity to a pelvic region of a patient). In particular, as shown in this example, image segmentation and hotspot detection techniques in accordance with the systems and methods described herein can be used to automatically analyze in PET images to detect hotspots that a physician might identify as malignant lesions.

In this example, PET/CT scans were evaluated to automatically identify, within the PET images of the scans, hotspots corresponding to potential bone and local lymph node lesions. For each scan, a semantic segmentation of the CT image was performed using the deep learning approaches described herein in order to identify a set of specific bone and soft-tissue regions (e.g., organs). Once obtained, the CT image segmentation was transferred (e.g., mapped) to the PET image of the PET/CT scan to identify corresponding 3D volumes in the PET image. In each PET image, intensities corresponding to background uptake were removed by suppressing intensities in identified volumes corresponding to a urinary bladder, a liver, and a kidney. The segmentation was also used to define relevant volumes in which to detect hotspots. Blob detection algorithms were then applied to identify abnormal hotspots representing either possible bone lesions or possible malignant local lymph nodes. Reference volumes corresponding to a liver and a thoracic part of an aorta were used to compute reference SUV values.

Accuracy of the hotspot detection approach in this example was validated by comparing detection of hotspots in PET images using the automated approach described herein with manual annotations identifying bone lesions and lymph node lesions from teams of physicians. A set of 157 PET/CT scans that were annotated for bone lesions (114 of the images did not have any lesions and 11 of the images had greater than three lesions) were used to evaluate accuracy in detecting hotspots corresponding to bone lesions and a set of 66 scans that were annotated for local lymph node lesions (40 images without lesions and six with greater than three lesions). The bone detection algorithm identified 97% of all annotated bone lesions, with on average 109 hotspots per image. The local lymph detection algorithm found 96% of all annotated malignant local lymph nodes, with on average 32 hotspots per scan.

Accuracy of the deep learning segmentation was also evaluated in this example. The segmentation algorithm was trained to segment a set of 52 bones and 7 soft tissue regions (e.g., organs) used either for defining the hotspot search region or as reference regions. Training and validation was performed and evaluated for each particular region (bone or soft tissue region) using a manual identification of that region in a CT image. For example, 140 manually identified livers were used to train the algorithm for liver segmentation, and 37 manually identified livers were used for validation. Similarly, 61 and 14 manually identified aortas were used for training and validation of the aorta region segmentation, respectively. For liver segmentation, Dice scores of 0.99 and 0.96 were obtained for the training and validation sets, respectively. For aorta segmentation, Dice scores of 0.96 and 0.89 were obtained for training and validation, respectively. Finally, a set of ten additional images that were not used development of the algorithm were used to assess generalization. For these ten images, Dice scores characterizing segmentation accuracy of the liver and aorta were 0.97+0.01 and 0.91+0.5, respectively.

A full listing of the specific 52 bone (the sacrum and coccyx are listed on a single line as "sacrum_and_coccyx", but correspond to two segmented regions) and 7 soft-tissue regions used in this particular example is below.

| Bone Regions: |
|---|
| capula_left |
| clavicle_left |
| clavicle_left |
| clavicle_right |
| hip_bone_left |
| hip_bone_right |
| rib_left_1 |
| rib_left_10 |
| rib_left_11 |
| rib_left_12 |
| rib_left_2 |
| rib_left_3 |
| rib_left_4 |
| rib_left_5 |
| rib_left_6 |
| rib_left_7 |
| rib_left_8 |
| rib_left_9 |
| rib_right_1 |
| rib_right_10 |
| rib_right_11 |
| rib_right_12 |
| rib_right_2 |
| rib_right_3 |
| rib_right_4 |
| rib_right_5 |
| rib_right_6 |
| rib_right_7 |
| rib_right_8 |
| rib_right_9 |
| sacrum_and_coccyx |
| scapula_left |
| scapula_right |
| sternum |
| vertebra_lumbar_1 |
| vertebra_lumbar_2 |
| vertebra_lumbar_3 |
| vertebra_lumbar_4 |
| vertebra_lumbar_5 |
| vertebra_thoracic_1 |
| vertebra_thoracic_10 |
| vertebra_thoracic_11 |
| vertebra_thoracic_12 |
| vertebra_thoracic_2 |
| vertebra_thoracic_3 |
| vertebra_thoracic_4 |
| vertebra_thoracic_5 |
| vertebra_thoracic_6 |
| vertebra_thoracic_7 |
| vertebra_thoracic_8 |
| vertebra_thoracic_9 |
| **Soft Tissue Regions:** |
| aorta_abdominal_part |
| aorta_thoracic_part |
| kidney_left |
| kidney_right |
| liver |
| prostate |
| urinary_bladder |

Accordingly, this example demonstrates use of deep learning based semantic segmentation for automated identification of hotspots and for computation of SUV reference values in [$18^F$] DCFPyL (PyL™-PSMA) PET/CT images.

vii. Example 7: Lesion PSMA Score and PSMA Weighted Lesion Involvement

This example provides an approach for assigning detected hotspots hotspot indices, based on a comparison of individual hotspot intensities with reference levels, and then using the assigned individual hotspot indices to determine overall indices representing a weighted sum of measures of lesion size. The indices used in this example are used to assess cancer status for patients imaged using a PSMA binding agent and PET-CT imaging.

In particular, individual hotspot indices are determined via interpolation from our reference levels similar to the approach described in Example 5. In this example, reference VOIs corresponding to an aorta portion and a liver portion are segmented and mapped to corresponding 3D volumes in a PET image. The aorta portion volume is used to determine a blood reference intensity, and the liver volume is used to determine a liver reference intensity. In this example, each reference intensity is determined from its corresponding volume by taking an average intensity (SUV) in the corresponding volume, but other measures, such as a maximum, peak, or median value could also be used. Reference levels on a scale, referred to as a Lesion PSMA Score (LPS), are assigned to intensity values based on the blood and liver reference intensities (SUVs) as follows: a LPS of 0 is assigned to a 0 SUV level, an LPS of 1 is assigned to the blood reference intensity, an LPS of 2 is assigned to the liver reference intensity, and a maximum LPS of 3 is assigned to a reference intensity calculated as twice the liver reference intensity.

Individual hotspots are assigned LPS scores based on their individual intensities. For individual hotspots having intensities ranging from 0 to the maximum reference intensity (twice the liver reference intensity), the LPS score corresponding to the individual hotspot intensity is interpolated from the reference scale. Hotspots having intensities greater than the maximum reference intensity are assigned the maximum LPS of 3.

Two example overall risk indices that can be computed using detected hotspots and the individual hotspot indices (LPS scores) are calculated as weighted sums of hotspot sizes in particular volumes corresponding to tissue regions where cancerous lesions may occur. A first example index is a PSMA-weighted total bone/lymph/prostate lesion volume or ratio (PTLV or PTLR). This index is a weighted sum of lesion volumes, the weight being the lesion PSMA score. The sum is computed separately for 3D volumes corresponding to bone (e.g., a skeletal region), lymph nodes, and prostate as the weighted sum of hotspot volumes for hotspots found in each particular region. In particular, the weighted sum is computed as follows:

$$\Sigma >(\text{lesion volume} \times \text{lesion psma score})$$

In certain case, a ratio may be preferable and can be computed by dividing the weighted sum by the total 3D volume of the particular region (e.g., in the PET image). Weighting summed hotspot volumes by LPS, as opposed to, for example SUV or normalized SUV is advantageous since it PSMA expression in the form of (normalized) SUV values may not relate to aggressiveness of the disease in a linear fashion. That is, for example, it is not a given that a hotspot with an intensity of 100 represents a lesion is five times worse than one represented by a hotpot having an intensity of 20. Calculating the LPS score and weighting hotspots by the LPS score provides a scale to compare different hotspots.

Another example index is a PSMA-weighted bone/lymph aggregated diameter (PLAD). This index is also a sum of a measure of lesion size, weighted by LPS score, but instead of volume this index uses an average diameter (e.g., averaged of x, y, and z-diameters) of each hotspot. Since volume is a three-dimensional quantity, a minor change in volume for a large lesion can dominate (e.g., cause large fluctuations in the sum) over changes in size of smaller lesions. Using the average diameter instead mitigates this effect. This index is calculated as follows:

$$\Sigma >(\text{lesion average diameter} \times \text{lesion psma score})$$

The weighed aggregated diameter can be calculated for the bone and lymph.

vii. Example 8: Improved Performance in AI-Assisted Image Analysis for Patients with Low or Intermediate Risk Prostate Cancer 99mTc MIP-1404 (1404) is a PSMA targeted imaging agent for the detection and staging of clinically significant prostate cancer. Manual assessment of tracer uptake in SPECT/CT images introduces inherent limitations in inter- and intra-reader standardization. This example describes a study that evaluated the performance of PSMA-AI assisted reads, wherein automated segmentation of prostate volumes and other target tissue regions are performed in accordance with the embodiments described herein, over manual assessment and known clinical predictors.

The study analyzed 464 evaluable patients with very low-, low-, or intermediate-risk prostate cancer, whose diagnostic biopsy indicated a Gleason grade of ≤ 3+4 and/or who were candidates for active surveillance (1404-3301). All subjects received an IV injection of 1404 and SPECT/CT imaging was performed 3-6 hours postdose. Three independent readers evaluated the images. All subjects underwent either voluntary RP (low- and intermediate-risk) or prostate biopsy (very low-risk) post dosing. Clinically significant disease was declared in subjects with Gleason grade 7 or higher. The PSMA-AI was developed and locked prior to the analysis. Three different independent readers used PSMA-AI to obtain quantitative expression of 1404 in the prostate against the background (PSMA-Index). PSMA-Index for all readers and subjects were compared to the histopathological reference, yielding 6 receiver operating characteristic (ROC) curves (3 manual reads+3 PSMA-AI assisted reads). The clinical performance of the 1404 PSMA-AI assisted read was also evaluated by comparing the Area Under the ROC Curve (AUC), of a multivariate model (PSA, clinical staging and diagnostic Gleason score) with and without PSMA-Index.

The manual reads demonstrated AUCs of 0.62, 0.62 and 0.63. The reads with PSMA-AI demonstrated AUCs of 0.65, 0.66 and 0.66. The PSMA-AI performance in terms of AUC was higher than manual in all 3*3=9 pairwise comparisons between the two reader groups, with statistically significant improvement observed in five cases (nominal $p<0.05$), not accounting for multiple comparisons. The predictive ability of the baseline multivariate model, without PSMA-Index, was at AUC 0.74. Upon adding of PSMA-Index, the model predictive ability increased to AUC 0.77. The logistic regression model indicated that PSMA-Index ($p=0.004$), pre-surgery PSA (0.018) and % positive cores ($p=<0.001$) were significantly associated with clinically significant disease. When measuring reproducibility, log (PSMA-Index) correlation coefficients for pairs of PSMAAI readers were 0.94, 0.97 and 0.98.

Accordingly, the study described in this example demonstrated that PSMA-AI provides a standardized platform to generate reproducible quantitative assessment of 1404. The PSMA-AI assisted read demonstrated an additive improvement over known predictors for identifying men with clinically significant disease.

ix. Example 9: Automated Calculation of PSMA Indices for Quantification of 18F-DCFPyL Uptake from PET/CT Images for Prostate Cancer Staging This example demonstrates automated image segmentation, lesion detection, and calculation of a standardized index score based on hotspot indices assigned to detected lesions via embodiments of the approaches described herein. The automated image analysis procedures are used for evaluated cancer status of patients imaged via PET/CT scanning after being administered the radiopharmaceutical 18F-DCFPyL (PyL™).

In this example, a cascaded deep learning pipeline was used to segment relevant organs in the CT image, and segmentations are projected into PET image space. In particular, target regions corresponding to a bone volume corresponding to bones of the subject, a lymph volume corresponding to lymph regions, and a prostate volume corresponding to a prostate gland were segmented in the CT image and mapped to identify corresponding 3D volumes in the PET image. Likewise, aorta and liver volumes corresponding to an aorta portion and a liver were also segmented and mapped to the PET image for use as reference regions as described herein.

Hotspots were detected in the PET image. Hotspots that were considered to represent lesions are manually segmented, as well as additional lesions not detected by the algorithm. Each individual detected hotspot was quantified by calculating an individual hotspot index referred to as lesion miPSMA index (LPI). As described in Examples 6 and 7 above, the LPI used in this example is a continuous index computed using automatically segmented (as opposed to manually identified) volumes. Accordingly, it offers advantages over previous approaches that utilize manual identification of various organs in images, and which only classify lesions using a small, finite, number of enumerated values. Accordingly, this approach provides more detailed information that can be utilized to manage treatment strategy and track disease progression and/or treatment efficacy over time in a finely grained and accurate fashion.

The LPI for each detected hotspot was computed based on reference values determined from blood pool (as measured from an identified aorta volume) and liver reference regions, e.g., similar to that described in Example 7 above. In particular, a blood pool reference intensity (SUV value) was measured using an aorta volume within the PET image, and a liver reference intensity was measured from a liver volume identified in the PET image. Both the blood pool and liver reference intensity levels were measured as the mean SUV ($SUV_{mean}$) within the corresponding volume in a PET image. Reference LPI index values of 1 and 2 were assigned to the blood pool and liver reference intensities, respectively. A maximal reference index level of 3 was assigned to a reference intensity corresponding to twice the liver reference intensity value.

Each individual detected hotspots was assigned LPI scores based (i) a measured hotspot intensity value for the hotspot and (ii) comparison with the blood pool and liver reference intensity values and the aforementioned reference index levels. In particular, for each hotspot, an individual hotspot intensity value corresponding to a mean lesion uptake was calculated as a mean SUV across voxels of the hotspot. For an individual hotspot, an LPI equal to 1 was assigned if the mean lesion standard uptake value ($SUV_{mean}$) equal to the blood pool reference value; an LPI equal to 2 was assigned for hotspots having mean lesion uptake values equal to the liver reference uptake value; and an LPI equal to 3 was assigned to hotspots having a mean lesion uptake value is equal to or above twice the liver reference uptake. For hotspots having intensities in falling in between reference intensity values, individual hotspot LPIs were interpolated from based on the hotspot intensity value and reference intensity-index value pairs.

An aggregated lesion volume within the bone region was computed as a weighted sum of volumes of individual hotspots detected within the bone volume in the PET image, with the volume of each hotspot weighted by its corresponding LPI. In this manner a PSMA-weighted Total Lesion Volume (PLTV) index was computed for the bone region, denoted $PTLV_{bone}$. PLTV index values were also computed for the lymph ($PTLV_{lymph}$) and prostate ($PTLV_{prostate}$) regions analogously. For each of the three regions, PET/CT image data sets for subjects having various different indications were used to automatically determine PLTV index values.

Performance of the AI-based automated technique was evaluated based on comparison with manual organ segmentation and annotation of images to identify hotspots, and PLTV index values computed for different indications were compared across regions.

Using manual expert interpretation as a gold standard for comparison, the automated hotspot detection algorithm was determined to have sensitivity of 92.1% for bone lesions (97.2% in the 52 automatically segmented bones) and 96.2% for lymph lesions. On average, 17 bone hotspots were detected per scan and 23 lymph hotspots were detected per scan.

PLTV index values were computed using a sample dataset of 197 PET/CT images for the bone region, 99 PET/CT image for the lymph region, and 43 PET/CT images for the prostate region. In the data sets, 94% of individual hotspot LPI's determined were between 1 and 3, with minimum LPIs determined for bone, lymph, and prostate regions of 0.82, 1.1, and 1.3, respectively. Median LPI values for the bone, lymph, and prostate regions were 1.5, 2.0, and 2.3, respectively.

For each region, PLTV indices were computed for subjects having various different indications as follows: Treatment Response (TR), Screening (S), Newly Diagnosed (ND), Metastatic (M), Suspected Recurrence (SR), Recurrent (R). PLTV index values were compared across indications by calculating the means of the values in the interquartile range ($IQR_{mean}$), hence excluding outliers. Ordering indications by $IQR_{mean}$ of the PLTV values yields TR<S<ND<R<SR<M for the bone region, S=M<R<ND<SR for lymph region, and M<SR<R<S<ND for prostate region, aligning well with clinical expectations of disease state.

Figure 19:
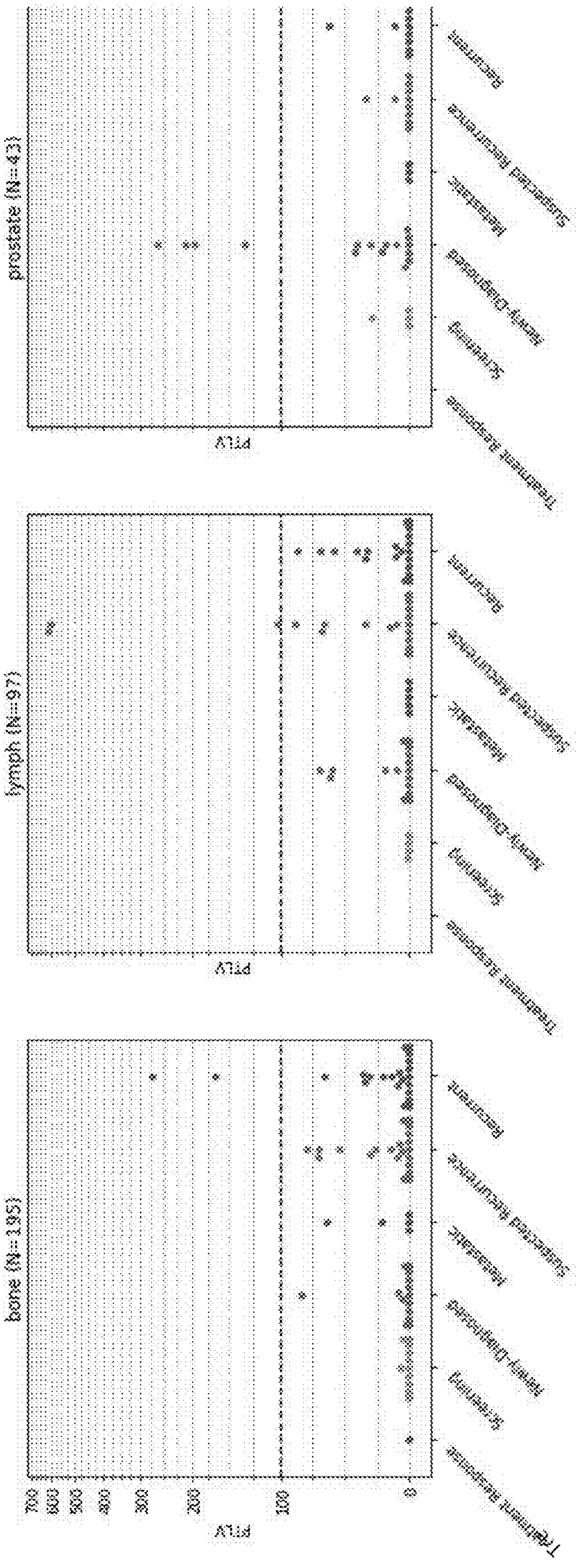
FIG. 19 is a set of three graph, each graphs showing overall index values quantifying PyL™-PSMA uptake in lesions identified in a particular tissue region based on PET/CT image analysis for six different cancer indications, according to an illustrative embodiment.
Figure 20:
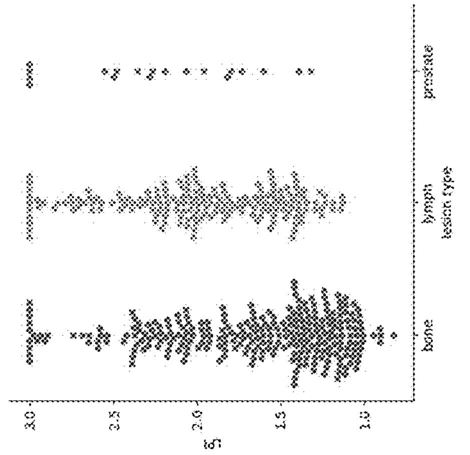
FIG. 20 is a graph showing individual lesion PSMA index (LPI) values determined for lesions detected in three different tissue regions (bone, lymph, and prostate) via PET/CT image analysis, according to an illustrative embodiment.

FIG. 19 shows PLTV index values determined for the various indications for each region. FIG. 20 shows a scatter plot of individual hotspot LPI values for hotspots detected in each of the three regions.

Figure 21:
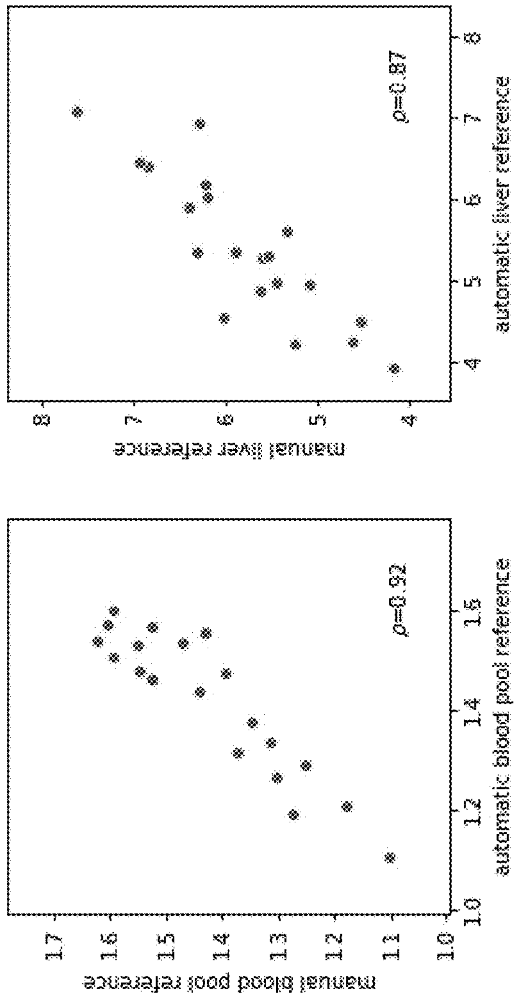
FIG. 21 is a set of two graphs comparing reference values determined via manual and automated image analysis for a blood pool reference value and a liver reference value according to an illustrative embodiment.

In comparison with manual approaches for determining reference values for grading lesions, such as the of Eiber et al., 2017, the blood and liver automated reference values are based on a larger image volume compared to the manual reference method and are hence expected to be more robust. FIG. 21 compares reference values computed via the automated segmentation approaches described herein for the blood pool (left graph) and liver (right graph) regions with reference values computed using manual identification of organ boundaries. As shown in FIG. 21, in a sample of 20 PET/CT scans, the correlation (Pearson's r) between automated and manual reference was 0.92 for blood and 0.87 for liver.

Accordingly, this example demonstrates use of the automated segmentation, hotspot detection, and index value calculation for detecting cancer and tracking cancer progression and/or response to treatment over time.

D. Imaging Agents

In certain embodiments, 3D functional images are nuclear medicine images that use imaging agents comprising radiopharmaceuticals. Nuclear medicine images are obtained following administration of a radiopharmaceutical to a patient, and provide information regarding the distribution of the radiopharmaceutical within the patient. Radiopharmaceuticals are compounds that comprise a radionuclide.

Nuclear medicine images (e.g., PET scans; e.g., SPECT scans; e.g., whole-body scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. Risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example $^{18}$F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. As described in the following, risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties.

i. PET Imaging Radionuclide Labelled PSMA Binding Agents

In certain embodiments, the radionuclide labelled PSMA binding agent is a radionuclide labelled PSMA binding agent appropriate for PET imaging.

In certain embodiments, the radionuclide labelled PSMA binding agent comprises [18F]DCFPyL (also referred to as PyL™; also referred to as DCFPyL-18F):

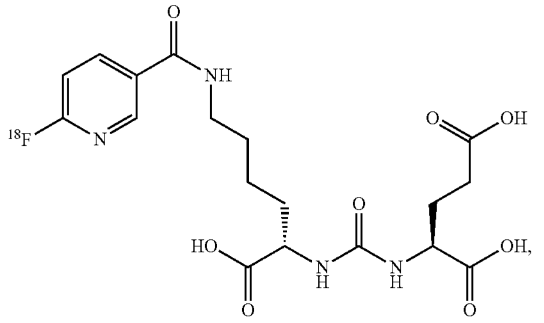

[18F]DCFPyL or a pharmaceutically acceptable salt thereof.

In certain embodiments, the radionuclide labelled PSMA binding agent comprises [18F]DCFBC:

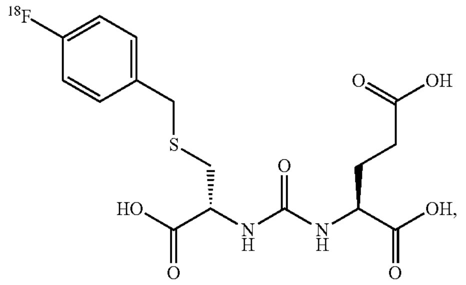

[18F]DCFBC or a pharmaceutically acceptable salt thereof.

In certain embodiments, the radionuclide labelled PSMA binding agent comprises $^{68}$Ga-PSMA-HBED-CC (also referred to as $^{68}$Ga-PSMA-11):

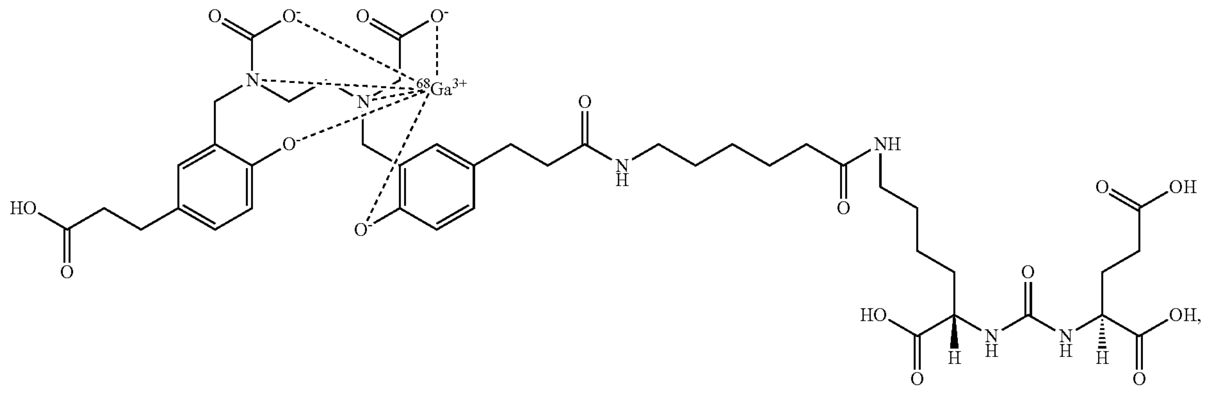

$^{68}$Ga-PSMA-HBED-CC or a pharmaceutically acceptable salt thereof.

In certain embodiments, the radionuclide labelled PSMA binding agent comprises PSMA-617:

PSMA-617

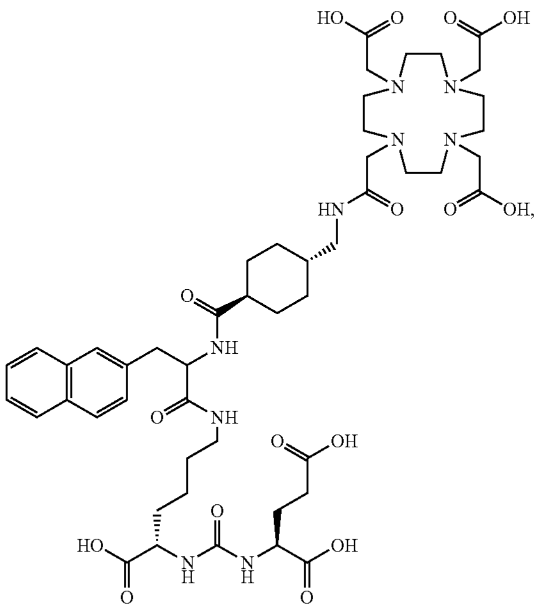

or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, the radionuclide labelled PSMA binding agent comprises $^{177}$Lu-PSMA-617, which is PSMA-617 labelled with $^{177}$Lu, or a pharmaceutically acceptable salt thereof.

In certain embodiments, the radionuclide labelled PSMA binding agent comprises PSMA-I&T:

PSMA I&T

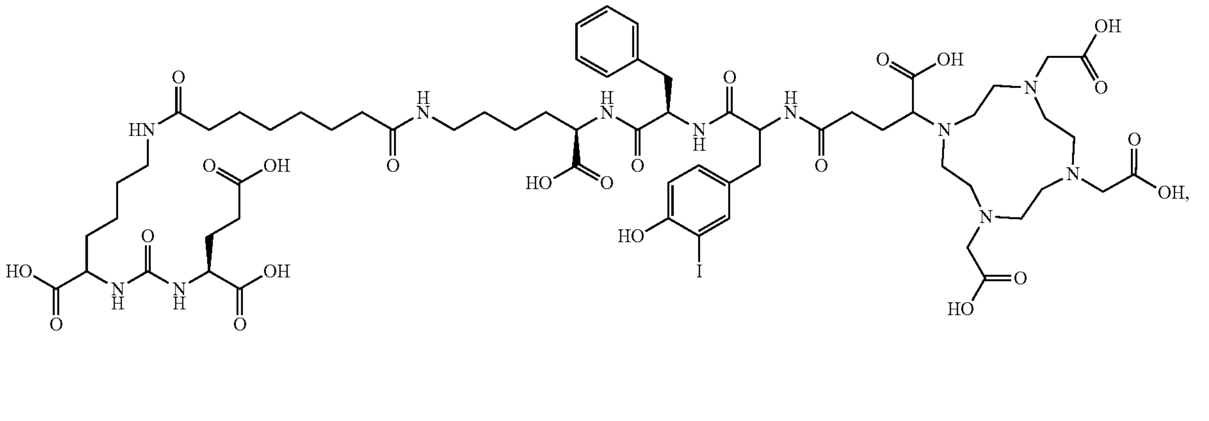

or a pharmaceutically acceptable salt thereof. In certain embodiments, the radionuclide labelled PSMA binding agent comprises $^{68}$Ga-PSMA-I&T, which is PSMA-I&T labelled with $^{68}$Ga, or a pharmaceutically acceptable salt thereof.

In certain embodiments, the radionuclide labelled PSMA binding agent comprises PSMA-1007:

PSMA-1007

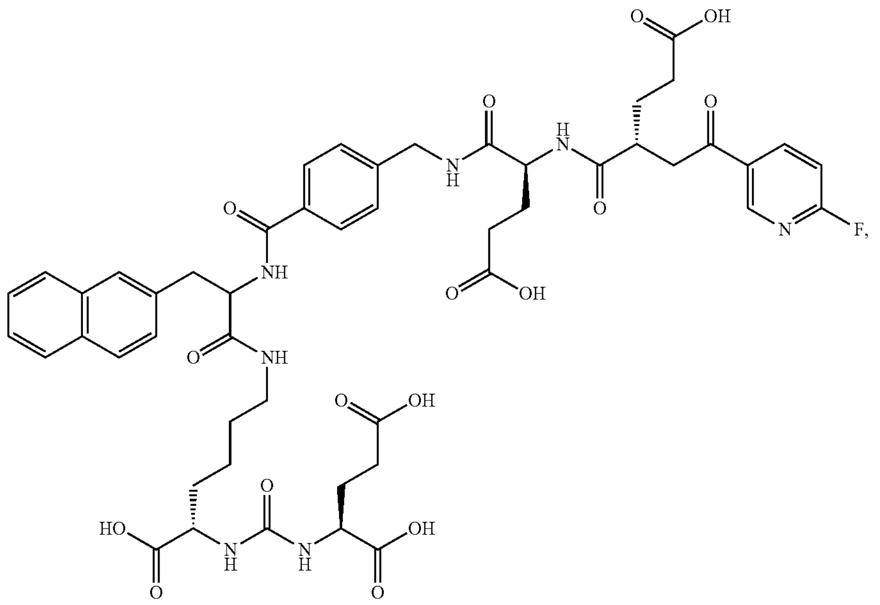

or a pharmaceutically acceptable salt thereof. In certain embodiments, the radionuclide labelled PSMA binding agent comprises $^{18}F$-PSMA-1007, which is PSMA-1007 labelled with $^{18}F$, or a pharmaceutically acceptable salt thereof.

ii. SPECT Imaging Radionuclide Labelled PSMA Binding Agents

In certain embodiments, the radionuclide labelled PSMA binding agent is a radionuclide labelled PSMA binding agent appropriate for SPECT imaging.

In certain embodiments, the radionuclide labelled PSMA binding agent comprises 1404 (also referred to as MIP-1404):

1404

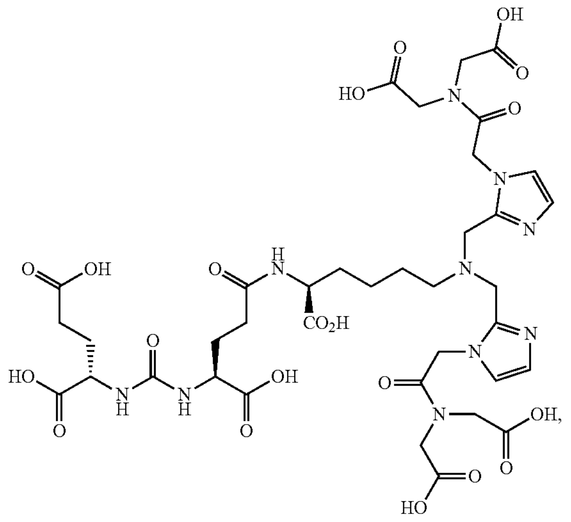

or a pharmaceutically acceptable salt thereof.

In certain embodiments, the radionuclide labelled PSMA binding agent comprises 1405 (also referred to as MIP-1405):

1405

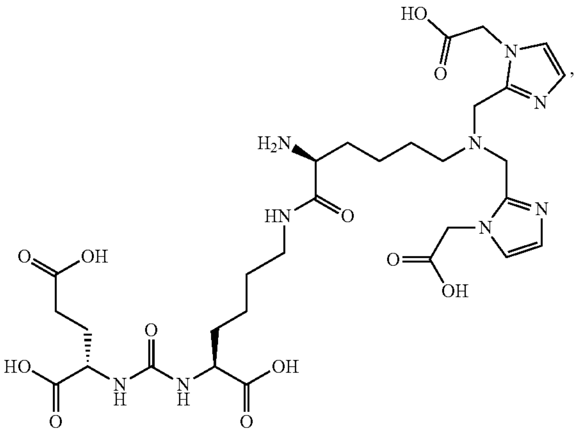

or a pharmaceutically acceptable salt thereof.

In certain embodiments, the radionuclide labelled PSMA binding agent comprises 1427 (also referred to as MIP-1427):

1427

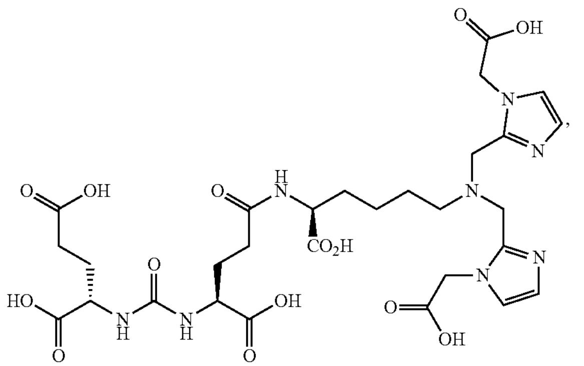

or a pharmaceutically acceptable salt thereof.

In certain embodiments, the radionuclide labelled PSMA binding agent comprises 1428 (also referred to as MIP-1428):

1428

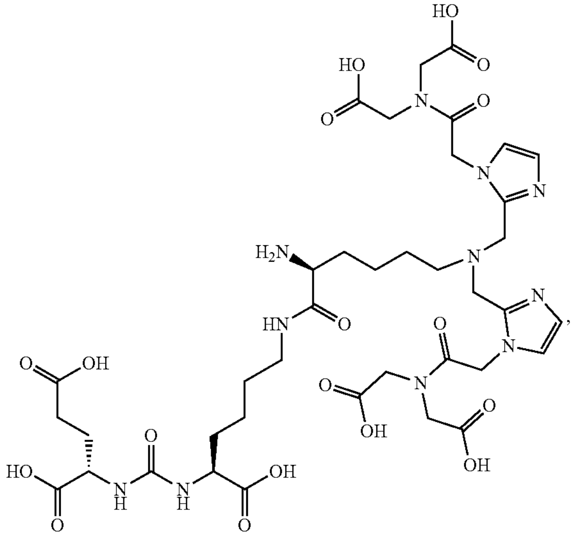

or a pharmaceutically acceptable salt thereof.

In certain embodiments, the PSMA binding agent is labelled with a radionuclide by chelating it to a radioisotope of a metal [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-$^{186}$ ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)].

In certain embodiments, 1404 is labelled with a radionuclide (e.g., chelated to a radioisotope of a metal). In certain embodiments, the radionuclide labelled PSMA binding agent comprises $^{99m}$Tc-MIP-1404, which is 1404 labelled with (e.g., chelated to) $^{99m}$Tc:

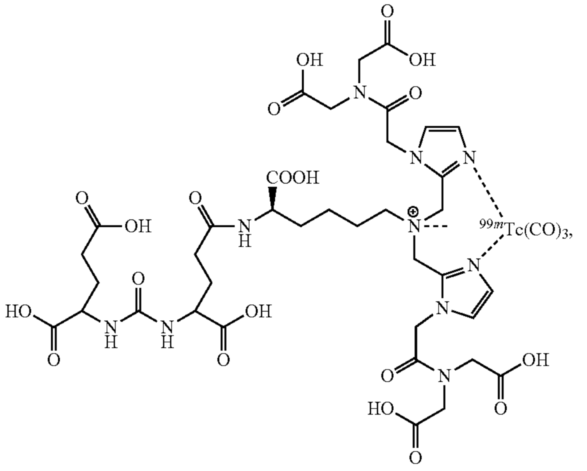

$^{99m}$Tc-MIP-1404 or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-$^{186}$ ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-$^{1404}$, with the other metal radioisotope substituted for $^{99m}$Tc.

In certain embodiments, 1405 is labelled with a radionuclide (e.g., chelated to a radioisotope of a metal). In certain embodiments, the radionuclide labelled PSMA binding agent comprises $^{99m}$Tc-MIP-1405, which is 1405 labelled with (e.g., chelated to) $^{99m}$Tc:

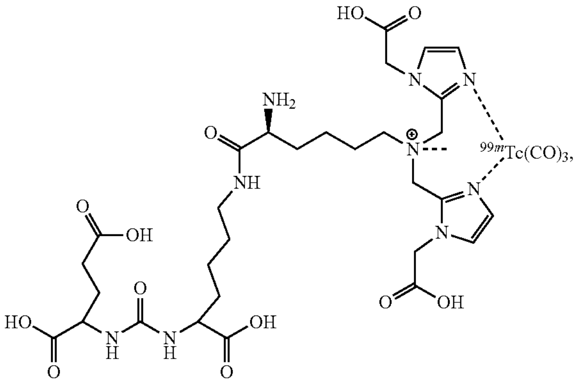

$^{99m}$Tc-MIP-1405 or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-$^{186}$ ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1405, with the other metal radioisotope substituted for $^{99m}$Tc.

In certain embodiments, 1427 is labelled with (e.g., chelated to) a radioisotope of a metal, to form a compound according to the formula below:

1427

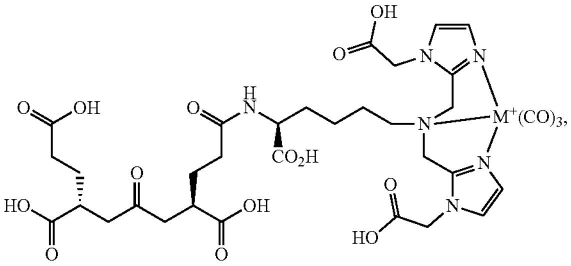

chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-$^{186}$ ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1427 is labelled.

In certain embodiments, 1428 is labelled with (e.g., chelated to) a radioisotope of a metal, to form a compound according to the formula below:

1428

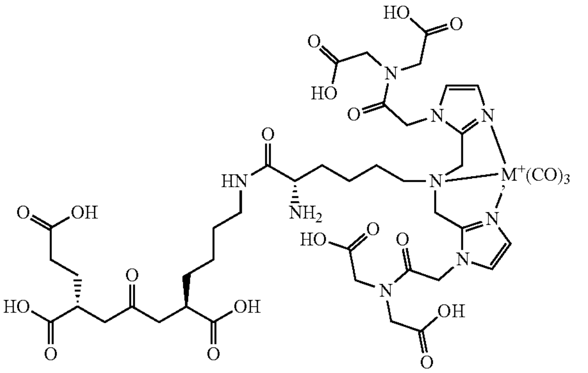

chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1428 is labelled.

In certain embodiments, the radionuclide labelled PSMA binding agent comprises PSMA I&S:

PSMA I&S

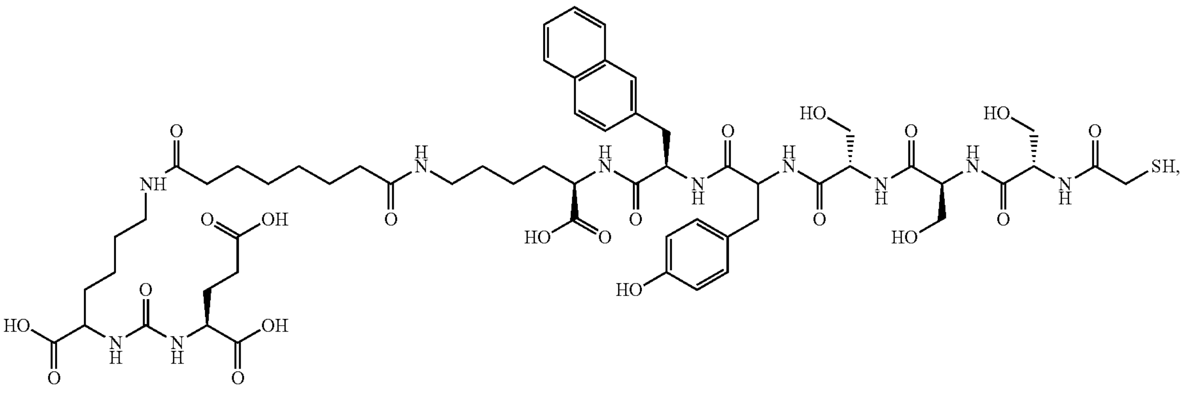

or a pharmaceutically acceptable salt thereof. In certain embodiments, the radionuclide labelled PSMA binding agent comprises $^{99m}$Tc-PSMA I&S, which is PSMA I&S labelled with $^{99m}$Tc, or a pharmaceutically acceptable salt thereof.

E. Computer System and Network Architecture

Figure 17:
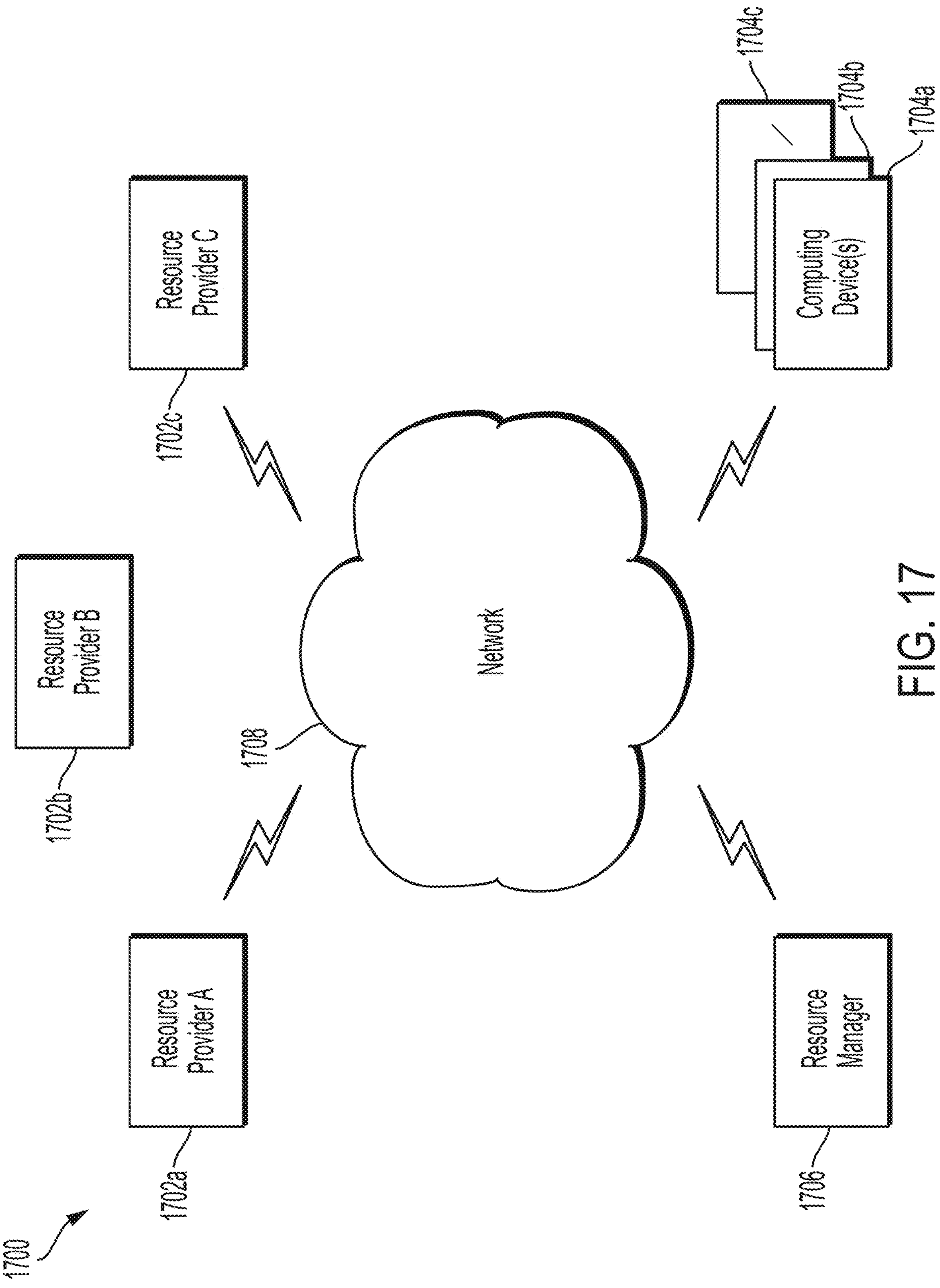
FIG. 17 is a block diagram of an exemplary cloud computing environment, used in certain embodiments.

As shown in FIG. 17, an implementation of a network environment 1700 for use in providing systems, methods, and architectures described herein is shown and described. In brief overview, referring now to FIG. 17, a block diagram of an exemplary cloud computing environment 1700 is shown and described. The cloud computing environment 1700 may include one or more resource providers 1702*a*, 1702*b*, 1702*c* (collectively, 1702). Each resource provider 1702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1702 may be connected to any other resource provider 1702 in the cloud computing environment 1700. In some implementations, the resource providers 1702 may be connected over a computer network 1708. Each resource provider 1702 may be connected to one or more computing device 1704*a*, 1704*b*, 1704*c* (collectively, 1704), over the computer network 1708.

The cloud computing environment 1700 may include a resource manager 1706. The resource manager 1706 may be connected to the resource providers 1702 and the computing devices 1704 over the computer network 1708. In some implementations, the resource manager 1706 may facilitate the provision of computing resources by one or more resource providers 1702 to one or more computing devices 1704. The resource manager 1706 may receive a request for a computing resource from a particular computing device 1704. The resource manager 1706 may identify one or more resource providers 1702 capable of providing the computing resource requested by the computing device 1704. The resource manager 1706 may select a resource provider 1702 to provide the computing resource. The resource manager 1706 may facilitate a connection between the resource provider 1702 and a particular computing device 1704. In some implementations, the resource manager 1706 may establish a connection between a particular resource provider 1702 and a particular computing device 1704. In some implementations, the resource manager 1706 may redirect a particular computing device 1704 to a particular resource provider 1702 with the requested computing resource.

Figure 18:
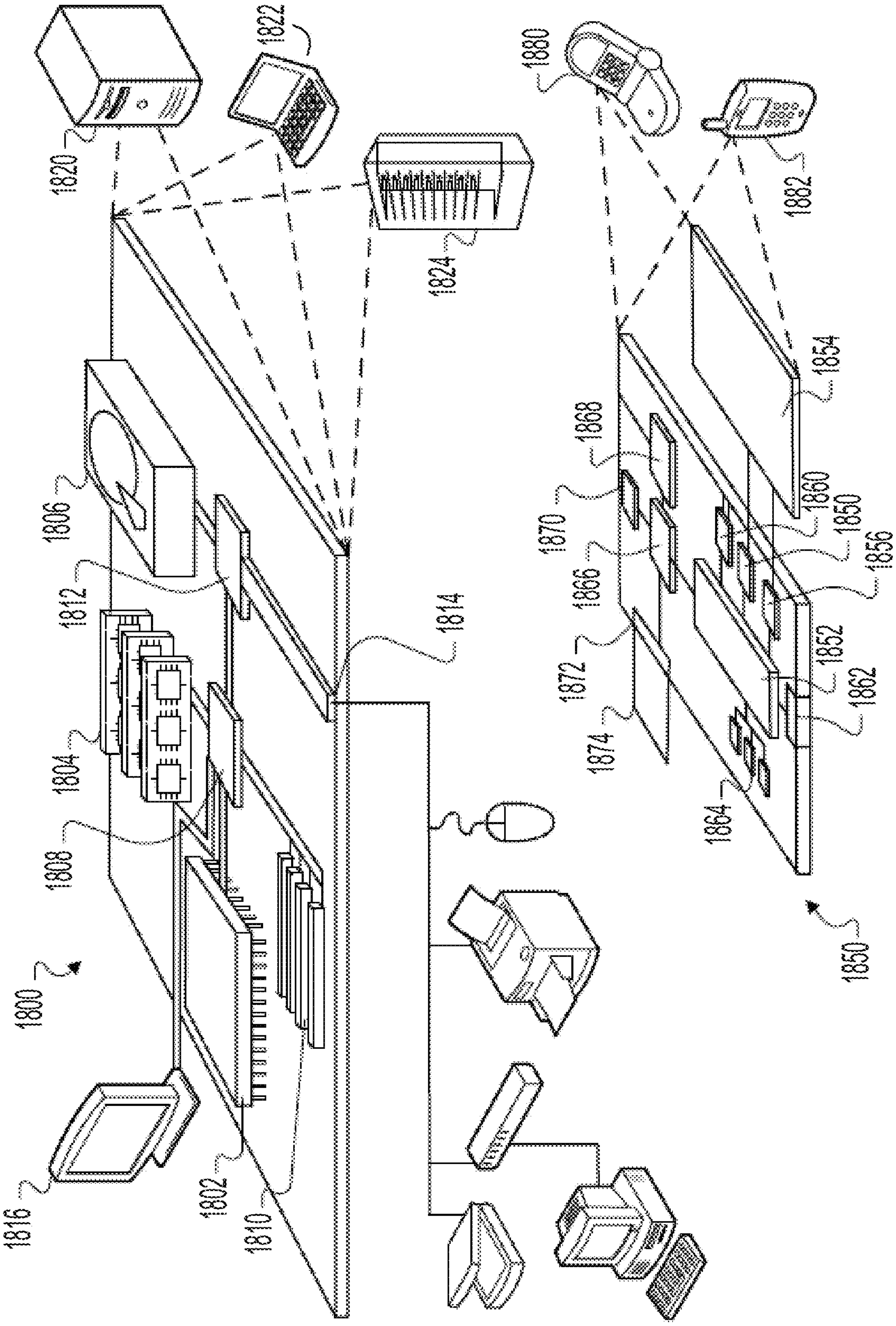
FIG. 18 is a block diagram of an example computing device and an example mobile computing device used in certain embodiments.

FIG. 18 shows an example of a computing device 1800 and a mobile computing device 1850 that can be used to implement the techniques described in this disclosure. The computing device 1800 is intended to represent various forms of digital computers, such as laptops, desktops, workstations, personal digital assistants, servers, blade servers, mainframes, and other appropriate computers. The mobile computing device 1850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and may be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1804 stores information within the computing device 1800. In some implementations, the memory 1804 is a volatile memory unit or units. In some implementations, the memory 1804 is a non-volatile memory unit or units. The memory 1804 may also be another form of computer-readable medium, such as a magnetic or optical disk.

The storage device 1806 is capable of providing mass storage for the computing device 1800. In some implementations, the storage device 1806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1802), perform one or more methods, such as those described above. The instructions can also be stored by one or more storage devices such as computer- or machine-readable mediums (for example, the memory 1804, the storage device 1806, or memory on the processor 1802).

The high-speed interface 1808 manages bandwidth-intensive operations for the computing device 1800, while the low-speed interface 1812 manages lower bandwidth-intensive operations. Such allocation of functions is an example only. In some implementations, the high-speed interface 1808 is coupled to the memory 1804, the display 1816 (e.g., through a graphics processor or accelerator), and to the high-speed expansion ports 1810, which may accept various expansion cards (not shown). In the implementation, the low-speed interface 1812 is coupled to the storage device 1806 and the low-speed expansion port 1814. The low-speed expansion port 1814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1800 may be implemented in a number of different forms, as shown in the figure. For example, it may be implemented as a standard server 1820, or multiple times in a group of such servers. In addition, it may be implemented in a personal computer such as a laptop computer 1822. It may also be implemented as part of a rack server system 1824. Alternatively, components from the computing device 1800 may be combined with other components in a mobile device (not shown), such as a mobile computing device 1850. Each of such devices may contain one or more of the computing device 1800 and the mobile computing device 1850, and an entire system may be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 may also be provided with a storage device, such as a micro-drive or other device, to provide additional storage. Each of the processor 1852, the memory 1864, the display 1854, the communication interface 1866, and the transceiver 1868, are interconnected using various buses, and several of the components may be mounted on a common motherboard or in other manners as appropriate.

The processor 1852 can execute instructions within the mobile computing device 1850, including instructions stored in the memory 1864. The processor 1852 may be implemented as a chipset of chips that include separate and multiple analog and digital processors. The processor 1852 may provide, for example, for coordination of the other components of the mobile computing device 1850, such as control of user interfaces, applications run by the mobile computing device 1850, and wireless communication by the mobile computing device 1850.

The processor 1852 may communicate with a user through a control interface 1858 and a display interface 1856 coupled to the display 1854. The display 1854 may be, for example, a TFT (Thin-Film-Transistor Liquid Crystal Display) display or an OLED (Organic Light Emitting Diode) display, or other appropriate display technology. The display interface 1856 may comprise appropriate circuitry for driving the display 1854 to present graphical and other information to a user. The control interface 1858 may receive commands from a user and convert them for submission to the processor 1852. In addition, an external interface 1862 may provide communication with the processor 1852, so as to enable near area communication of the mobile computing device 1850 with other devices. The external interface 1862 may provide, for example, for wired communication in some implementations, or for wireless communication in other implementations, and multiple interfaces may also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 may also be provided and connected to the mobile computing device 1850 through an expansion interface 1872, which may include, for example, a SIMM (Single In Line Memory Module) card interface. The expansion memory 1874 may provide extra storage space for the mobile computing device 1850, or may also store applications or other information for the mobile computing device 1850. Specifically, the expansion memory 1874 may include instructions to carry out or supplement the processes described above, and may include secure information also. Thus, for example, the expansion memory 1874 may be provide as a security module for the mobile computing device 1850, and may be programmed with instructions that permit secure use of the mobile computing device 1850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1852), perform one or more methods, such as those described above. The instructions can also be stored by one or more storage devices, such as one or more computer- or machine-readable mediums (for example, the memory 1864, the expansion memory 1874, or memory on the processor 1852). In some implementations, the instructions can be received in a propagated signal, for example, over the transceiver 1868 or the external interface 1862.

The mobile computing device 1850 may communicate wirelessly through the communication interface 1866, which may include digital signal processing circuitry where necessary. The communication interface 1866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1868 using a radio-frequency. In addition, short-range communication may occur, such as using a Bluetooth®, Wi-Fi™, or other such transceiver (not shown). In addition, a GPS (Global Positioning System) receiver module 1870 may provide additional navigation- and location-related wireless data to the mobile computing device 1850, which may be used as appropriate by applications running on the mobile computing device 1850.

The mobile computing device 1850 may also communicate audibly using an audio codec 1860, which may receive spoken information from a user and convert it to usable digital information. The audio codec 1860 may likewise generate audible sound for a user, such as through a speaker, e.g., in a handset of the mobile computing device 1850. Such sound may include sound from voice telephone calls, may include recorded sound (e.g., voice messages, music files, etc.) and may also include sound generated by applications operating on the mobile computing device 1850.

The mobile computing device 1850 may be implemented in a number of different forms, as shown in the figure. For example, it may be implemented as a cellular telephone 1880. It may also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the various modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically processing a 3D image to identify 3D volumes within the 3D image that correspond to particular target tissue regions, the method comprising:

(a) receiving, by a processor of a computing device, a 3D anatomical image of a subject obtained using an anatomical imaging modality, wherein the 3D anatomical image comprises a graphical representation of tissue within the subject;

(b) automatically identifying, by the processor, using one or more machine learning modules for each of a plurality of target tissue regions, a corresponding target volume of interest (VOI) within the 3D anatomical image;

(c) determining, by the processor, a 3D segmentation map representing a plurality of 3D segmentation masks, each 3D segmentation mask representing a particular identified target VOI;

(d) receiving, by the processor, a 3D functional image of the subject obtained using a functional imaging modality following administration to the subject of a radiopharmaceutical comprising a prostate-specific membrane antigen (PSMA) binding agent;

(e) identifying, by the processor, within the 3D functional image, one or more 3D volume(s), each corresponding to an identified target VOI, using the 3D segmentation map; and (f) determining, by the processor, using the one or more 3D volumes, one or more uptake metrics that represent uptake of the radiopharmaceutical in particular organs and/or tissue regions.

2. The method of claim 1, wherein the 3D anatomical image is a full body image.

3. The method of claim 1, wherein step (c) comprises digitally stitching together the plurality of 3D segmentation masks to form the 3D segmentation map.

4. The method of claim 1, wherein step (b) comprises, for at least one specific target tissue region:

determining, using a first module, an initial VOI within the 3D anatomical image, the initial VOI corresponding to an anatomical region containing the specific target tissue region; and identifying, using a second module, the target VOI corresponding to the specific target tissue region within the initial VOI.

5. The method of claim 4, wherein the second module is a CNN module that implements a CNN.

6. The method of claim 4, wherein the first module is a CNN module that implements a CNN to perform a coarse segmentation to automatically identify the initial VOI corresponding to the anatomical region containing the specific target tissue region.

7. The method of claim 4, wherein the first module receives a sub-sampled version of the anatomical image as input and identifies the initial VOI using the sub-sampled version of the anatomical image.

8. The method of claim 4, wherein the first module is a first CNN module and the second module is a second CNN module, and wherein the first CNN module comprises additional filters in order to account for increased variability in image size with respect to the second CNN module.

9. The method of claim 4, wherein the 3D anatomical image is a full body image and wherein step (b) comprises:

automatically determining, using one or more localization modules implementing machine learning technique(s), a plurality of initial VOIs within the 3D anatomical image, each initial VOI corresponding to a particular anatomical region and in which an associated subset of the target VOIs are located; and for each initial VOI, automatically identifying, using one or more segmentation modules implementing machine learning technique(s) the associated subset of target VOIs.

10. The method of claim 9, wherein the plurality of initial VOIs comprises one or more members selected from the group consisting of:

a pelvic region initial VOI corresponding to a pelvic region of the subject;

a spine region initial VOI corresponding to a spine of the subject;

a left upper body region initial VOI corresponding to a left side of the subject's upper body; and a right upper body region initial VOI corresponding to a right side of the subject's upper body.

11. The method of claim 1, comprising:

(g) determining, by the processor, a cancer status for the subject.

12. The method of claim 11, comprising performing steps (a)-(g) repeatedly for a plurality of anatomical and corresponding functional images collected at different time points to determine, at each time point, a cancer status of the subject, thereby tracking cancer status over time.

13. The method of claim 11, comprising:

(h) automatically adjusting, by the processor, intensities of voxels of the 3D functional image to correct for background uptake in one or more background tissue regions.

14. The method of claim 13, wherein the target tissue regions comprise the one or more background tissue regions and wherein step (h) comprises:

using the 3D segmentation map to identify, within the 3D functional image, one or more 3D background tissue volume(s), each corresponding to a particular background tissue region; and adjusting intensities of voxels of the 3D functional image based on intensities of voxels within the 3D background tissue volumes.

15. The method of claim 13, wherein the one or more background tissue regions comprise one or more members selected from the group consisting of: a bladder, a kidney, a duodenum, a small intestine, a spleen, a liver, a pancreas, a stomach, an adrenal gland, a rectum, and testes.

16. The method of claim 1, wherein:

the 3D anatomical image is an x-ray computed tomography (CT) image, and the 3D functional image is a 3D single photon emission computed tomography (SPECT) image.

17. The method of claim 1, wherein:

the 3D anatomical image is an x-ray computed tomography (CT) image, and the 3D functional image is a 3D positron emission tomography (PET) image.

18. The method of claim 1, wherein the radiopharmaceutical comprises [$^{18}$F] DCFPyL.

19. A system for automatically processing a 3D image to identify 3D volumes within the 3D image that correspond to particular target tissue regions, the system comprising:

a processor of a computing device; and a memory having instructions stored thereon, wherein the instructions, when executed by the processor, cause the processor to:

(a) receive a 3D anatomical image of a subject obtained using an anatomical imaging modality, wherein the 3D anatomical image comprises a graphical representation of tissue within the subject;

(b) automatically identify, using one or more machine learning modules, for each of a plurality of target tissue regions, a corresponding target volume of interest (VOI) within the 3D anatomical image;

(c) determine a 3D segmentation map representing a plurality of 3D segmentation masks, each 3D segmentation mask representing a particular identified target VOI;

(d) receive a 3D functional image of the subject obtained using a functional imaging modality following administration to the subject of a radiopharmaceutical comprising a prostate-specific membrane antigen (PSMA) binding agent;

(e) identify, within the 3D functional image, one or more 3D volume(s), each corresponding to an identified target VOI, using the 3D segmentation map; and (f) determine, using the one or more 3D volumes, one or more uptake metrics that represent uptake of the radiopharmaceutical in particular organs and/or tissue regions.

* * * * *